(12) United States Patent
Ming et al.

(10) Patent No.: US 10,842,869 B2
(45) Date of Patent: Nov. 24, 2020

(54) METHOD OF TREATING LUPUS BY ADMINISTERING HUMANIZED ANTI-CXCR5 (C-X-C MOTIF CHEMOKINE RECEPTOR 5) ANTIBODIES

(71) Applicant: SANOFI, Paris (FR)

(72) Inventors: Jeffrey Ming, Bryn Mawr, PA (US); Moshe E. Zilberstein, North Caldwell, NJ (US); Roghieh Karimi Anderesi, Paris (FR)

(73) Assignee: Sanofi, Paris (FR)

( * ) Notice: Subject to any disclaimer, the term of this patent is extended or adjusted under 35 U.S.C. 154(b) by 101 days.

(21) Appl. No.: 15/927,675

(22) Filed: Mar. 21, 2018

(65) Prior Publication Data

US 2018/0280500 A1    Oct. 4, 2018

Related U.S. Application Data

(60) Provisional application No. 62/475,173, filed on Mar. 22, 2017.

(30) Foreign Application Priority Data

Aug. 18, 2017   (EP) .................................... 17306079

(51) Int. Cl.
*A61K 39/395* (2006.01)
*A61K 39/00* (2006.01)
*C07K 16/28* (2006.01)
*A61P 37/02* (2006.01)

(52) U.S. Cl.
CPC ........ *A61K 39/395* (2013.01); *A61K 39/0008* (2013.01); *A61P 37/02* (2018.01); *C07K 16/2866* (2013.01); *A61K 2039/505* (2013.01); *A61K 2039/54* (2013.01); *A61K 2039/545* (2013.01); *A61K 2039/55* (2013.01); *C07K 2317/24* (2013.01); *C07K 2317/76* (2013.01)

(58) Field of Classification Search
CPC .............. A61K 39/0008; A61K 39/395; A61K 2039/505; A61K 2039/54; A61K 2039/545; A61K 2039/55; A61P 37/02; C07K 16/24; C07K 16/2866; C07K 16/76
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,816,567 A | 3/1989 | Cabilly et al. |
| 5,223,409 A | 6/1993 | Ladner et al. |
| 5,530,101 A | 6/1996 | Queen et al. |
| 5,534,617 A | 7/1996 | Cunningham et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,814,318 A | 9/1998 | Lonberg et al. |
| 5,869,619 A | 2/1999 | Studnicka |
| 8,647,622 B2 | 2/2014 | Lee et al. |

FOREIGN PATENT DOCUMENTS

| | | |
|---|---|---|
| EP | 0239400 | 3/1987 |
| EP | 0332424 | 9/1989 |
| EP | 0338745 | 10/1989 |
| EP | 0519596 | 12/1992 |
| EP | 0592106 | 4/1994 |
| WO | WO 89/09622 | 10/1989 |
| WO | WO 1991/009967 | 7/1991 |
| WO | WO 1991/010741 | 7/1991 |
| WO | WO 93/16185 | 8/1993 |
| WO | WO 93/21319 | 10/1993 |
| WO | WO 1996/033735 | 10/1996 |
| WO | WO 1996/034096 | 10/1996 |
| WO | WO 1998/016654 | 4/1998 |
| WO | WO 1998/024893 | 6/1998 |
| WO | WO 1998/046645 | 10/1998 |
| WO | WO 1998/050433 | 11/1998 |
| WO | WO 2006/042333 | 4/2006 |
| WO | WO 2009/032661 | 3/2009 |
| WO | WO 2012/010582 | 1/2012 |
| WO | WO 2016/028573 | 2/2016 |

OTHER PUBLICATIONS

Paul Eggleton and Frank J. Ward (eds.), Systemic Lupus Erythematosus: Methods and Protocols, Methods in Molecular Biology, vol. 1134. © Springer Science+Business Media New York 2014. DOI 10.1007/978-1-4939-0326-9_3.*

Chang et al., "Therapeutic options for cutaneous lupus erythematosus: recent advances and future prospects," Expert Rev Clin Immunol. 12(10):1109-21 (2016).

ClinicalTrials.gov: "Pharmacodynamics Assessment Study After Single Subcutaneous Dose of SAR113244 Versus Placebo in Lupus Male and Female Patients," URL: https://clinicaltrials.gov/ct2/show/NCT02331810 (Jun. 3, 2016) retrieved on May 18, 2018 (p. 1-7).

Rahman et al., "Systemic Lupus Erythematosus," N Engl J Med. 358(9):929-39 (2008).

Weiner et al., "CXCR5 is critically involved in progression of lupus through regulation of B cell and double-negative T cell trafficking : CXCR5 deficiency ameliorates murine lupus," Clin Exp Immunol. 185(1):22-32 (2016).

(Continued)

*Primary Examiner* — Robert S Landsman

(74) *Attorney, Agent, or Firm* — McDonnell Boehnen Hulbert & Berghoff LLP

(57) ABSTRACT

This disclosure provides anti-CXCR5 antibodies and their use in the amelioration, treatment, or prevention of lupus. The disclosure also provides prophylactic, immunotherapeutic, and diagnostic compositions comprising an anti-CXCR5 antibody, and the use of such anti-CXCR5 antibodies in methods of preventing or treating lupus in mammals, including humans.

17 Claims, 8 Drawing Sheets

Specification includes a Sequence Listing.

(56) References Cited

OTHER PUBLICATIONS

International Search Report and Written Opinion issued by the International Searching Authority for International Application No. PCT/EP2018/057310; dated Jun. 25, 2014 (pp. 1-16).
Adey et al., Chapter 16, "Preparation of Second-Generation Phage Libraries", pp. 277-291, Phage Display of Peptides and Proteins, A Laboratory Manual, eds. Kay et al., Academic Press (1996).
Amit et al., "Three-dimensional structure of an antigen-antibody complex at 2.8 A resolution," 233(4765) Science 747-53 (Aug. 1986).
Barbas et al., "Assembly of combinatorial antibody libraries on phage surfaces: the gene III site," 88(18) Proc Natl Acad Sci USA 7978-82 (Sep. 1991).
Barbas et al., "In vitro evolution of a neutralizing human antibody to human immunodeficiency virus type 1 to enhance affinity and broaden strain cross-reactivity," 91(9) Proc Natl Acad Sci USA 3809-13 (Apr. 1994).
Bass et al., "Hormone phage: an enrichment method for variant proteins with altered binding properties," Proteins; 8 (4):309-14 (1990).
Boder et al., "Directed evolution of antibody fragments with monovalent femtomolar antigen-binding affinity," 97(20) Proc Natl Acad Sci USA 10701-5 (Sep. 2000).
Brennan et al., "Preparation of bispecific antibodies by chemical recombination of monoclonal immunoglobulin G1 fragments," Science 229(4708):81-83 (Jul. 1985).
Buoen et al., "How first-time-in-human studies are being performed: a survey of phase I dose-escalation trials in healthy volunteers published between 1995 and 2004," J Clin Pharmacol. 45(10):1123-36 (2005).
Carter et al., "High level *Escherichia coli* expression and production of a bivalent humanized antibody fragment," 10(2) Biotechnology 163-7 (Feb. 1992).
Carter et al., "Humanization of an anti-p185HER2 antibody for human cancer therapy," Proc Natl Acad Sci USA 89(10):4285-9 (May 1992).
Chothia & Lesk, "Canonical structures for the hypervariable regions of immunoglobulins," J Mol Biol. 196(4):901-17 (1987).
Creighton, Proteins: Structure and Molecular Properties, W.H. Freeman &Co., New York, pp. 78-87 (1st Edition, 1984).
Cunningham & Wells, "High-resolution epitope mapping of hGH-receptor interactions by alanine-scanning mutagenesis," 244(4908) Science 1081-5 (1989).
Cwirla et al., "Peptides on phage: a vast library of peptides for identifying ligands," 87(16) Proc Natl Acad Sci USA 6378-82 (1990).
Davies & Riechmann, "Affinity improvement of single antibody VH domains: residues in all three hypervariable regions affect antigen binding," 2(3) Immunotechnology 169-79 (1996).
Devlin et al., "Random Peptide Libraries: A Source of Specific Protein Binding Molecules," Science 249(4967): 404-06 (1990).
Furukawa et al., "A role of the third complementarity-determining region in the affinity maturation of an antibody," 276(29) J Biol Chem 27622-8 (2001).
Garrard et al., "Fab assembly and enrichment in a monovalent phage display system," 9(12) Biotechnology 1373-7 (1991).
Gram et al., "In vitro selection and affinity maturation of antibodies from a naive combinatorial immunoglobulin library," 89(8) Proc Natl Acad Sci USA 3576-80 (1992).
Hawkins et al., "Selection of phage antibodies by binding affinity: Mimicking affinity maturation," 226(3) J Mol Biol 889-96 (1992).
Lazar et al., "A molecular immunology approach to antibody humanization and functional optimization,"Mol Immunol. 44(8):1986-8 (2007).
Lowman et al., "Selecting high-affinity binding proteins by monovalent phage display," 30(45) Biochemistry 10832-8 (1991).
Lowman & Wells, "Affinity maturation of human growth hormone by monovalent phage display," 234(3) J Mol Biol 564-78 (1993).
McCafferty et al., "Phage antibodies: filamentous phage displaying antibody variable domains," 348(6301) Nature 552-4 (1990).
Morimoto & Inouye, "Single-step purification of F(ab')2 fragments of mouse monoclonal antibodies (immunoglobulins G1) by hydrophobic interaction high performance liquid chromatography using TSKgel Phenyl-5PW ," 24(1-2) J Biochem Biophys Methods 107-17 (1992).
Morrison et al., "Chimeric human antibody molecules: mouse antigen-binding domains with human constant region domains," Proc Natl Acad Sci U S A. 81(21): 6851-6855 (1984).
Padlan, "A possible procedure for reducing the immunogenicity of antibody variable domains while preserving their ligand-binding properties," Mol Immunol. 28(4-5):489-98 (1991).
Pearson & Lipman "Improved tools for biological sequence comparison," 85(8) Proc Natl Acad Sci USA 2444-8 (1988).
Presta et al., "Humanization of an antibody directed against IgE," J Immunol. 151(5):2623-32 (1993).
Rader et al., "A phage display approach for rapid antibody humanization: designed combinatorial V gene libraries," 95(15) Proc Natl Acad Sci USA 8910-15 (1998).
Roguska et al., "Humanization of murine monoclonal antibodies through variable domain resurfacing," Proc Natl Acad Sci U S A. 91(3):969-73 (1994).
Scott & Smith, "Searching for peptide ligands with an epitope library," 249(4967) Science 386-90(1990).
Short et al., "Complementary combining site contact residue mutations of the anti-digoxin Fab 26-10 permit high affinity wild-type binding," 277(19) J Biol Chem 16365-70 (2002).
Sims et al., "A humanized CD18 antibody can block function without cell destruction,"J Immunol. 151(4):2296-308 (1993).
Smith, "Filamentous fusion phage: novel expression vectors that display cloned antigens on the virion surface," 228(4705) Science 1315-7 (1985).
Studnicka et al., "Human-engineered monoclonal antibodies retain full specific binding activity by preserving non-CDR complementarity-modulating residues," Protein Engineering, 7(6):805-814 (1994).
Thompson et al., "Affinity maturation of a high-affinity human monoclonal antibody against the third hypervariable loop of human immunodeficiency virus: use of phage display to improve affinity and broaden strain reactivity," 256(1) J Mol Biol 77-88 (1996).
Thornton et al., "Protein structure. Prediction of progress at last," 354 (6349) Nature 105-6 (1991).
Vaughan et al., "Human antibodies by design," 16(6) Nature Biotechnology 535-9 (1998).
Yang et al., "CDR walking mutagenesis for the affinity maturation of a potent human anti-HIV-1 antibody into the picomolar range," 254(3) J Mol Biol 392-403 (1995).

* cited by examiner

Small sample size rule applied to calculation of summary variable
Source = PKS Study : TDR11407; Scenario: P-X-B-EV-OD, Version 6
Date/Time = 9/13/2016 3:53:43 PM modified on 25/10/2016

Source = PKS Study : TDR11407; Scenario: P-X-B-EV-OD, Version 6
Date/Time = 9/13/2016 3:53:43 PM modified on 25/10/2016

METHOD OF TREATING LUPUS BY ADMINISTERING HUMANIZED ANTI-CXCR5 (C-X-C MOTIF CHEMOKINE RECEPTOR 5) ANTIBODIES

This application claims the benefit of U.S. Provisional Application No. 62/475,173 filed on Mar. 22, 2017, the disclosure of which is explicitly incorporated herein by reference. This application also claims the benefit of European Application No. 17306079.9, filed Aug. 18, 2017.

FIELD OF THE INVENTION

This disclosure relates to anti-CXCR5 antibodies and their use in the amelioration, treatment, or prevention of lupus. The disclosure also relates to prophylactic, immunotherapeutic, and diagnostic compositions comprising an anti-CXCR5 antibody and the use of such anti-CXCR5 antibodies in methods for preventing or treating lupus in mammals, including humans.

BACKGROUND

CXCR5, also known as Burkitt lymphoma receptor (BLR1), CD185, MDR15, and MGC117347, is a G protein-coupled receptor that is a member of the CXC chemokine receptor family. CXCR5 is selectively expressed in recirculating B cells and T follicular helper ($T_{FH}$) cells. CXCR5 has a unique ligand, the CXC chemokine ligand 13 protein (CXCL13), which is constitutively expressed by stromal cells located in the B cell follicles of secondary lymphoid organs, pleural and peritoneal cavities, and in ectopic lymphoid follicles. CXCL13 is one of the most potent B cell chemoattractants and plays a crucial role in attracting CXCR5-expressing cells in these areas. Interactions between T and B cells in follicular areas lead to B cell proliferation and the formation of germinal center (GC) with subsequent B cell maturation, antibody formation, class switching, and affinity maturation.

Systemic lupus erythematosus (SLE) is characterized by the pathological formation of pathogenic autoantibodies against nuclear, cytoplasmic, and/or cell surface molecules, resulting from B and T cell immune dysregulation. Local formation and/or deposition of circulating antigen antibody immune complexes trigger inflammatory responses that are responsible for a wide spectrum of systemic and organ-specific clinical presentations, characterized by remissions and exacerbations, leading to multi-organ system damage and, potentially, end-organ failure.

SUMMARY

The disclosure provides methods for treating a patient having lupus, comprising administering to the patient a therapeutically effective amount of an antibody or fragment thereof that specifically binds to the extracellular domain of human CXCR5, wherein the antibody or fragment thereof comprises:

(a) a light chain variable domain comprising the amino acid sequence of SEQ ID NO: 11, and a heavy chain variable domain comprising the amino acid sequence of SEQ ID NO: 12;

(b) the amino acid sequences of RSSKSLLHSSGKTYLY (SEQ ID NO: 58), RMSNLAS (SEQ ID NO: 59), MQHLEYPYT (SEQ ID NO: 60), GFSLIDYGVN (SEQ ID NO: 61), VIWGDGTTY (SEQ ID NO: 62), and IVY (SEQ ID NO: 63);

(c) a light chain variable domain comprising the amino acid sequence of SEQ ID NO: 13, SEQ ID NO: 14, or SEQ ID NO: 15, and a heavy chain variable domain comprising the amino acid sequence of SEQ ID NO: 16;

(d) the amino acid sequences of RSSKSLLHSSGKTYLY (SEQ ID NO: 58), RLSNLAS (SEQ ID NO: 64), MQHLEYPYT (SEQ ID NO: 60), GFSLIDYGVN (SEQ ID NO: 61), VIWGDGTTY (SEQ ID NO: 62), and IVY (SEQ ID NO: 63);

(e) the amino acid sequences of RSSKSLLHSSGKTYLY (SEQ ID NO: 58), RLSSNLAS (SEQ ID NO: 65), MQHLEYPYT (SEQ ID NO: 60), GFSLIDYGVN (SEQ ID NO: 61), VIWGDGTTY (SEQ ID NO: 62), and IVY (SEQ ID NO: 63);

(f) a variable light chain ($V_L$) comprising the amino acid sequence of SEQ ID NO: 17, SEQ ID NO: 19, or SEQ ID NO: 21, and a variable heavy chain ($V_H$) comprising the amino acid sequence of SEQ ID NO: 23;

(g) a variable light chain comprising the amino acid sequence of SEQ ID NO: 30, SEQ ID NO: 31, or SEQ ID NO: 32, and a variable heavy chain comprising the amino acid sequence of SEQ ID NO: 33 or SEQ ID NO: 34;

(h) the amino acid sequences of RSSKSLLHSSGKTYLY (SEQ ID NO: 58), RMSNLA (SEQ ID NO: 66), MQHLEYPYT (SEQ ID NO: 60), GFSLIDYGVN (SEQ ID NO: 61), VIWGDGTTY (SEQ ID N: 62), and IVY (SEQ ID NO: 63);

(i) the amino acid sequences of RSSKSLLHSSGKTYLY (SEQ ID NO: 58), RLSNLA (SEQ ID NO: 67), MQHLEYPYT (SEQ ID NO: 60), GFSLIDYGVN (SEQ ID NO: 61), VIWGDGTTY (SEQ ID NO: 62), and IVY (SEQ ID NO: 63);

(j) the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63);

(k) a variable light chain comprising the amino acid sequence of SEQ ID NO: 35, and a variable heavy chain comprising the amino acid sequence of SEQ ID NO: 37;

(l) a variable light chain comprising the amino acid sequence of SEQ ID NO: 39, SEQ ID NO: 41, or SEQ ID NO: 43, and a variable heavy chain comprising the amino acid sequence of SEQ ID NO: 45 or SEQ ID NO: 47;

(m) a variable light chain comprising the amino acid sequence of SEQ ID NO: 55, and a variable heavy chain comprising the amino acid sequence of SEQ ID NO: 56 or SEQ ID NO: 57; or (n) the amino acid sequences of RSSKSLLHSSGKTYLYW (SEQ ID NO; 69), RMSNLA (SEQ ID NO: 66), MQHLEYPYT (SEQ ID NO: 60), GFSLIDYGVN (SEQ ID NO: 61), VIWGDGTTY (SEQ ID NO: 62), and IVY (SEQ ID NO: 63); and wherein the patient has tested positive for antinuclear antibody with a titer of ≥1:160.

The disclosure also provides methods of treating a patient having lupus, comprising administering to the patient a therapeutically effective amount of an antibody or fragment thereof that specifically binds to the extracellular domain of human CXCR5, wherein the antibody or fragment thereof comprises a variable light chain comprising the amino acid sequence of SEQ ID NO: 32, and a variable heavy chain comprising the amino acid sequence of SEQ ID NO: 33; and wherein the patient has tested positive for antinuclear antibody with a titer of ≥1:160.

The disclosure also provides methods of treating a patient having lupus, comprising administering to the patient a therapeutically effective amount of an antibody or fragment thereof that specifically binds to the extracellular domain of human CXCR5, wherein the antibody or fragment thereof comprises the amino acid sequences of RSSKSLLHSSGK-TYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63); and wherein the patient has tested positive for antinuclear antibody with a titer of ≥1:160.

Specific embodiments of the disclosure will become evident from the following more detailed description of certain embodiments and the claims.

DETAILED DESCRIPTION

Figure 1:
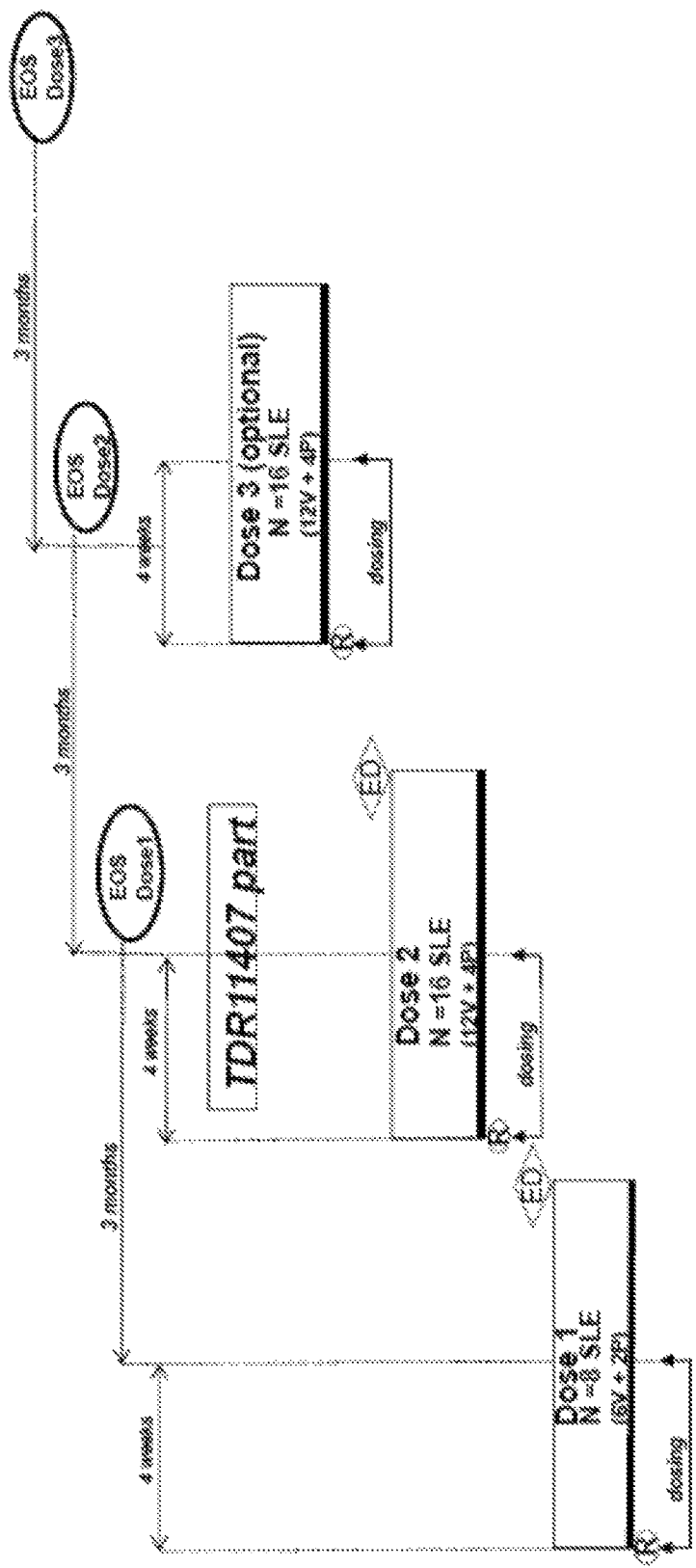
FIG. 1 is a schematic illustrating the study design of the randomized, double-blind, placebo-controlled study of safety, tolerability and pharmacokinetics of repeated ascending subcutaneous (SC) doses of a CXCR5 antibody and pharmacodynamics of a single dose of a CXCR5 antibody in male and female lupus patients. Abbreviations: ED=escalation dose decision; EOS=end-of-study; P=placebo; R=randomization; SLE=systemic lupus erythematosus; V=verum.

This disclosure relates to anti-CXCR5 antibodies and their use in the amelioration, treatment, or prevention of lupus. The disclosure also relates to prophylactic, immunotherapeutic, and diagnostic compositions comprising an anti-CXCR5 antibody and the use of such anti-CXCR5 antibodies in methods for preventing or treating lupus in mammals, including humans.

Standard recombinant DNA methodologies are used to construct the polynucleotides that encode the polypeptides that form the anti-CXCR5 antibodies of the disclosure, incorporate these polynucleotides into recombinant expression vectors, and introduce such vectors into host cells. See e.g., Green and Sambrook, 2012, MOLECULAR CLONING: A LABORATORY MANUAL (Cold Spring Harbor Laboratory Press, 4th ed.). Enzymatic reactions and purification techniques may be performed according to manufacturer's protocols, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

1. General Definitions

As utilized in accordance with the present disclosure, the following terms, unless otherwise indicated, shall be understood to have the following meanings. Unless otherwise required by context, singular terms shall include pluralities and plural terms shall include the singular.

"CXCR5" relates to the naturally occurring, known molecule found on lymphocytes, particularly B cells, and particularly naïve B cells; to such a molecule isolated from such cells; to such a molecule manufactured recombinantly using known materials and means, and using a nucleic acid encoding a CXCR5; as well as to portions of CXCR5, such as the extracellular (EC) domain, which retains the characteristics and properties relevant to the practice of the instant disclosure, such as CXCL13 binding. A soluble CXCR5 molecule can consist essentially of the EC domain of CXCR5, which includes, generally, about the first sixty amino acids of the molecule, that is, the amino terminal portion of CXCR5.

CXCR5 is a non-promiscuous receptor. CXCL13 is a ligand of CXCR5 and is expressed constitutively on stromal cells, such as follicular dendritic cells, and in lymphoid tissues. CXCL13 specifically attracts B cells and a small subset of T cells called B helper follicular T cells (TFH). Moreover, activated T cell induces or upregulate CXCR5 expression. Infiltration of lymphocytes into tertiary, ectopic germinal centers (GCs) has been found to correlate well with increased disease severity and tolerance breakdown in certain disorders which preset with such atypical lymph node-like structures. Using in vivo murine models, such as CXCR5−/− and CXCL13−/− mice, the absence of either the receptor or the ligand results in an altered GC fine architecture due to altered T and B cell localization, and possibly interaction. These mice are also protected against developing severe collagen-induced arthritis (CIA). As CXCR5 is selectively expressed on mature B cells, which are linked to the pathogenesis of RA, blocking this receptor will modulate the arthritogenic response in affected individuals. Rheumatoid arthritis treatment with biologics (i.e., anti-TNFα and anti-CD20 antibodies, Rituximab) has shown to be clinically effective; in particular, patients on B cell-directed therapy have shown long-lasting improvements in clinical signs and symptoms. Selective targeting of CXCR5, which is only expressed on mature B cells and B helper T cells, will not affect B cell development or immunocompromise the patient. Unlike Rituximab, the antibodies disclosed herein are neutralizing antibodies that do not mediate cell cytotoxicity.

A "CXCR5 disease" is a malady, disorder, disease, condition, abnormality, and so on, which is characterized by or caused by overexpression or increased levels of CXCL13 or other CXCR5 ligand, increased levels of B cells, increased levels of B cell activity, increased levels of CXCR5 or improper metabolism and activity of CXCR5.

The term "human CXCR5," "hCXCR5" or "hCXCR5 polypeptide" and similar terms refer to the polypeptides ("polypeptides," "peptides" and "proteins" are used interchangeably herein) disclosed in U.S. Pat. No. 8,647,622, which is incorporated by reference herein in its entirety, and synthesized or isolated from a suitable cell source, and related polypeptides, including SNP variants thereof. Related polypeptides include allelic variants (e.g., SNP variants); splice variants; fragments; derivatives; substitution, deletion, and insertion variants; fusion polypeptides; and interspecies homologs, in some embodiments, which retain CXCR5 activity and/or are sufficient to generate an anti-CXCR5 immune response. Also encompassed are soluble forms of CXCR5 that are sufficient to generate an anti-CXCR5 immunological response. As those skilled in the art will appreciate, an anti-CXCR5 binding agent, such as an antibody, can bind to a CXCR5 polypeptide, polypeptide fragment, antigen, and/or epitope, as an epitope is part of the larger antigen, which is part of the larger polypeptide fragment, which, in turn, is part of the larger polypeptide.

The term "antibody" as used herein refers to a protein that is capable of recognizing and specifically binding to an antigen. Ordinary or conventional mammalian antibodies comprise a tetramer, which is typically composed of two identical pairs of polypeptide chains, each pair consisting of one "light" chain (typically having a molecular weight of about 25 kDa) and one "heavy" chain (typically having a molecular weight of about 50-70 kDa). The terms "heavy chain" and "light chain," as used herein, refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$) and a hinge region between $C_{H1}$ and $C_{H2}$, wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Within full-length light and heavy chains, the variable and constant domains typically are joined by a "J" region of about 12 or more amino acids, with the heavy chain also including a "D" region of about 10 more amino acids. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

As used herein, "anti-CXCR5 antibody" means an antibody or polypeptide derived therefrom (a derivative) which binds specifically to human CXCR5 as defined herein, including, but not limited to, molecules which inhibit or substantially reduce the binding of CXCR5 to its ligands or inhibit CXCR5 activity.

One example of an anti-CXCR5 antibody is SAR113244, which is a potent and specific neutralizing antibody to CXCR5. SAR113244 was engineered in an IgG4 framework containing two amino acid substitutions described to reduce half-molecule formation (S241P) and Fc-mediated effector functions (L248E).

The term "monoclonal antibody" as used herein refers to an antibody obtained from a population of substantially homogeneous antibodies, i.e., the individual antibodies comprising the population are identical except for possible naturally occurring mutations that may be present in minor amounts.

Monoclonal antibodies herein specifically include "chimeric" antibodies in which a portion of the heavy and/or light chain is identical with or homologous to corresponding sequences in antibodies derived from a particular species or belonging to a particular antibody class or subclass (type or subtype), with the remainder of the chain(s) identical with or homologous to corresponding sequences in antibodies derived from another species or belonging to another antibody class or subclass, as well as fragments of such antibodies, so long as they exhibit the desired biological activity of binding to CXCR5 or impacting CXCR5 activity or metabolism (U.S. Pat. No. 4,816,567; Morrison et al., *Proc. Natl. Acad. Sci. U.S.A.* 81(21): 6851-55 (1984)). Thus, CDRs from one class of antibody can be grafted into the FR of an antibody of different class or subclass.

"Humanized" forms of non-human (e.g., murine) antibodies are chimeric immunoglobulins, immunoglobulin chains or fragments thereof (such as $F_v$, $F_{ab}$, $F_{ab'}$, $F_{(ab')2}$ or other target-binding subsequences of antibodies), which contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region ($F_c$), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to CXCR5 or to CXCL13. Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. Such a method is taught herein with respect to substituting "mobile" or "flexible" residues on the antibody molecule, the goal being to reduce or dampen the immunogenicity of the resultant molecule without comprising the specificity of the antibody for its epitope or determinant. See, for example, Studnicka et al., *Protein Eng.* 7(6): 805-14 (1994); Lazar et al., *Mol. Immunol.* 44(6): 1986-98 (2007); Sims et al., *J. Immunol.* 151(4): 2296-308 (1993); Chothia et al., *J. Mol. Biol.* 196(4): 901-17 (1987); Carter et al., *Proc. Natl. Acad. Sci. U.S.A.* 89(10): 4285-89 (1992); Presta et al., *J. Immunol.* 151(5): 2623-32 (1993), International Publication No. WO 2006/042333 and U.S. Pat. No. 5,869,619.

Antibodies can also be humanized by a variety of techniques including CDR grafting (European Publication No. EP 0 239 400; International Publication No. WO 91/09967; and U.S. Pat. Nos. 5,530,101 and 5,585,089), veneering or resurfacing (European Publication Nos. EP 0 592 106 and EP 0 519 596; Padlan, 1991, *Mol. Immunol.* 28(4-5): 489-98; Studnicka et al., *Protein Eng.* 7(6): 805-14 (1994); and Roguska et al., *Proc. Natl. Acad. Sci. U.S.A.* 91(3): 969-73 (1994)) and chain shuffling (U.S. Pat. No. 5,565,332). Human antibodies can be made by a variety of methods known in the art including, but not limited to, phage display methods, see U.S. Pat. Nos. 4,444,887; 4,716,111; 5,545,806; and 5,814,318; and International Publication Nos. WO 98/46645, WO 98/50433, WO 98/24893, WO 98/16654, WO 96/34096, WO 96/33735, and WO 91/10741, using transgenic animals, such as rodents, using chimeric cells, and so on.

The term "antibody fragment" refers to a portion of an intact or a full-length chain or an antibody, generally the target binding or variable region. Examples of antibody fragments include, but are not limited to, $F_{ab}$, $F_{ab'}$, $F_{(ab')2}$ and $F_v$ fragments. A "functional fragment" or "analog of an anti-CXCR5 antibody" is one which can prevent or substantially reduce the ability of the receptor to bind to a ligand or to initiate signaling. As used herein, functional fragment generally is synonymous with, "antibody fragment" and with respect to antibodies, can refer to fragments, such as $F_v$, $F_{ab}$, $F_{(ab')2}$ and so on which can prevent or substantially reduce the ability of the receptor to bind to a ligand or to initiate signaling. An "$F_v$" fragment consists of a dimer of one heavy and one light chain variable domain in a non-covalent association ($V_H$—$V_L$ dimer). In that configuration, the three CDRs of each variable domain interact to define a target binding site on the surface of the $V_H$-$V_L$ dimer, as in an intact antibody. Collectively, the six CDRs confer target binding specificity on the intact antibody. However, even a single variable domain (or half of an $F_v$ comprising only three CDRs specific for a target) can have the ability to recognize and to bind target.

"Single-chain $F_v$," "s$F_v$" or "scAb" antibody fragments comprise the $V_H$ and $V_L$ domains of an antibody, wherein these domains are present in a single polypeptide chain. Generally, the $F_v$ polypeptide further comprises a polypeptide linker, often a flexible molecule, between the $V_H$ and $V_L$ domains, which enables the sFv to form the desired structure for target binding.

The $F_{ab}$ fragment contains the variable and constant domains of the light chain and the variable and first constant domain ($C_{H1}$) of the heavy chain. $F_{ab'}$ fragments differ from $F_{ab}$ fragments by the addition of a few residues at the carboxyl terminus of the $C_{H1}$ domain to include one or more cysteines from the antibody hinge region. $F_{ab'}$ fragments can be produced by cleavage of the disulfide bond at the hinge cysteines of the $F_{(ab')2}$ pepsin digestion product. Additional enzymatic and chemical treatments of antibodies can yield other functional fragments of interest.

The term "antigen" or "target antigen" as used herein refers to a molecule or a portion of a molecule that is capable of being bound by an antibody of the disclosure, and additionally is capable of being used in an animal to produce antibodies capable of binding to an epitope of that antigen. A target antigen may have one or more epitopes. With respect to each target antigen recognized by an antibody, the antibody is capable of competing with an intact antibody that recognizes the target antigen.

The term "epitope" as used herein refers to a region of an antigen that is bound by an antibody of the disclosure. An antibody is said to specifically bind an antigen when it preferentially recognizes its antigen target in a complex mixture of proteins and/or macromolecules. The term "specifically binds," as used herein, refers to the ability of an antibody to bind to an antigen containing an epitope with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or to bind to an epitope with an affinity that is at least two-fold greater than its affinity for a nonspecific antigen.

The term "antigen binding site" as used herein refers to a site in an antibody of the disclosure where an antigen or an epitope binds. The antigen binding site of an antibody is typically described by reference to the CDRs of the antibody.

The phrase "substantially identical" with respect to an antibody chain polypeptide sequence may be construed as an antibody chain exhibiting at least 70%, 80%, 90%, 95%, or more sequence identity to the reference polypeptide sequence. The term with respect to a nucleic acid sequence may be construed as a sequence of nucleotides exhibiting at least about 85%, 90%, 95%, 97%. or more sequence identity to the reference nucleic acid sequence.

The terms "identity" or "homology" may mean the percentage of nucleotide bases or amino acid residues in the candidate sequence that are identical with the residue of a corresponding sequence to which it is compared, after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are available and well known in the art. Sequence identity may be measured using sequence analysis software.

The phrases and terms "functional fragment," "variant," "derivative or analog," and the like, as well as forms thereof, of an antibody or antigen is a compound or molecule having qualitative biological activity in common with a full-length antibody or antigen of interest. For example, a functional fragment or analog of an anti-CXCR5 antibody is one which can bind to a CXCR5 molecule or one which can prevent or substantially reduce the ability of a ligand, such as CXCL13, or an agonistic or antagonistic antibody, to bind to CXCR5. An example is an scFv molecule. As to CXCR5, a variant or derivative thereof is a molecule that is not identical to a naturally occurring CXCR5 and yet can be used for a purpose of the instant disclosure, such as, while not identical to the wild type CXCR5 nevertheless can be used as immunogen to raise antibodies that selectively bind to wild type CXCR5.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

"Antibody homolog" or "homolog" refers to any molecule which specifically binds CXCR5 as taught herein. Thus, an antibody homolog includes native or recombinant antibody, whether modified or not, portions of antibodies that retain the biological properties of interest, such as binding CXCR5, such as an $F_{ab}$ or $F_v$ molecule, a single chain antibody, a polypeptide carrying one or more CDR regions and so on. The amino acid sequence of the homolog need not be identical to that of the naturally occurring antibody but can be altered or modified to carry substitute amino acids, inserted amino acids, deleted amino acids, amino acids other than the twenty normally found in proteins and so on to obtain a polypeptide with enhanced or other beneficial properties.

Antibodies with homologous sequences are those antibodies with amino acid sequences that have sequence homology with the amino acid sequence of a CXCR5 antibody of the present disclosure. Preferably, homology is with the amino acid sequence of the variable regions of an antibody of the present disclosure. "Sequence homology" as applied to an amino acid sequence herein is defined as a sequence with at least about 90%, 91%, 92%, 93%, 94%, or more sequence homology, and more preferably at least about 95%, 96%, 97%, 98%, or 99% sequence homology to another amino acid sequence, as determined, for example, by the FASTA search method in accordance with Pearson et al., *Proc. Nat. Acad. Sci. U.S.A.* 85(8): 2444-48 (1988).

The term "functional equivalents" includes antibodies with homologous sequences, antibody homologs, chimeric antibodies, artificial antibodies and modified antibodies, for example, wherein each functional equivalent is defined by the ability to bind to CXCR5, inhibiting CXCR5 signaling ability or function, or inhibiting binding of CXCL13 and other ligands to CXCR5. The skilled artisan will understand that there is an overlap in the group of molecules termed "antibody fragments" and the group termed "functional equivalents." Methods of producing functional equivalents which retain CXCR5 binding ability are known to the person skilled in the art and are disclosed, for example, in International Publication Nos. WO 93/21319 and WO 89/09622, and European Publication Nos. EP 0 239,400, EP 0 338,745, and EP 0 332,424.

An "isolated" or "purified" antibody is substantially free of cellular material or other contaminating proteins from the cell or tissue source or medium from which the protein is derived, or substantially free of chemical precursors or other chemicals when chemically synthesized. The language "substantially free of cellular material" includes preparations of an antibody in which the polypeptide/protein is separated from cellular components of the cells from which same is isolated or recombinantly produced. Thus, an antibody that is substantially free of cellular material includes preparations of the antibody having less than about 30%, 20%, 10%, 5%, 2.5%, or 1%, (by dry weight) of contaminating protein. When the antibody is recombinantly produced, it is also preferably substantially free of culture medium, i.e., culture medium represents less than about 20%, 10%, 5%, 2.5%, or 1% of the volume of the protein preparation. When antibody is produced by chemical synthesis, it is preferably substantially free of chemical precursors or other chemicals and reagents, i.e., the antibody of interest is separated from chemical precursors or other chemicals which are involved in the synthesis of the protein. Accordingly, such preparations of the antibody have less than about 30%, 20%, 10%, 5%, or 1% (by dry weight) of chemical precursors or compounds other than antibody of interest. In one embodiment of the present disclosure, antibodies are isolated or purified.

"Antagonist" refers to a molecule capable of inhibiting one or more biological activities of a target molecule, such as signaling by CXCR5. Antagonists may interfere with the binding of a receptor to a ligand and vice versa, by incapacitating or killing cells activated by a ligand, and/or by interfering with receptor or ligand activation (e.g., tyrosine kinase activation) or signal transduction after ligand binding to a receptor. The antagonist may completely block receptor-ligand interactions or may substantially reduce such interactions. All such points of intervention by an antagonist shall be considered equivalent for purposes of the instant disclosure. Thus, included within the scope of the disclosure are antagonists (e.g., neutralizing antibodies) that bind to CXCR5, CXCL13 or other ligands of CXCR5, or a complex of CXCR5 and a ligand thereof, such as CXCL13; amino acid sequence variants or derivatives of CXCR5 or CXCL13 which antagonize the interaction between CXCR5 and a ligand, such as CXCL13; soluble CXCR5, optionally fused to a heterologous molecule such as an immunoglobulin region (e.g., an immunoadhesin); a complex comprising CXCR5 in association with another receptor or biological molecule; synthetic or native sequence peptides which bind to CXCR5; and so on.

"Agonist" refers to a compound, including a protein, a polypeptide, a peptide, an antibody, an antibody fragment, a conjugate, a large molecule, a small molecule, which activates one or more biological activities of CXCR5. Agonists may interact with the binding of a receptor to a ligand and vice versa, by acting as a mitogen of cells activated by a ligand, and/or by interfering with cell inactivation or signal transduction inhibition after ligand binding to a receptor. All such points of intervention by an agonist shall be considered equivalent for purposes of the instant invention. Thus, included within the scope of the disclosure are agonists that bind to CXCR5, CXCL13 or other ligand of CXCR5, or a complex of CXCR5 and a ligand thereof, such as CXCL13; amino acid sequence variants or derivatives of CXCR5 or CXCL13 which facilitate the interaction between CXCR5 and a ligand, such as CXCL13; soluble CXCR5, optionally fused to a heterologous molecule such as an immunoglobulin region (e.g., an immunoadhesin); a complex comprising CXCR5 in association with another receptor or biological molecule; synthetic or native sequence peptides which bind to CXCR5; and so on. The agonist generally is an entity which directly activates CXCR5, for example, to signal.

The terms "cell," "cell line," and "cell culture" include progeny thereof. It is also understood that all progeny may not be precisely identical, such as in DNA content, due to deliberate or inadvertent mutation. Variant progeny that have the same function or biological property of interest, as screened for in the original cell, are included. The "host cells" used in the present disclosure generally are prokaryotic or eukaryotic hosts, selected as a design choice.

"Transformation" of a cellular organism, cell, or cell line with a nucleic acid means introducing a nucleic acid into the target cell so that the nucleic acid is replicable, either as an extrachromosomal element or by chromosomal integration, and, optionally, expressed. "Transfection" of a cell or organism with a nucleic acid refers to the taking up of the nucleic acid, e.g., an expression vector, by the cell or organism whether or not any coding sequences are in fact expressed. The terms "transfected host cell" and "transformed" refer to a cell in which a nucleic acid was introduced. Typical prokaryotic host cells include various strains of *E. coli*. Typical eukaryotic host cells are mammal cells, such as Chinese hamster ovary, or cells of human origin. The introduced nucleic acid sequence may be from the same species as the host cell or of a different species from the host cell, or may be a hybrid nucleic acid sequence, containing some foreign and some homologous nucleic acids. Transformation can also occur by transduction or infection with virus-derived elements.

The term "vector" means a nucleic acid construct, a carrier, containing a nucleic acid, the transgene, the foreign gene or the gene of interest, which can be operably linked to suitable control sequences for expression of the transgene in a suitable host. Such control sequences include, for example, a promoter to effect transcription, an optional operator sequence to control such transcription, a sequence encoding suitable mRNA ribosome binding sites and sequences which control the termination of transcription and translation. The vector may be a plasmid, a phage particle or just a potential genomic insert. Once transformed into a suitable host, the vector may replicate and function independently of the host genome, or may in some instances, integrate into the host cell genome. In the present specification, "plasmid" and "vector" are used interchangeably, as the plasmid is a commonly used form of vector. However, the disclosure is intended to include such other forms of vectors which serve equivalent carrier function as and which are, or become, known in the art, such as viruses, synthetics molecules that carry nucleic acids, liposomes and the like.

"Mammal" for purposes of treatment refers to any animal classified as a mammal, including human, domestic and farm animals, nonhuman primates, and zoo, sports or pet animals, such as dogs, horses, cats, cows, etc.

The term "patient" as used herein includes human and animal subjects.

A "disorder" is any condition that would benefit from treatment using the antibodies of the disclosure. "Disorder" and "condition" are used interchangeably herein and include chronic and acute disorders or diseases, including those pathological conditions that predispose a patient to the disorder in question.

The term "lupus" as used refers to all types and manifestations of lupus. For example, manifestations of lupus include systemic lupus erythematosus; lupus nephritis; cutaneous manifestations (e.g., manifestations seen in cutaneous lupus erythematosus, e.g., a skin lesion or rash); CNS lupus; cardiovascular, pulmonary, hepatic, haematological, gastrointestinal and musculoskeletal manifestations; neonatal lupus erythematosus; childhood systemic lupus erythematosus; drug-induced lupus erythematosus; anti-phospholipid syndrome; and complement deficiency syndromes resulting in lupus manifestations.

The terms "treatment" or "treat" as used herein refer to both therapeutic treatment and prophylactic or preventative measures. Those in need of treatment include those having the disorder as well as those prone to have the disorder or those in which the disorder is to be prevented. In particular embodiments, the antibodies can be used to treat lupus.

The terms "pharmaceutical composition" or "therapeutic composition" as used herein refer to a compound or composition capable of inducing a desired therapeutic effect when properly administered to a patient. One embodiment of the disclosure provides a pharmaceutical composition comprising a pharmaceutically acceptable carrier and a therapeutically effective amount of at least one antibody of the disclosure.

The term "pharmaceutically acceptable carrier" or "physiologically acceptable carrier" as used herein refers to one or more formulation materials suitable for accomplishing or enhancing the delivery of one or more antibodies of the disclosure.

The terms "effective amount" and "therapeutically effective amount" when used in reference to a pharmaceutical composition comprising one or more antibodies of the disclosure refer to an amount or dosage sufficient to produce a desired therapeutic result. More specifically, a therapeutically effective amount is an amount of an antibody sufficient to inhibit, for some period of time, one or more of the clinically defined pathological processes associated with the condition being treated. The effective amount may vary depending on the specific antibody that is being used, and may also depend on a variety of factors and conditions related to the patient being treated and the severity of the disorder. For example, if the antibody is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is within the ability of those skilled in the art.

2. CXCR5 Antibodies

In some embodiments the antibody is an isolated antibody or fragment thereof that specifically binds to the extracellular domain of human CXCR5. The antibody or fragment thereof can include: (a) a light chain variable domain comprising the amino acid sequence of SEQ ID NO: 11, and a heavy chain variable domain comprising the amino acid sequence of SEQ ID NO: 12; (b) the amino acid sequences of RSSKSLLHSSGKTYLY (SEQ ID NO: 58), RMSNLAS (SEQ ID NO: 59), MQHLEYPYT (SEQ ID NO: 60), GFSLIDYGVN (SEQ ID NO: 61), VIWGDGTTY (SEQ ID NO: 62), and IVY (SEQ ID NO: 63); (c) a light chain variable domain comprising the amino acid sequence of SEQ ID NO: 13, SEQ ID NO: 14, or SEQ ID NO: 15, and a heavy chain variable domain comprising the amino acid sequence of SEQ ID NO: 16; (d) the amino acid sequences of RSSKSLLHSSGKTYLY (SEQ ID NO: 58), RLSNLAS (SEQ ID NO: 64), MQHLEYPYT (SEQ ID NO: 60), GFSLIDYGVN (SEQ ID NO: 61), VIWGDGTTY (SEQ ID NO: 62), and IVY (SEQ ID NO: 63); (e) the amino acid sequences of RSSKSLLHSSGKTYLY (SEQ ID NO: 58), RLSSNLAS (SEQ ID NO: 65), MQHLEYPYT (SEQ ID NO: 60), GFSLIDYGVN (SEQ ID NO: 61), VIWGDGTTY (SEQ ID NO: 62), and IVY (SEQ ID NO: 63); (f) a variable light chain (VL) comprising the amino acid sequence of SEQ ID NO: 17, SEQ ID NO: 19, or SEQ ID NO: 21, and a variable heavy chain (VH) comprising the amino acid sequence of SEQ ID NO: 23; (g) a variable light chain comprising the amino acid sequence of SEQ ID NO: 30, SEQ ID NO: 31, or SEQ ID NO: 32, and a variable heavy chain comprising the amino acid sequence of SEQ ID NO: 33 or SEQ ID NO: 34; (h) the amino acid sequences of RSSKSLLHSSGKTYLY (SEQ ID NO: 58), RMSNLA (SEQ ID NO: 66), MQHLEYPYT (SEQ ID NO: 60), GFSLIDYGVN (SEQ ID NO: 61), VIWGDGTTY (SEQ ID N: 62), and IVY (SEQ ID NO: 63); (i) the amino acid sequences of RSSKSLLHSSGKTYLY (SEQ ID NO: 58), RLSNLA (SEQ ID NO: 67), MQHLEYPYT (SEQ ID NO: 60), GFSLIDYGVN (SEQ ID NO: 61), VIWGDGTTY (SEQ ID NO: 62), and IVY (SEQ ID NO: 63); (j) the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63); (k) a variable light chain comprising the amino acid sequence of SEQ ID NO: 35, and a variable heavy chain comprising the amino acid sequence of SEQ ID NO: 37; (l) a variable light chain comprising the amino acid sequence of SEQ ID NO: 39, SEQ ID NO: 41, or SEQ ID NO: 43, and a variable heavy chain comprising the amino acid sequence of SEQ ID NO: 45 or SEQ ID NO: 47; (m) a variable light chain comprising the amino acid sequence of SEQ ID NO: 55, and a variable heavy chain comprising the amino acid sequence of SEQ ID NO: 56 or SEQ ID NO: 57; or (n) the amino acid sequences of RSSKSLLHSSGKTYLYW (SEQ ID NO: 69), RMSNLA (SEQ ID NO: 66), MQHLEYPYT (SEQ ID NO: 60), GFSLIDYGVN (SEQ ID NO: 61), VIWGDGTTY (SEQ ID NO: 62), and IVY (SEQ ID NO: 63).

In another embodiment, the antibody or fragment thereof comprises a variable light chain comprising the amino acid sequence of SEQ ID NO: 32, and a variable heavy chain comprising the amino acid sequence of SEQ ID NO: 33. In another embodiment, the antibody or fragment thereof comprises a variable light chain comprising the amino acid sequence of SEQ ID NO: 70, and a variable heavy chain comprising the amino acid sequence of SEQ ID NO: 33.

In another embodiment, the antibody or fragment thereof comprises the amino acid sequences of RSSKSLLHSSGK-TYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63).

The antibody or fragment thereof can further include one or more constant regions. The one or more constant regions domains can consist of $C_{H1}$, $C_{H2}$, $C_{H3}$, and/or $C_L$. The one or more constant regions can be from an IgG antibody, which can be, for example, an IgG4 antibody. The antibody or fragment thereof can be a single chain Fv.

Antibodies of the instant disclosure may also be described or specified in terms of cross-reactivity. Antibodies that bind CXCR5 polypeptides, which have at least 95%, at least 90%, at least 85%, at least 80%, at least 75%, at least 70%, at least 65%, at least 60%, at least 55%, and at least 50% identity (as calculated using methods known in the art and described herein) to CXCR5 are also included in the instant disclosure.

Antibodies of the instant disclosure also may be described or specified in terms of binding affinity to a CXCR5 of interest. Anti-CXCR5 antibodies may bind with a $K_D$ of less than about $10^{-7}$ M, less than about $10^{-6}$ M, or less than about $10^{-5}$ M. Higher binding affinities in an antibody of interest can be beneficial, such as those with an equilibrium dissociation constant or $K_D$ of from about $10^{-8}$ to about $10^{-15}$ M, from about $10^{-8}$ to about $10^{-12}$ M, from about $10^{-9}$ to about $10^{-11}$ M, or from about $10^{-8}$ to about $10^{-10}$ M. The disclosure also provides antibodies that competitively inhibit binding of an antibody to an epitope of the disclosure as determined by any method known in the art for determining competitive binding, for example, the immunoassays described herein. In some embodiments, the antibody competitively inhibits binding to the epitope by at least 95%, at least 90%, at least 85%, at least 80%, at least 75%, at least 70%, at least 60%, or at least 50%.

A variant antibody or mutant, or mutein is one wherein one or more amino acid residues are altered, for example, in one or more of the hypervariable regions of the antibody. Alternatively, or in addition, one or more alterations (e.g., substitutions) of framework residues may be introduced in the antibody where this results in an improvement in the binding affinity of the antibody mutant for CXCR5. Examples of framework region residues that can be modified include those which non-covalently bind antigen directly (Amit et al., *Science* 233(4765): 747-53 (1986)); interact with/affect the conformation of a CDR (Chothia et al., *J. Mol. Biol.* 196(4): 901-17 (1987)); and/or participate in the $V_L$-$V_H$ interface (European Publication No. EP 0 239 400). In certain embodiments, modification of one or more of such framework region residues results in an enhancement of the binding affinity of the antibody for the cognate antigen. For example, from about one to about five framework residues may be altered in this embodiment of the disclosure. Sometimes, this may be sufficient to yield an antibody mutant suitable for use in preclinical trials, even where none of the hypervariable region residues have been altered. Normally, however, the antibody mutant can comprise one or more hypervariable region alteration(s). The constant regions also can be altered to obtain desirable or more desirable effector properties.

The hypervariable region residues which are altered may be changed randomly, especially where the starting binding affinity of the parent antibody is such that randomly-produced antibody mutants can be readily screened for altered binding in an assay as taught herein.

One procedure for obtaining antibody mutants, such as CDR mutants, is "alanine scanning mutagenesis" (Cunningham et al., *Science* 244(4908): 1081-85 (1989)). One or more of the hypervariable region residue(s) are replaced by alanine or polyalanine residue(s). Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. Similar substitutions can be attempted with other amino acids, depending on the desired property of the scanned residues.

A more systematic method for identifying amino acid residues to modify comprises identifying hypervariable region residues involved in binding CXCR5 and those hypervariable region residues with little or no involvement with CXCR5 binding. An alanine scan of the non-binding hypervariable region residues is performed, with each ala mutant tested for enhancing binding to CXCR5. In another embodiment, those residue(s) significantly involved in binding CXCR5 are selected to be modified. Modification can involve deletion of a residue or insertion of one or more residues adjacent to a residue of interest. However, normally the modification involves substitution of the residue by another amino acid. A conservative substitution can be a first substitution. If such a substitution results in a change in biological activity (e.g., binding affinity), then another conservative substitution can be made to determine if more substantial changes are obtained.

Even more substantial modification in an antibody range and presentation of biological properties can be accomplished by selecting an amino acid that differs more substantially in properties from that normally resident at a site. Thus, such a substitution can be made while maintaining: (a) the structure of the polypeptide backbone in the area of the substitution, for example, as a sheet or helical conformation; (b) the charge or hydrophobicity of the molecule at the target site, or (c) the bulk of the side chain.

For example, the naturally occurring amino acids can be divided into groups based on common side chain properties:

(1) hydrophobic: methionine (M or met), alanine (A or ala), valine (V or val), leucine (L or leu) and isoleucine (I or ile);

(2) neutral, hydrophilic: cysteine (C or cys), serine (S or ser), threonine (T or thr), asparagine (N or asn) and glutamine (Q or gln);

(3) acidic: aspartic acid (D or asp) and glutamic acid (E or glu);

(4) basic: histidine (H or his), lysine (K or lys) and arginine (R or arg);

(5) residues that influence chain orientation: glycine (G or gly) and proline (P or pro), and (6) aromatic: tryptophan (W or trp), tyrosine (Y or tyr) and phenylalanine (F or phe).

Non-conservative substitutions can entail exchanging an amino acid with an amino acid from another group. Conservative substitutions can entail exchange of one amino acid for another within a group.

Preferred amino acid substitutions include those which: (1) reduce susceptibility to proteolysis, (2) reduce susceptibility to oxidation, (3) alter binding affinity and (4) confer or modify other physico-chemical or functional properties of such analogs. Analogs can include various muteins of a sequence other than the naturally occurring peptide sequence. For example, single or multiple amino acid substitutions (preferably conservative amino acid substitutions) may be made in the naturally-occurring sequence (preferably in the portion of the polypeptide outside the domains) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence) unless of a change in the bulk or conformation of the R group or side chain, "Proteins, Structures and Molecular Principles" (Creighton, ed., W. H. Freeman and Company, New York (1984)); "Introduction to Protein Structure" (Branden & Tooze, eds., Garland Publishing, New York, N.Y. (1991)); and Thornton et al., *Nature* 354(6349): 105-06 (1991).

Ordinarily, the antibody mutant with improved biological properties will have an amino acid sequence having at least 75% amino acid sequence identity or similarity with the amino acid sequence of either the heavy or light chain variable domain of the parent anti-human CXCR5 antibody, at least 80%, at least 85%, at least 90% and often at least 95% identity. Identity or similarity with respect to parent antibody sequence is defined herein as the percentage of amino acid residues in the candidate sequence that are identical (i.e., same residue) or similar (i.e., amino acid residue from the same group based on common side-chain properties, supra) with the parent antibody residues, after aligning the sequences and introducing gaps, if necessary, to achieve the maximum percent sequence identity.

Alternatively, antibody mutants can be generated by systematic mutation of the FR and CDR regions of the heavy and light chains, or the $F_c$ region of the anti-CXCR5 antibody. Another procedure for generating antibody mutants involves the use of affinity maturation using phage display (Hawkins et al., *J. Mol. Biol.* 226(3): 889-96 (1992), and Lowman et al., *Biochemistry* 30(45): 10832-38 (1991)). Bacteriophage coat-protein fusions (Smith, *Science* 228 (4705): 1315-17 (1985); Scott et al., *Science* 249(4967): 386-90 (1990); Cwirla et al., *Proc. Natl. Acad. Sci. U.S.A.* 87(16): 6378-82 (1990); Devlin et al., *Science* 249(4967): 404-06 (1990); and U.S. Pat. No. 5,223,409) are known to be useful for linking the phenotype of displayed proteins or peptides to the genotype of bacteriophage particles which encode them. The $F_{ab}$ domains of antibodies have also been displayed on phage (McCafferty et al., *Nature* 348(6301): 552-54 (1990); Barbas et al., *Proc. Natl. Acad. Sci. U.S.A.* 88(18): 7978-82 (1991); and Garrard et al., *Biotechnology (NY)* 9(12): 1373-77 (1991)).

Monovalent phage display consists of displaying a set of protein variants as fusions of a bacteriophage coat protein on phage particles (Bass et al., *Proteins* 8(4): 309-14 (1990). Affinity maturation, or improvement of equilibrium binding affinities of various proteins, has previously been achieved through successive application of mutagenesis, monovalent phage display and functional analysis (Lowman et al., *J. Mol. Biol.* 234(3): 564-78 (1993); and U.S. Pat. No. 5,534,617), for example, by focusing on the CDR regions of antibodies (Barbas et al., *Proc. Natl. Acad. Sci. U.S.A.* 91(9): 3809-13 (1994); and Yang et al., *J. Mol. Biol.* 254(3):392-403 (1995)).

Libraries of many (for example, $10^6$ or more) protein variants, differing at defined positions in the sequence, can be constructed on bacteriophage particles, each of which contains DNA encoding the particular protein variant. After cycles of affinity purification, using an immobilized antigen, individual bacteriophage clones are isolated, and the amino acid sequence of the displayed protein is deduced from the DNA.

Following production of the antibody mutant, the biological activity of that molecule relative to the parent antibody can be determined as taught herein. That may involve determining the binding affinity and/or other biological activities or physical properties of the antibody. In one embodiment, a panel of antibody mutants are prepared and are screened for binding affinity for the antigen. One or more of the antibody mutants selected from the screen are optionally subjected to one or more further biological activity assays to confirm that the antibody mutant(s) have new or improved properties. In other embodiments, the antibody mutant retains the ability to bind CXCR5 with a binding affinity similar to or better/higher than that of the parent antibody.

The antibody mutant(s) so selected may be subjected to further modifications, often depending on the intended use of the antibody. Such modifications may involve further alteration of the amino acid sequence, fusion to heterologous polypeptide(s) and/or covalent modifications. For example, a cysteine residue not involved in maintaining the proper conformation of the antibody mutant may be substituted, generally with serine, to improve the oxidative stability of the molecule and to prevent aberrant cross-linking. Conversely, a cysteine may be added to the antibody to improve stability (particularly where the antibody is an antibody fragment such as an $F_v$ fragment).

Functional equivalents may be produced by interchanging different CDRs of different antibody chains within a framework or a composite FR derived from plural antibodies. Thus, for example, different classes of antibody are possible for a given set of CDRs by substitution of different heavy chains, for example, $IgG_{1-4}$, IgM, $IgA_{1-2}$ or IgD, to yield differing CXCR5 antibody types and isotypes. Similarly, artificial antibodies within the scope of the disclosure may be produced by embedding a given set of CDRs within an entirely synthetic framework.

The CDRs generally are of importance for epitope recognition and antibody binding. However, changes may be made to residues that comprise the CDRs without interfering with the ability of the antibody to recognize and to bind the cognate epitope. For example, changes that do not impact epitope recognition, yet increase the binding affinity of the antibody for the epitope, may be made. Several studies have surveyed the effects of introducing one or more amino acid changes at various positions in the sequence of an antibody, based on the knowledge of the primary antibody sequence, on the properties thereof, such as binding and level of expression (Yang et al., *J. Mol. Biol.* 254(3): 392-403 (1995); Rader et al., *Proc. Natl. Acad. Sci. U.S.A.* 95(15): 8910-15 (1998); and Vaughan et al., *Nat. Biotechnol.* 16(6): 535-39 (1998)).

Thus, equivalents of an antibody of interest can be generated by changing the sequences of the heavy and light chain genes in the CDR1, CDR2 or CDR3, or framework regions, using methods such as oligonucleotide-mediated site-directed mutagenesis, cassette mutagenesis, error-prone PCR, DNA shuffling or mutator-strains of *E. coli* (Vaughan et al., *Nat. Biotechnol.* 16(6): 535-39 (1998); and Adey et al., 1996, Chap. 16, pp. 277-91, in "Phage Display of Peptides and Proteins," eds. Kay et al., Academic Press). The methods of changing the nucleic acid sequence of the primary antibody can result in antibodies with improved affinity (Gram et al., *Proc. Natl. Acad. Sci. U.S.A.* 89(8): 3576-80 (1992); Boder et al., *Proc. Natl. Acad. Sci. U.S.A.* 97(20): 10701-05 (2000); Davies et al., *Immunotechnology* 2(3): 169-79 (1996); Thompson et al., *J. Mol. Biol.* 256(1): 77-88 (1996); Short et al., *J. Biol. Chem.* 277(19): 16365-70 (2002); and Furukawa et al., *J. Biol. Chem.* 276(29): 27622-28 (2001)).

To determine whether a particular antibody homolog binds to human CXCR5, any conventional binding assay may be used. Useful CXCR5 binding assays include FACS analysis, ELISA assays, radioimmunoassays and the like, which detect binding of antibody, and functions resulting therefrom, to human CXCR5. Full-length and soluble forms of human CXCR5 taught herein are useful in such assays. The binding of an antibody or homolog to CXCR5, or to soluble fragments thereof, may conveniently be detected through the use of a second antibody specific for immunoglobulins of the species from which the antibody or homolog is derived.

To determine whether a particular antibody or homolog does or does not significantly block binding of CXCL13 or other ligand to human CXCR5, any suitable competition assay may be used. Useful assays include, for example, ELISA assays, FACS assays, radioimmunoassays and the like that quantify the ability of the antibody or homolog to compete with CXCL13 or other ligand for binding to human CXCR5. Preferably, the ability of ligand to block binding of labeled human CXCR5 to immobilized antibody or homolog is measured.

The ability of an antibody or homolog to bind to human CXCR5 can be evaluated by testing the ability thereof to bind to human $CXCR5^+$ cells. Suitable $CXCR5^+$ cells for use in determining whether a particular antibody or homolog binds to human CXCR5 are mammal tissue culture cells transformed with DNA encoding full-length human CXCR5 and expressing the CXCR5 on the cell surface or B cell lines.

Binding of the antibody or homolog to the $CXCR5^+$ cell can be detected by staining the cells with a fluorescently-labeled second antibody specific for immunoglobulins of the same species from which the antibody homolog being tested is derived. A fluorescence activated cell sorter ("FACS") can be used to detect and to quantify any binding, see generally, Shapiro, "Practical Flow Cytometry," Alan R. Liss, Inc., New York, N.Y. (1985).

Also, the ability of an antibody homolog to block binding of a ligand, such as CXCL13, to human CXCR5 can be determined by preincubating excess ligand with $CXCR5^+$ cells and quantifying the degree to which the bound ligand blocks binding of the antibody or homolog to the cells. Binding of the antibody homolog to the $CXCR5^+$ cells can be quantified by FACS analysis, using a fluorescently labeled second antibody specific for immunoglobulins of the same species from which the antibody homolog being tested is derived. Alternatively, a competition assay can be configured using labeled ligand or antibody as known in the art.

Antibody fragments which recognize specific epitopes may be generated by known techniques. Traditionally, these fragments were derived via proteolytic digestion of intact antibodies (see, e.g., Morimoto et al., *J. Biochem. Biophys. Methods* 24(102): 107-17 (1992); and Brennan et al., *Science* 229(4708): 81-83 (1985)). For example, $F_{ab}$ and $F_{(ab')2}$ fragments of the disclosure may be produced by proteolytic cleavage of immunoglobulin molecules, using enzymes such as papain (to produce $F_{ab}$ fragments) or pepsin (to produce $F_{(ab')2}$ fragments). $F_{(ab')2}$ fragments contain the variable region, the light chain constant region and the constant region $C_{H1}$ domain of the heavy chain. However, those fragments can be produced directly by recombinant host cells. For example, the antibody fragments can be isolated from an antibody phage library. Alternatively, $F_{(ab')2}$-SH fragments can be directly recovered from *E. coli* and chemically coupled to form F(ab')$_2$ fragments (Carter et al., *Biotechnology* (N Y) 10(2): 163-67 (1992)). According to another approach, $F_{(ab')2}$ fragments can be isolated directly from recombinant host cell culture. Other techniques for the production of antibody fragments will be apparent to the skilled practitioner. In other embodiments, the antibody of choice is a single chain $F_v$ fragment ($F_v$) (International Publication No. WO 93/16185).

3. Antibody Therapeutic Compositions and Administration Thereof

Therapeutic or pharmaceutical compositions comprising one or more antibodies of the disclosure for treatment of lupus are within the scope of the disclosure. Such therapeutic or pharmaceutical compositions can comprise a therapeutically effective amount of an antibody-drug conjugate, in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the antibodies of the disclosure.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the disclosure, antibody compositions can be prepared for storage by mixing the selected composition having the desired degree of purity with optional formulation agents in the form of a lyophilized cake or an aqueous solution. Further, the antibody can be formulated as a lyophilizate using appropriate excipients such as sucrose.

The pharmaceutical compositions of the disclosure can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this disclosure can be in the form of a pyrogen-free, parenterally acceptable, aqueous solution comprising the desired antibody in a pharmaceutically acceptable vehicle. A particularly suitable vehicle for parenteral injection is sterile distilled water in which an antibody of the disclosure is formulated as a sterile, isotonic solution, properly preserved. Yet another preparation can involve the formulation of the antibody with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the antibody include implantable drug delivery devices.

In one embodiment, a pharmaceutical composition can be formulated for inhalation. For example, an antibody can be formulated as a dry powder for inhalation. Inhalation solutions containing an antibody can also be formulated with a propellant for aerosol delivery. In yet another embodiment, solutions can be nebulized.

It is also contemplated that certain formulations can be administered orally. In one embodiment of the disclosure, antibodies that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the antibody. Diluents, flavorings, low melting point waxes, vegetable oils, lubricants, suspending agents, tablet disintegrating agents, and binders can also be employed.

Another pharmaceutical composition can involve an effective quantity of an antibody in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions of the disclosure will be evident to those skilled in the art, including formulations involving antibodies in sustained- or controlled-delivery formulations. Techniques for formulating a variety of other sustained- or controlled-delivery means, such as liposome carriers, bio-erodible microparticles, or porous beads and depot injections, are also known to those skilled in the art. Additional examples of sustained-release preparations include semipermeable polymer matrices in the form of shaped articles, e.g., films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(−)-3-hydroxybutyric acid. Sustained-release compositions can also include liposomes, which can be prepared by any of several methods known in the art.

Pharmaceutical compositions of the disclosure to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of pharmaceutical composition containing an antibody to be employed therapeutically will depend, for example, upon the therapeutic context and objectives. One skilled in the art will appreciate that the appropriate dosage levels for treatment will thus vary depending, in part, upon the molecule delivered, the indication for which the antibody is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 200 mg to 500 mg.

Dosing frequency will depend upon the pharmacokinetic parameters of the antibody in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by subcutaneous, intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

The Examples that follow are illustrative of specific embodiments of the disclosure, and various uses thereof. They are set forth for explanatory purposes only, and should not be construed as limiting the scope of the disclosure in any way.

Example 1

Investigational Plan

Description of Overall Study and Design Plan

This was a single-center, double-blind, randomized, placebo-controlled study of sequential repeated ascending doses of SAR113244 in lupus patients.

The total duration per patient from screening to the end-of-study (EOS) visit was up to 20 weeks including:

Screening: within 4 weeks.

Observation phase from the first investigational product administration to the last assessment: 112 days (i.e., 84 days from last dose) including 2 treatment days within 4 weeks.

EOS visit: Day 113.

Poststudy observation: on Day 226 for anti-drug antibodies (ADA) assessment (for patients with positive ADA at the EOS only).

The dose escalation was designed to progress from the first dose to the highest dose up to the occurrence of relevant events supporting maximum tolerated dose determination, e.g., Number of adverse events (AEs) with severity/intensity high enough for a meaningful decision Proportion of AEs of the same type high enough to justify the decision The dose escalation was to be stopped as soon as consequences regarding patient protection or non-acceptable risks were identified or anticipated. The severity rating was to be adapted to SLE patients taking into account event characteristics: type, deleterious potential, occurrence, progression, and monitorability. A unique serious AE occurrence was not by itself a criterion for taking a decision (assessment depends on the nature of the reported event).

A decision to proceed from dose 'n' to the next higher 'n+1' dose level group was to be determined based on a preliminary blinded safety report: Up to at least 28 days after the second dose of at least 6 of 8 patients (Cohort 1) or 12 of 16 patients (Cohorts 2 or 3) in dose level cohort 'n', including at least 1 placebo in Cohort 1.

Discussion of Study Design and Choice of Control Groups

This double-blind, randomized, placebo-controlled SC multiple ascending dose study design was well established for a phase I dose escalation study and considered appropriate to assess safety, tolerability, and preliminary pharmacokinetic (PK) and pharmacodynamic (PD) (Buoen et al., *J. Clin. Pharmacol.* 45(10): 1123-36 (2005)).

Patients were institutionalized for 2 days at the time of each SAR113244 administration (i.e., the evening before the dosing day and up to the day after). The administration of the investigational product to each patient of Cohort 1 was staggered so that no more than 1 patient per week was dosed for the first 2 weeks. The third patient of the group was dosed no sooner than the following week (Week 3), which was at least 1 day prior to dosing the remainder of the group, i.e., 1:1:1:5. In addition, patients were randomized so that no more than 1 out of the 4 first patients received placebo. Dosing was not staggered in Cohort 2.

Selection of Study Population

Patients were included in the study according to the following criteria.

Inclusion Criteria

Demography

I 01. Male or female patients, between 18 and 75 years of age, inclusive.

I 02. Body mass index ≥18.0 and <35.0 kg/m$^2$.

Health Status

I 03. Fulfils American College of Rheumatology or Systemic Lupus International Collaborating Clinics classification criteria for SLE for at least 6 months.

I 04. Patient with mild-to-moderate active SLE: Safety of Estrogens in Lupus Erythematosus National Assessment-Systemic lupus erythematosus disease activity index (SELENA-SLEDAI) score in the range of 2 to 9, inclusive.

I 05. Female patients using a highly effective contraceptive method of birth control approved by health authority for up to at least 3 months after last dose and a negative pregnancy test result. If patients are unwilling and unable to be tested for pregnancy, include only if postmenopausal for more than 12 months or sterilized for more than 3 months. For male patients with partner(s) of childbearing potential (including lactating women), using a double contraception method according to the following algorithm: (condom) plus (intra-uterine device or hormonal contraceptive) from the inclusion up to 2 months after the last dosing.

I 06. Presence of at least 1 of the following serological markers of autoantibody production at screening:

Antinuclear antibodies (ANA) ≥1:160.

Anti-double stranded (ds) DNA antibodies ≥2× lowest positive level.

Regulations

I 07. Had given written informed consent prior to undertaking any study-related procedure.

I 08. Covered by a health insurance system where applicable, and/or in compliance with the recommendations of the national laws in force relating to biomedical research.

I 09. Not under any administrative or legal supervision.

Exclusion Criteria

Medical History and Clinical Status

E 01. Unstable or severe manifestation of SLE based on clinical judgment at entry, that, in the opinion of the investigator was likely to require initiation or changes to baseline concomitant medications, particularly high dose glucocorticoids and/or prohibited immunosuppressive medications (see E 22 criterion), during the course of the study or hospitalization within the 30 days prior to screening, except for minor surgery.

E 02. Active or chronic, severe neuropsychiatric lupus:
Uncontrolled seizure disorder.
Acute confusional state (delirium) or organic mental syndrome.
Psychosis.

E 03. Severe active lupus nephritis or chronic renal insufficiency:
Requiring current treatment with cyclophosphamide.
Active sediment on urinalysis (red blood cell casts, hematuria due to SLE).
Urine protein: creatinine ratio >2 mg/mL.
Estimated creatinine clearance ≤50 mL/min on 2 consecutive estimations at least 2 weeks apart or serum creatinine ≥1.5 mg/dL (132.6 μmol/L) or serum albumin <3.2 g/dL.

E 04. Patients taking erythropoietin for the treatment of anemia.

E 05. Anti-phospholipid syndrome: patients with a history of anti-phospholipid antibody syndrome AND use of oral anticoagulants or anti-platelet treatment (excluding acetylsalicylic acid ≤325 mg/day), or a history of arterial or venous thrombosis within 12 months of screening.

E 06. Any recent signs of spontaneous bleeding due to thrombocytopenia within 28 days of screening or during the screening period.

E 07. SLE-related clinical issues or other co-morbidities that in the opinion of the investigator would place the health or well-being of the patient in jeopardy or confound the interpretation of study results (e.g., uncontrolled hypertension, uncontrolled diabetes), any age-related co-morbidities, especially congestive heart failure, acute or active heart disorders (e.g., acute myocardial infarction, myocarditis), chronic cardiac conditions, poorly controlled or progressive (e.g., documented left/right ventricular hypertrophy, clinically significant valvular disease, poorly controlled hypertension, cardiomyopathy), chronic obstructive pulmonary disease, frequent asthma exacerbations.

E 08. Prior or current history of malignancy within 5 years prior to screening (other than adequately treated carcinoma in situ of the cervix, non-metastatic squamous cell or basal cell carcinoma >1 year prior to screening).

E 09. History of congenital or primary immune deficiency.

E 10. Conditions other than SLE that could require oral treatment with corticosteroids. Use of topical (for conditions such as contact dermatitis) or inhaled corticosteroids (for conditions such as asthma) was not exclusionary.

E 11. Marked baseline prolongation of QT/QTc interval, e.g., repeated demonstration of a QTc interval >450 ms.

E 12. History of substance abuse, drug addiction or alcoholism with a remission lasting <1 year prior to screening.

Biological Status

E 13. Positive result on any of the following tests: hepatitis B surface antigen (HBsAg), anti-hepatitis B core antibodies, anti-hepatitis C virus antibodies, anti-human immunodeficiency virus (HIV) 1 and 2 antibodies.

E 14. Infections:
Positive IgM antibody titers in the presence of negative IgG titers to Epstein-Barr virus, cytomegalovirus (CMV), or hepatitis A.

Any current or recent (within 4 weeks of screening) signs or symptoms of infection, except for minor infections, fungal infections of the nail beds or vaginal candidiasis.

Active infection requiring hospitalization or treatment with intravenous (IV) antibiotics within the past 60 days or oral antibiotics during 30 days prior to screening.

Patients with a history of chronic infection or any frequent recurrent infection deemed unacceptable as per investigator judgment.

Any history or evidence of opportunistic infections within 6 months of screening including severe CMV.

History of recurrent herpes zoster, active herpes zoster/chickenpox within 3 months of screening, chickenpox exposure within 21 days prior to screening and/or history of severe herpes infections such as herpes encephalitis, ophthalmic herpes, disseminated herpes.

Frequent recurrence of oral or genital herpes simplex lesions (≥6/year).

Patient with latent (or history of latent, treated) or active tuberculosis (TB), regardless of treatment history, defined as:
  Any signs or symptoms suggestive of active TB upon medical history or clinical examination,
  Patients with a positive QuantiFERON TB Gold test. This test was to be repeated once if indeterminate or believed to be a false positive to ensure patients had negative results prior to inclusion,
  Chest X-ray within 3 months prior to the inclusion visit consistent with prior TB infection or *Mycobacterium* TB exposure, including but not limited to, apical scarring, apical fibrosis, or multiple calcified granulomata. This did not include non-caseating granulomata. The need for a chest X-ray was assessed according to guidelines and local practices, depending on the patient's risk for TB,
  Patients with a history of TB may have been enrolled in the study if adequate treatment was documented by a specialist and patients must have had a negative QuantiFERON TB Gold test,
  Patients with close contact with a person with active TB.

Patients treated with granulocyte colony stimulating factor for neutropenia.

E 15. Known or suspected hypersensitivity to SAR113244 or excipients.

E 16. Receipt of any vaccine within 3 months prior to the randomization (baseline) visit. History of severe allergic or anaphylactic reactions to any biological agent.

E 17. Patients with the following laboratory abnormalities
  Hemoglobin <8.5 g/dL (<85 g/L).
  White blood cells <2000/mm³ (<2.0×10⁹/L).
  Neutrophils <1000/mm³ (<1.0×10⁹/L).
  Absolute lymphocyte count <800/mm³ (<0.8×10⁹/L).
  B cells <50/mm³ and T cells <500/mm³.
  Platelets <50,000/mm³ (<50.0×10⁹/L).
  Alanine aminotransferase (ALT) and/or aspartate aminotransferase (AST) >1.5 upper limit of normal (ULN).
  Alkaline phosphatase >1.5 ULN.
  Immunoglobulins (IgG, IgM, IgA) below lower limit of normal (LLN).

E 18. Positive result on urine drug screen (amphetamines/methamphetamines, barbiturates, benzodiazepines, cannabinoids, cocaine, opiates), unless due to a medically prescribed co-medication.

E 19. Positive urine alcohol (ethanol) test.

Interfering Drug

E 20. Oral treatment with corticosteroids (>0.3 mg/kg/day prednisone or equivalent) within 30 days prior to first dose of study medication except for a duration of ≤3 days from 30 to 15 days prior to dosing.
  Intra-articular steroid injection(s) within 30 days prior to the first dose.

E 21. Unwilling to continue on a stable baseline corticosteroids dose from screening to at least 6 weeks following final dose administration. A single dose adjustment of prednisone (or equivalent) up to +5 mg/day was allowed.

E 22. Immunomodulator/immunosuppressive treatments (excluding corticosteroids):
  Any B cell depleting agent (rituximab, belimumab or other investigational product) within 6 months of randomization or 5 half-lives of the biologic agent, whichever was longer, and without demonstration of a return of CD19+ B cells to >50/μL.
  Abatacept within 3 months prior to randomization; other biologic therapies (such as anti-tumor necrosis factor α, anti-interleukin 6) within 30 days or 5 half-lives of the biological agent, whichever was longer, before randomization into the study.
  Initiation of methotrexate, azathioprine, hydroxychloroquine or other antimalarials (chloroquine, quinacrine), mycophenolate mofetil or dapsone within 90 days prior to dosing:
    The following doses were exclusionary: methotrexate >25 mg/week; azathioprine >2.5 mg/kg/day; hydroxychloroquine >400 mg/day; chloroquine, >3.5 mg/kg/day, quinacrine >100 mg/day; dapsone >200 mg/day; mycophenolate mofetil >2.5 g/day and initiated <90 days prior to randomization or fluctuating doses <14 days prior to study screening and during the screening period.
  Administration of cyclosporine, tacrolimus, sirolimus, thalidomide, lenalidomide, IV Ig and/or plasmapheresis administered within 3 months prior to screening.
  Administration of leflunomide within 6 months prior to screening, unless a formal washout procedure had been administered and documentation provided.
  Receipt of cyclophosphamide (IV or oral) or any other alkylating agent, within 6 months of screening.

E 23. Non-steroidal anti-inflammatory drugs (including COX-2) in fluctuating doses within 14 days before screening and during the screening period.

E 24. Use of warfarin or heparin.

E 25. Simultaneous participation or participation within 4 months or 5 half-lives (whichever was longer) prior to screening in any other study involving investigational drugs or other experimental treatment.

General Conditions

E 26. Pregnancy (defined as positive pregnancy test), breast-feeding.

E 27. Any patient who, in the judgment of the investigator, was likely to be noncompliant during the study, or unable to cooperate because of a language problem or poor mental development.

E 28. Patient was an employee of the clinical site, e.g., the investigator or any subinvestigator, research assistant, pharmacist, study coordinator, other staff or relative; patient or relative is an employee of the Sponsor.

Removal of Patients from Therapy or Assessment

Each patient could have withdrawn from the study, if they decided to do so, at any time and irrespective of the reason. Patients could also have been withdrawn upon the investigator's decision. All study treatment withdrawals were to be recorded in the electronic case report form (eCRF). If possible, patients were assessed using EOS procedures, including a PK sample, if appropriate.

Patients who discontinued treatment due to an AE were to be followed-up according to the study procedures for at least 84 days after the last injection up to the scheduled date of study completion (EOS visit), or up to recovery or stabilization of any AE to be followed-up, whichever came last.

For any patient who failed to return to the site, the investigator made every effort to contact the patient (e.g., contact the patient's family or private physician, review available registries, or health care databases), and to determine his/her health status, including at least his/her vital status. Attempts to contact the patient were documented in the patient's records (e.g., times and dates of attempted telephone contact, receipt for sending a registered letter).

Patients withdrawn from the study were not reincluded in the study. Their inclusion and treatment numbers were not reused.

Treatments

Treatments Administered

SAR1133244

SAR113244 solution for injection was used for SC administration as a sterile, nonpyrogenic, injectable, colorless to slightly yellow, 100 mg/mL solution, which was packaged in 2R ISO glass vials fitted with elastomeric closures.

Each vial contained a nominal 150 mg (1.5 mL) of SAR113244 (over-fill of 0.2 mL). The pH of the solution was between 5.5 and 6.5. The solution contained the following excipients: water for injection, sucrose, arginine hydrochloride, sodium citrate, sodium chloride, polysorbate 20, and hydrochloric acid/sodium hydroxide solution for pH adjustment, if necessary.

Placebo

Isotonic saline (0.9%) injection in vials

Specific handling requirements per manufacturer's requirements.

The investigational medicinal product (IMP; SAR113244 or placebo) was administered as SC injections in the abdominal area. Patients were fasted for at least 10 hours prior to dosing and for 2 hours postdose.

As doses required multiple injections, the administration was alternated between the left and right upper quadrants and left and right lower quadrants in a zone 4 to 10 cm from the umbilicus; same day injections were administered in different quadrants.

Identity of Investigational Medicinal Products

SAR113244 100 mg/mL vials were packaged into cartons as open-labeled supplies. The content of the labeling was in accordance with the local regulatory specifications and requirements.

SAR113244 100 mg/mL was stored between 2° C. and 8° C. (36° F. and 48° F.), protected from light, and with limited shaking (no rotation). SAR113244 was not frozen. Light exposure was permissible during preparation and administration.

Isotonic saline (0.9%) was stored according to the manufacturer's requirements.

Batch numbers for SAR113244 and placebo were C1037128 and 14384011.

Method of Assigning Patients to Treatment Groups

Patients who complied with all of the inclusion criteria and had signed the informed consent were assigned a patient number and a randomization number. The randomization was performed by a centralized randomization procedure using an interactive response system.

For the 500 mg cohort, the randomization was stratified according to plasmablast/plasma cells level (< or ≥5% of total B cells) at screening, using a 1:1 ratio.

Potential replacement patients were to be assigned a different identification number (i.e., 500+the number of replaced patient). Each patient was to receive the same treatment and treatment sequence as the withdrawn patient.

Selection of Doses in the Study

Based on blinded safety and preliminary PK results of study TDU11406 in healthy subjects up to 500 mg SAR113244 or placebo, the doses to be administered in a repeated manner to SLE patients in this study were determined to be 250 mg and 500 mg once every 4 weeks (Q4W) as 2 injections. A higher dose of 800 mg Q4W (2 injections) was optional depending on the safety, PK, and PD profile observed in patients of previous groups.

The planned SAR113244 treatment regimen was as follows:

TABLE 1

| | | | Planned SAR113244 treatment regimen | | |
|---|---|---|---|---|---|
| Group | Dose (mg) | Dose regimen | Total volume injected per administration | Number of injections | Volume per injection |
| 1 | 250 | Q4W ×2 | 2.5 mL | 2 | 1.0 + 1.5 = 2.5 mL |
| 2 | 500 | Q4W ×2 | 5.0 mL | 3 | 1.5 + 1.5 + 2.0 = 5.0 mL |
| 3 (optional) | 800 | Q4W ×2 | 8.0 mL | 4 | 2.0 + 2.0 + 2.0 + 2.0 = 8 mL |

The optional Group 3 was not implemented (the highest dose administered was 500 mg). Group 2 was terminated early because preliminary results indicated that 500 mg would be an appropriate dose level for subsequent studies.

Selection and Timing of Dose for Each Patient

Patients were assigned to treatments according to the randomization list.

SAR113244 or placebo was administered to patients in the fasted state in the morning of Day 1 and in the morning of Day 29 starting with the first patient at approximately 8:00 AM. After dosing, patients remained in the clinical unit until the morning of the following day (i.e., Day 2 and Day 30) and discharged from the unit after morning evaluations on Day 2 and Day 30.

Prior and Concomitant Therapy

The use of concomitant medication was prohibited during the study unless specified in the inclusion criteria or study procedures, or was medically required. However, if a specific treatment was required for any reason, an accurate record was to be entered in the eCRF, including the name of the medication (international nonproprietary name), daily dosage, and duration of use.

Pharmacodynamics, Safety and Pharmacokinetics Assessments

An overview of safety, PK, and PD assessments relative to study procedures is presented in the study flowchart (Table 2); a detailed schedule of the treatment period is provided in the period flowchart (Table 3).

TABLE 2

Study Flowchart

| Phase | Screening D-28 to | | | | | | | Treatment phase | | | | | | | | EOS D113 +/-7 | Post study period D226 +/-7 |
|---|---|---|---|---|---|---|---|---|---|---|---|---|---|---|---|---|---|
| Day | D-2 | D-1 | D1 | D2 | D8 | D15 | D28 | D29$^m$ | D30 | D36 | D43 | D57 | D71 | D85 | | | |
| Informed consent | X | | | | | | | | | | | | | | | | |
| Institutionalization | | X | | | | | X | | | | | | | | | | |
| Discharge | | | | X | | | | | X | | | | | | | | |
| Visit at clinical site | X | | | | X | X | | | | X | X | X | X | X | X | X | |
| Inclusion/exclusion criteria | X | X | | | | | | | | | | | | | | | |
| Medical/surgical history | X | X | | | | | | | | | | | | | | | |
| Prior/concomitant medications | ←- | --- | --- | --- | --- | --- | --- | --- | --- | --- | ---- | --- | | --- | ---- | → | |
| Inclusion | | | X$^a$ | | | | | | | | | | | | | | |
| Randomization | | | X$^a$ | | | | | | | | | | | | | | |

Study treatment administration

| | | | | | | | | | | | | | | | | | |
|---|---|---|---|---|---|---|---|---|---|---|---|---|---|---|---|---|---|
| SAR113244 or placebo | | | X | | | | | | X | | | | | | | | |

Safety$^e$

| | | | | | | | | | | | | | | | | | |
|---|---|---|---|---|---|---|---|---|---|---|---|---|---|---|---|---|---|
| Physical examination | X | X | | X | X | X | X | | X | X | X | X | X | X | X | | |
| Height | X | | | | | | | | | | | | | | | | |
| Body weight | X | X$^a$ | | | | X | | | X | | | X | | | X | | |
| Oral body temperature, vital signs | X | X | X$^c$ | X | X | X | X | X$^c$ | X | X | X | X | X | X | X | | |
| ECG | X | X | X$^c$ | X | | X | X | X$^c$ | X | | X | | | | X | | |
| Chest X-ray$^h$ | X | | | | | | | | | | | | | | | | |
| Archival blood sample | | | X$^A$ | | | | | | | | | | | | | | |
| Tolerability at investigationa lproduct injection site | | | X | X | X | X | | | X | X | X | X | X | X | X | | |
| Hematology, , biochemistiy urinalysis | X | X$^k$ | X$^d$ | X | X | X | X$^k$ | X$^d$ | X | X | X | X | | X | X | | |
| Serology tests$^b$ | X | | | | | | | | | | | | | | | | |
| Pregnancy test$^i$ | X | X | | | | | | | X | | | X | | X | X | | |
| QuantiFERON ®-TB Gold test | X | | | | | | | | | | | | | | | | |
| Serum immunoglobulins (IgG, IgM, IgE, IgA and IgD) | X | | X$^a$ | | | X | | | X$^a$ | | | X | X | | X | X | |
| Total peripheral blood B and T cells (safety) | X | | X$^a$ | X | | X | | | X$^a$ | | | X | X | | X | X | |
| Urine drug screen, alcohol test | X | X | | | | | | | | | | | | | | | |
| Adverse event collection | ←----- | -- | -- | -- | -- | -- | -- | -- | -- | --- | --- | -- | --- | -- | --- | -----→ | |

Pharmacokinetics

| | | | | | | | | | | | | | | | | | |
|---|---|---|---|---|---|---|---|---|---|---|---|---|---|---|---|---|---|
| SAR113244 PK plasma samples | | | X$^a$ | X | X | X | | | X$^a$ | X | X | X | X | X | X | X | |
| CXCR5 receptor occupancy on peripheral B cell | | | X$^a$ | | X | X | | | X$^a$ | | X | X | X | | X | X | |
| Anti-SAR113244 antibodies plasma samples | | | X$^a$ | | X$^n$ | | | | X$^a$ | | X$^n$ | X | | X | X | X$^j$ | |

TABLE 2-continued

Study Flowchart

| | Screening D-28 to | | | | | | Study period Treatment phase | | | | | | | | EOS D113 | Post study period D226 |
|---|---|---|---|---|---|---|---|---|---|---|---|---|---|---|---|---|
| Phase | | | | | | | | | | | | | | | | |
| Day | D-2 | D-1 | D1 | D2 | D8 | D15 | D28 | D29[m] | D30 | D36 | D43 | D57 | D71 | D85 | +/−7 | +/−7 |
| *Pharmacogenetics* | | | | | | | | | | | | | | | | |
| DNA samples[f] | | | X[a] | | | | | | | | | | | | | |
| RNA (whole blood) sample | | | X[a] | X | X | | | X[a] | | | X | X | | X[n] | | |
| *Pharmacodynamics* | | | | | | | | | | | | | | | | |
| Anti-dsDNA antibodies and plasma complement levels (C3, C4) | X | | X[a] | | | X | | X | | | X | | | X | X | |
| ANA blood sample | X | | X[a] | | | | | | | | | | | | X | |
| SELENA-SLEDAI score | X | | X[a] | | | X | | X[a] | | | | X | | X | X | |
| BILAG score (if applicable) | | | X[a] | | | | | X[a] | | | | X | | X | X | |
| PGA score | | | X[a] | | | | | X[a] | | | | X | | X | X | |
| Anti-Smith, anti-Ro, anti-La, anti-cardiolipin (IgG, IgM) | | | X[a] | | | | | | | | | | | | X | |
| Lupus-QoL and FACIT-Fatigue scores | | | X[a] | | | | | X[a] | | | | X | | X | X | |
| Blood SED rate and CRP | | | X[a] | X | X | X | | X | | X | X | X | | X | X | |
| CXCR5 binding on peripheral B and T cells and peripheral blood B subsets (including plasmablasts) and T cells subsets characterization) (exploratory | X[g] | | X[a] | X[n] | X | | | X[a] | | | X | X[n] | X[n] | X | | |
| Serum CXCL 13 | | | X[a] | X | X | | | X[a] | | | X | X | | X | X | |
| Exploratory serum markers[l] | | | X[a] | X | X | | | X[a] | | | X | X | | X | X | |
| Exploratory biomarker analysis (serum and plasma protein analysis) | | | X[a] | | X | | | X[a] | | | X[n] | | | X[n] | | |
| Exploratory urine biomarkers including CXCL13 | | | X[a] | X | X | | | X[a] | X | X | X | | | X | X | |

[a]Predose.
[b]Serology tests: hepatitis B surface antigen (HBsAg), hepatitis B core antibody, hepatitis C antibody, Epstein-Barr virus and cytomegalovirus antibodies, anti-HIV1 and anti-HIV2 antibodies.
[c]Refer to period flow chart for detailed timing of assessments.
[d]Predose, 8 hours (T8H performed by local laboratory) and 12 hours postdose.
[e]Refer to safety section for detailed safety investigations.
[f]Collection of blood for DNA pharmacogenetic patients analysis for those who have signed the separate pharmacogenetics informed consent form (collection may occur on another study day if necessary).
[g]Plasmablasts/plasma cells only.
[h]Chest X-ray examination at screening unless there is a documented CXR interpretation confirming no infection within 3 months/90 days of enrollment.
[i]Serum beta-HCG at screening and D-1 (D-1 performed by local laboratory), urine pregnancy test afterwards.
[j]Only for patients tested positive for ADA at the D113 (EOS) visit.
[k]Hematology/complete blood count only; performed by local laboratory.
[l]Exploratory serum markers: archival blood sample for research purpose.
[m]A visit window of ±1 day was permitted for the second administration (visit D29) only under exceptional circumstances. In this case the assessment schedule was to be followed as planned for D29 and the following visits were to be scheduled based on the day of second administration.
[n]Cohort 2 only.

Note:
when several items were scheduled at the same time, the following was to be respected: PD (except if biological samples), ECG, vital signs, blood sampling, drug administration, meal. In order to respect exact timing of PK samples, the other measures were ahead of the performed scheduled time.

TABLE 3

Period flowchart

| Day | D1 | | | | | | | | | D2 | D8 | D15 |
|---|---|---|---|---|---|---|---|---|---|---|---|---|
| Time (hour/minute)[b] | 0H | 0H30 | 2H | 3H | 4H | 6H | 8H | 10H | 12H | 24H | 168H | 336H |
| Indicative clock time | 8 am | 8:30 am | 10 am | 11 am | 12 pm | 2 pm | 4 pm | 6 pm | 8 pm | 8 am | 8 am | 8 am |
| Institutionalization | | | | | | | | | | | | |
| Discharge | | | | | | | | | | X | | |
| Visit at clinical site | | | | | | | | | | | X | X |
| Concomitant medications | ← | --- | --- | --- | --- | --- | ---- | ---- | ---- | ---- | --- | ---- |
| Inclusion | X[a] | | | | | | | | | | | |
| Randomization | X[a] | | | | | | | | | | | |
| Meals | | | X[c] | | X | | | X | X[c] | | | X |
| Study treatment administration | | | | | | | | | | | | |
| SAR113244 or placebo | X | | | | | | | | | | | |
| Safety[e] | | | | | | | | | | | | |
| Physical examination | | | | | | | | | | X | X | X |
| Body weight | | | | | | | | | | | | X |
| Archival blood sample | X[a] | | | | | | | | | | | |
| Oral body temperature/vital signs | X[a] | X | X | X | X | X | X | | | X | X | X |
| ECG | X[a] | X | X | X | X | X | X | | | X | X | X |
| Hematology, biochemistry, urinalysis | X[a] | | | | | | X[j] | | | X | X | X |
| Tolerability at investigational product injection | | X | X | | X | | | | | X | X | X |
| Total peripheral blood B and T cells (safety) | X[a] | | | | | | | | | | X | X |
| Serum immunoglobulins | X[a] | | | | | | | | | | | X |
| Adverse event collection | ← | --- | --- | --- | --- | --- | --- | --- | --- | --- | --- | ---→ |
| Pharmacokinetics | | | | | | | | | | | | |
| SAR113244 PK plasma samples | P000[a] | | | | | | | | | P01 | P02 | P03 |
| CXCR5 receptor occupancy on peripheral B cell | X[a] | | | | | | | | | | X | X |
| Anti-SAR113244 antibodies plasma samples | X[a] | | | | | | | | | | | X[k] |
| Pharmacogenectics | | | | | | | | | | | | |
| DNA samples[e] | B00[a] | | | | | | | | | | | |
| RNA (whole blood) sample | X[a] | | | | | | | | | | X | X |
| Pharmacodynamics | | | | | | | | | | | | |
| ANA blood sample | X[a] | | | | | | | | | | | X |
| Anti-dsDNA antibodies and plasma complement levels (C3, C4) | X[a] | | | | | | | | | | | X |
| SELENA-SLEDAI score | X[a] | | | | | | | | | | | |
| BILAG score (if applicable) | X[a] | | | | | | | | | | | |
| PGA score | X[a] | | | | | | | | | | | |
| Anti-Smith, anti-Ro, anti-La, anti-cardiolipin (IgG, IgM) | X[a] | | | | | | | | | | | |
| Lupus-QoL and FACIT-Fatigue scores | X[a] | | | | | | | | | | | |
| Blood SED rate and CRP | X[a] | | | | | | | | | | X | X |
| CXCR5 binding on peripheral B and T cells and plasmablasts/peripheral blood T cells another B cells subsets (exploratorycharacterization) | X[a] | | | | | | | | | | X[k] | X |
| Serum CXCL13 | X[a] | | | | | | | | | | X | X |
| Exploratory serum markers[g] | X[a] | | | | | | | | | | X | X |
| Exploratory biomarker analysis (serum and plasma protein analysis) | X[a] | | | | | | | | | | | X |
| Exploratory urine biomarker including urine CXCL13 | X[a] | | | | | | | | | | X | X |

| Day | D28 | D29[j] | | | | | | | | 12H | D30 | D36 |
|---|---|---|---|---|---|---|---|---|---|---|---|---|
| Time (hour/minute)[b] | | 0H | 0H30 | 2H | 3H | 4H | 6H | 8H | 10H | 8 pm | 24H | 168H |
| Indicative clock time | 8 pm | 8 am | 8:30 am | 10 am | 11 am | 12 pm | 2 pm | 4 pm | 6 pm | | 8 am | 8 am |
| Institutionalization | X | | | | | | | | | | | |
| Discharge | | | | | | | | | | | X | |
| Visit at clinical site | | | | | | | | | | | | X |
| Concomitant medications | ← | --- | --- | --- | --- | --- | --- | --- | --- | --- | ---- | ---- |
| Inclusion | | | | | | | | | | | | |
| Randomization | | | | | | | | | | | | |
| Meals | | X | | X[c] | | X | | | X | X[c] | | |

TABLE 3-continued

Period flowchart

Study treatment administration

| | | | | | | | | | | | | |
|---|---|---|---|---|---|---|---|---|---|---|---|---|
| SAR113244 or placebo | | X | | | | | | | | | | |

Safety[d]

| | | | | | | | | | | | | |
|---|---|---|---|---|---|---|---|---|---|---|---|---|
| Physical examination | X | | | | | | | | | | X | X |
| Body weight | | X | | | | | | | | | | |
| Pregnancy test[f] | | X[a] | | | | | | | | | | |
| Oral body temperature/vital signs | X | X[a] | X | X | X | X | X | X | | X | X | X |
| ECG | X | X[a] | X | X | X | X | X | X | | X | X | |
| Serum Immunoglobulins | | X[a] | | | | | | | | | | |
| Hematology, biochemistry, urinalysis | X[h+i] | X[a] | | | | | X[i] | | | X | X | X |
| Tolerability at investigational product injection | | X | X | X | | X | | | | X | X | X |
| Total peripheral blood B and T cells (safety) | | X[a] | | | | | | | | | X | |
| Adverse event collection | ← | --- | --- | --- | ---- | ---- | ---- | ---- | ---- | ---- | ---- | ---- |

Pharmatokinetics

| | | | | | | | | | | | | |
|---|---|---|---|---|---|---|---|---|---|---|---|---|
| SAR113244 PK plasma samples | | P04 | | | | | | | | | P05 | P06 |
| CXCR5 receptor occupancy on peripheral B cell | | X[a] | | | | | | | | | | X |
| Anti-5AR113244 antibodies plasma samples | | X[a] | | | | | | | | | | |

Pharmacogenetics

| | | | | | | | | | | | | |
|---|---|---|---|---|---|---|---|---|---|---|---|---|
| DNA samples e | | | | | | | | | | | | |
| RNA (whole blood) sample | | X | | | | | | | | | | |

Pharmacodynamics

| | | | | | | | | | | | | |
|---|---|---|---|---|---|---|---|---|---|---|---|---|
| ANA blood sample | | | | | | | | | | | | |
| Anti-dsDNA antibodies and plasma complement levels (C3, C4) | | X | | | | | | | | | | |
| SELENA-SLEDAI score | | X[a] | | | | | | | | | | |
| BILAG score (if applicable) | | X[a] | | | | | | | | | | |
| PGA score | | X[a] | | | | | | | | | | |
| Anti-Smith, anti-Ro, anti-La, anti-cardiolipin (IgG, IgM) | | | | | | | | | | | | |
| Lupus-QoL and FACIT-Fatigue (if available) scores | | X[a] | | | | | | | | | | |
| Blood SED rate and CRP | | X[a] | | | | | | | | | | X |
| CXCR5 binding on peripheral B and T cells and plasmablasts/peripheral blood T cells and other B cells subsets (exploratory) characterization | | X[a] | | | | | | | | | | |
| Serum CXCL13 | | X[a] | | | | | | | | | | X |
| Exploratory serum markers[g] | | X[a] | | | | | | | | | | |
| Exploratory biomarker analysis (serum and plasma protein analysis) | | X[a] | | | | | | | | | | |
| Exploratory urine biomarker including urine CXCL13 | | | | | | | | | | | | X |

| | | | | | |
|---|---|---|---|---|---|
| Day | D43 | D57 | D71 | D85 | D113 +/− 7 |
| Time (hour/minute)[b] | 336H | 672H | 1008H | 1344H | 2016H +/− 168 |
| Indicative clock time | 8 am | 8 am | 8 am | 8 am | 8 am |

| | | | | | |
|---|---|---|---|---|---|
| Institutionalization | | | | | |
| Discharge | | | | | |
| Visit at clinical site | X | X | X | X | X |
| Concomitant medications | ---- | ---- | ---- | ---- | --→ |
| Inclusion | | | | | |
| Randomization | | | | | |
| Meals | | | | | |

Study treatment administration

| | | | | | |
|---|---|---|---|---|---|
| SAR113244 or placebo | | | | | |

Safety[d]

| | | | | | |
|---|---|---|---|---|---|
| Physical examination | X | X | X | X | X |
| Body weight | | X | | | X |
| Pregnancy test[f] | | X | | X | X |
| Oral body temperature/vital signs | X | X | X | X | X |
| ECG | X | | | | X |
| Serum Immunoglobulins | X | X | | X | X |
| Hematology, biochemistry, urinalysis | X | X | | X | X |
| Tolerability at investigational product injection | X | X | X | X | X |

TABLE 3-continued

| Period flowchart | | | | | |
| --- | --- | --- | --- | --- | --- |
| Total peripheral blood B and T cells (safety) | X | X | | X | X |
| Adverse event collection | ---- | ---- | | ---- | --→ |
| Pharmatokinetics | | | | | |
| SAR113244 PK plasma samples | P07 | P08 | P09 | P10 | P11 |
| CXCR5 receptor occupancy on peripheral B cell | X | X | | X | X |
| Anti-5AR113244 antibodies plasma samples | X[k] | X | | X | X |
| Pharmacogenetics | | | | | |
| DNA samples e RNA (whole blood) sample | X | X | | X[k] | |
| Pharmacodynamics | | | | | |
| ANA blood sample | | | | | X |
| Anti-dsDNA antibodies and plasma complement levels (C3, C4) | | X | | X | X |
| SELENA-SLEDAI score | | X | | X | X |
| BILAG score (if applicable) | | X | | X | X |
| PGA score | | X | | X | X |
| Anti-Smith, anti-Ro, anti-La, anti-cardiolipin (IgG, IgM) | | | | | X |
| Lupus-QoL and FACIT-Fatigue (if available) scores | | X | | X | X |
| Blood SED rate and CRP | X | X | | X | X |
| CXCR5 binding on peripheral B and T cells and plasmablasts/peripheral blood T cells and other B cells subsets (exploratory) characterization | X | X[k] | X[k] | X | |
| Serum CXCL13 | X | X | | X | X |
| Exploratory serum markers[g] | X | X | | X | X |
| Exploratory biomarker analysis (serum and plasma protein analysis) | X[k] | | | X[k] | |
| Exploratory urine biomarker including urine CXCL13 | X | X | | X | X |

[a]Predose.
[b]Time (hour/minute) is expressed in reference to the last administration of SAR113244 or placebo (T0H).
[c]Light snack.
[d]Refer to safety section for detailed safety investigations
[e]Collection of blood for DNA pharmacogenetic analysis for those patients who have signed the separate pharmacogenetics informed consent form (collection may occur on another study day if necessary).
[f]Serum beta-HCG at screening and D-1 (D-1 peiformed by local laboratory), urine pregnancy test afterwards.
[g]Exploratory serum markers: archival blood sample for research purpose.
[h]Hematology/complete blood count only.
[i]Performed by local laboratory.
[j]A visit window of ±1 day was permitted for the second administration (visit D29) only under exceptional circumstances. In this case the assessment schedule was to be followed as planned for D29 and the following visits were to be scheduled based on the day of second administration.
[k]Cohort 2 only.

Pharmacodynamics Assessments

A detailed schedule of PD assessments is provided in Table 2.

CXCR5 Receptor Occupancy

CXCR5 receptor occupancy (RO) by SAR113244 on the cell surface of B lymphocytes (total B lymphocytes population [CD19+]), naïve subpopulation (CD19+/IgD+/CD27−) and memory subpopulations (CD19+/CD27+; or CD19+/IgD−/CD27−) in whole blood samples was assessed using a validated assay. This assay was established using quantitative flow cytometry and employing the use of calibration beads (CellQuant Calibrator kit) to convert the fluorescence intensity of the sample into a value corresponding to the number of antibody bound per cell. The lower limit of quantification (LLOQ) of the assay was 20%.

CXCL13

CXCL13 was quantified in human serum using a validated enzyme-linked immunosorbent assay (ELISA) method. Taking into account a minimal required dilution of the assay, the LLOQ and the upper limit of quantification were 15.6 and 500 pg/mL, respectively. CXCL13 was also quantified in urine using an exploratory ELISA method.

Analysis of B Cell Subsets and Biomarkers of T Cells

Analysis of B and T cell subsets was performed using flow cytometry. In addition to the differentiation of cells by their size (forward scatter) and granulation (sideward scatter), several cellular subpopulations were differentiated by their expression of specific cell surface markers.

The characterization of B and T cell subtypes (e.g., naive cells, memory cells, antibody-secreting cells [i.e., plasmablasts, plasma cells]) based on these markers were used to investigate the biological effect and potential value of biomarkers under SAR113244 treatment.

Disease-Related Parameters

SELENA-SLEDAI score.
British Isles Lupus Assessment Group (BILAG) score.
Anti-Smith, anti-Ro, anti-La, anti-cardiolipin (IgG, IgM).
Anti-dsDNA antibodies and ANA levels.
Plasma complement levels (C3, C4).
Physician Global Assessment (PGA), Lupus-quality of life (QoL) and Functional Assessment of Chronic Illness Therapy (FACIT)-Fatigue.
Blood SED rate and C-reactive protein (CRP).

Safety Variables and Timing of Assessment

Patients were monitored for safety via AEs spontaneously reported by the patients or observed by the investigator, clinical laboratory evaluations (hematology, biochemistry, and urinalysis), serum Igs, peripheral blood B and T cells, anti-SAR113244 antibodies, vital sign measurements, 12-lead electrocardiograms (ECGs), ECG morphology, physical examination, body weight, body temperature, and local tolerability at injection site assessments.

The QuantiFERON TB Gold test was performed at screening only. Serology (HBsAg, hepatitis B core antibody, hepatitis C antibodies, anti-HIV1 and anti-HIV2 antibodies, positive IgM antibody titers in the presence of negative IgG titers to Epstein-Barr virus, CMV, hepatitis A) was performed at screening only; urine drug screens and urine alcohol tests were performed at screening and on Day −1. If female, a serum pregnancy test was performed at screening and randomization and a urine pregnancy test thereafter.

The schedules of safety assessments are presented in Table 2 and Table 3.

Adverse Events

All AEs, regardless of seriousness or relationship to IMP, from the signature of the ICF until the EOS visit, were recorded. The investigator documented details per eCRF, including their relationship to the IMP.

A serious adverse event (SAE) is any untoward medical occurrence that at any dose:

Results in death, or,
Is life-threatening, or,
Requires inpatient hospitalization or prolongation of existing hospitalization, or,
Results in persistent or significant disability/incapacity, or,
Is a congenital anomaly/birth defect, or,
Is a medically important event.

Laboratory Safety Parameters

Standard clinical laboratory parameters (biochemistry, hematology, and urinalysis) were measured.

Other Safety Parameters

1. Vital Signs

Heart rate, systolic blood pressure (SBP), and diastolic blood pressure (DBP) were measured after 10 minutes in the supine resting position and after 3 minutes in the standing position.

2. Electrocardiograms

Twelve-lead ECGs were recorded after at least 10 minutes in the supine position (10-second recording at 25 mm/s, 10 mm/mV).

An ECG profile was assessed by means of 12-lead ECGs, evaluated at several time points throughout the study and centrally read by an ECG Core Lab (semi-automatic reading) at all time points except screening. Each time point was a single record.

The following parameters were received from the ECG reading center:

RR (in ms), mean from all the sinus rhythm complexes recorded over the 10 seconds.
HR (in bpm), from mean RR of all the sinus rhythm complexes recorded over the 10 seconds.
PR (in ms), global interval measurement from superimposition of the 12-lead individual median beats.
QRS (in ms), global interval measurement from superimposition of the 12-lead individual median beats.
QT (in ms), global interval measurement from superimposition of the 12-lead individual median beats.
QT interval corrected for heart rate using Bazett's formula (QTcB) (in ms), Bazett's correction (QTcB=QT·RR−0.50) from the global QT and mean RR.
QT interval corrected for heart rate using Fridericia's formula (QTcF) (in ms), Fridericia's correction (QTcF=QT·RR-0.33) from the global QT and mean RR.

Morphological analyses of ECG waveforms were also performed.

3. Local Tolerability at Injection Site

The skin around the SC injection area was examined (at scheduled time points or any time a reaction was observed) for potential reactions to the SC injection. Findings were documented for each injection and separately for each injection site (when the administration of each dose was performed via multiple injections at the same time point). The maximum diameter of erythema and swelling (including induration and/or edema) was measured separately in millimeters and recorded. Erythema and swelling were graded separately. If there were no treatment-emergent changes in a parameter at the time of observation, a value of 0 was recorded.

Additionally, any injection site reactions with intensity grade of "severe" or worse, or all injection site reactions lasting more than 24 hours regardless of intensity grade were reported as an AE of special interest (AESI).

The presence or absence of the following symptoms or superficial observations was recorded without grading: erosion, dryness, scaling, cracking, scabbing, and glazing. It was the investigator's responsibility to decide if any local ungraded tolerability observation should have been reported as an AE.

4. Immunoglobulins

Blood samples for serum immunoglobulins (IgG, IgM, IgD, IgE, IgA) were collected at the time points provided in Table 2 and Table 3.

5. Total Peripheral Blood B and T Cells

Blood samples for total peripheral blood B and T cells were collected at the time points provided in Table 2 and Table 3.

Pharmacokinetics Assessments and Timing

Pharmacokinetic Measurements and Timing

Pharmacokinetic sampling times are provided in the study flowchart in Table 2 and the period flowchart in Table 3.

The concentrations of SAR113244 in plasma were determined with a validated ELISA technique with an LLOQ of 0.040 μg/mL.

In addition, immunogenicity assessment sampling times are provided in the study flowchart (Table 2). The ADA assay was performed using a validated ELISA method. All samples were first evaluated using a screening assay. Samples found positive in the screening assay were then tested in a confirmatory assay. A titer was reported only for samples confirmed to be positive.

Pharmacokinetic Variables

Plasma concentrations of SAR113244 and relative actual time values were used to calculate the PK parameters listed in Table 4, using noncompartmental methods with validated software (PKDMS version 2.2 running with WinNonlin version 5.2.1, Certara).

TABLE 4

Pharmockinetics parameters

| Parameters | Matrix | Definition/Calculation |
|---|---|---|
| $C_{max}$ | Plasma | Maximum plasma concentration observed |
| $t_{max}$ | Plasma | First time to reach $C_{max}$ |
| $AUC_{0-4w}$ | | Area under the concentration versus time curve calculated using the trapezoidal/method during a dosage interval |
| $t_{1/2z}$ | Plasma | Terminal half-life associated with the terminal slope ($\lambda z$) determined according to the following equation: $$t_{1/2Z} = \frac{0.693}{\lambda_z}$$ where $\lambda z$ is the slope of the regression line of the terminal phase of the plasma concentration versus time curve, in semi-logarithmic scale. Half-life was calculated by taking the regression of at least 3 points |
| $CL_{ss}/F$ | | Apparent total body clearance of a drug at steady state from the plasma calculated using the following equation: $$CL_{ss}/F = \frac{Dose}{AUC_{0-\tau}}$$ |
| $V_{ss}/F$ | | Apparent volume of distribution at the steady state after repeated dose calculated using the following equation: $$Vss/F=CFss/F \times MRT$$ where MRT is the Mean Residence Time |

Appropriateness of Measurements

Standard measurements appropriate for the analysis of the safety and tolerability, PD, and PK of SAR113244 were used in this study.

Statistical Considerations

Determination of Sample Size

The sample size for this study was based upon empirical considerations. No sample size calculation was performed.

Analysis Populations

Pharmacodynamic Population

All patients with no major or critical protocol deviations for whom the primary PD data were considered sufficient and interpretable were included in the PD population. Patients treated with placebo were not included in the analysis of RO data.

Safety Population

All patients who were exposed to study treatment, regardless of the amount of treatment administered, were included in the safety population.

Pharmacokinetic Population

All patients with no major or critical deviations related to study drug intake and for whom the primary PK data were considered sufficient and interpretable were included in the PK population. Patients who received only placebo were not included in the PK population.

Statistical Analyses

Demographics and Baseline Characteristics

Demographic variables were summarized by treatment group and overall using descriptive statistics in the safety population. Continuous data were summarized using the number of available data, mean, standard deviation (SD), median, minimum and maximum. Categorical and ordinal data were summarized using the number and percentage of patients in each treatment group. All data were listed.

Medical or surgical history were coded using Medical Dictionary for Regulatory Activities (MedDRA, version 18.1). All reported medical and surgical history were presented by primary system organ class (SOC) and high level terms, by treatment groups and overall. All medical history data, including the family autoimmune disease medical history in any immediate relative(s), were listed.

Baseline disease characteristics were summarized by treatment group and overall using descriptive statistics in the safety population. Continuous data were summarized using the number of available data, mean, SD, median, minimum and maximum, and the 1st and 3rd quarter; the number of imputed values was also provided for anti-dsDNA antibody level. Categorical and ordinal data were summarized using the number and percentage of patients in each treatment group.

Prior or Concomitant Medications

The following medications were reported in the appropriate eCRF pages:

Previous and concomitant corticosteroids taken for lupus within 5 years before the study entry and during the whole study.

Previous and concomitant medications taken for lupus other than corticosteroids within 6 months before the study entry and during the whole study.

Previous and concomitant medications not related to lupus within 3 months before the study entry and during the whole study.

All medications were coded using the World Health Organization-Drug Dictionary, 2015SEP version).

Medications were summarized by treatment group according to the World Health Organization-Drug Dictionary. The prior and concomitant medications were summarized for the safety population. All medications were listed.

Extent of Investigational Medicinal Product Exposure and Compliance

The treatment exposure (i.e., number of days of administration) was summarized by treatment group for the safety population.

The details of drug dosing (actual treatment received, date and time of IMP administration, intended and actual dose received, patients receiving IMP from specified batch, and the randomization scheme) were listed.

Analyses of Pharmacodynamic Endpoints

All PD analyses were performed using the PD population.

1. Disease-Related Markers

The following markers were analyzed as raw data, absolute and percentage change from baseline, unless otherwise specified. Only data assessed centrally by Covance were taken into account.

Anti-dsDNA antibody.
ANA levels: negative/positive and titer if positive.
Plasma complement levels C3 and C4.
Blood SED rate and CRP.
Anti-Smith, anti-Ro, anti-La, anti-cardiolipin (IgG, IgM): negative/positive.

2. Disease Activity and Quality of Life Scales

SELENA-SLEDAI score analyzed as raw data and absolute change from baseline.
BILAG score (A, B, C, D, E) at each visit for each organ-based system.
PGA score: value of the visual analogue scale in mm, analyzed as raw data and absolute change from baseline.
The Lupus-QoL total score ranging from 0 to 100 (see 16-1-9-sap [Appendix F]) was analyzed as raw data and absolute change from baseline.
FACIT-Fatigue total score (see 16-1-9-sap [Appendix G]) was analyzed as raw data and absolute change from baseline.

3. CXCR5 Receptor Occupancy on Peripheral B Cells

The following parameters for CXCR5 RO (%) were derived:
CXCR5 normalized RO %.
Duration of saturation of CXCR5 by SAR113244 in days from the first dosing, where saturation was defined as normalized RO >80% (based on the precision of the assay method: ±20%).

4. Serum CXCL13 Levels

Serum CXCL13 levels were analyzed using raw data, absolute and percentage change from baseline, the baseline value being the Day 1 predose value.

5. Peripheral Blood B and T Cell Subsets

Blood B and T cell subsets were analyzed as raw data, absolute and percentage change from baseline were performed centrally using flow cytometry.

6. Analysis

All analyses were descriptive only. No formal statistical testing was performed.

Descriptive statistics were provided by treatment group, using the number of available data, mean, SD, standard error of the mean (SEM), median, minimum and maximum, and 1st and 3rd quarter; the number of imputed values were also provided, if applicable. Categorical and ordinal data were summarized using the number and percentage of patients in each treatment group.

Time profile plots of mean (±SEM) raw data, absolute and/or percentage change from baseline (depending on the parameters) were also produced by treatment group for selected parameters.

For receptor occupancy data:
RO and normalized RO data were summarized by treatment group and visit using descriptive statistics (mean, median, minimum and maximum) and plots; individual plots produced if needed.
The duration of receptor saturation was described using the median, minimum and maximum by treatment group.
Selected individual data were listed.

Analyses of Safety Data

The safety evaluation was based upon the review of the individual values (clinically significant abnormalities) and descriptive statistics.

All safety analyses were performed using the safety population.

1. Adverse Events

Adverse events were coded according to MedDRA (version 18.1).

Adverse events were classified into predefined standard categories according to the following criteria:
Pretreatment AEs: AEs that occurred during the pretreatment phase.
Treatment-emergent AEs (TEAEs): AEs that occurred during the on-treatment phase.
Posttreatment AEs: AEs that occurred during the posttreatment phase.

All AEs reported in the study were listed and, if any, comments recorded on the eCRFs related to AEs were listed.

Treatment-emergent AEs were assigned to the treatment received prior to the time of the AE onset.

The following frequency distributions of TEAEs (incidence tables) were provided for the safety population:
Overview of TEAEs: Number and percentage of patients with TEAEs, severe TEAEs, and serious TEAEs, TEAEs leading to death, TEAEs leading to permanent treatment discontinuation, and treatment-emergent AESIs.
Summary of TEAEs by primary SOC and preferred term (PT):
Number and percentage of patients with at least 1 TEAE,
Number and percentage of patients and events.

All TEAEs irrespective of relationship to IMP were summarized by SOC.

Any deaths, SAEs, AEs leading to treatment discontinuation, or AESIs were listed.

2. Clinical Laboratory Evaluations

All individual data, including rechecked values, for planned hematology and biochemistry, were listed by biological function, patient and visit. If any, data from unscheduled laboratory tests were also listed. In these listings, individual data were flagged when lower or higher than the lower or upper laboratory limits and/or when reaching the absolute limit of potentially clinically significant abnormality (PCSA) criteria, when defined.

The values used as baselines were the Day 1 TOH (predose) assessment value. If any of the scheduled baseline tests were repeated for any patient, the last rechecked values were considered as baselines, provided they were performed before the first dose of IMP administration.

For parameters with laboratory ranges and/or abnormality criteria (PCSA), an on-treatment analysis was performed using all postbaseline assessments done during the on-treatment phase, including rechecked values. The number of patients with on-treatment abnormalities (PCSA) was provided stratified by baseline status (normal, abnormal), and presented by treatment group. This analysis was also performed for the out-of-normal laboratory range values.

All individual data, including rechecked values, for planned hematology and biochemistry, were listed by biological function. If any, data from unscheduled laboratory tests were also listed. In these listings, individual data were flagged when lower or higher than the lower or upper laboratory limits and/or when reaching the absolute limit of PCSA criteria, when defined.

A listing of individual postbaseline abnormalities by patient was provided.

A listing related to increase in ALT ≥2×ULN was also provided.

A listing of patients with combined PCSAs for liver function was also provided. All time points (planned and rechecked) of the study were reported for the concerned patient(s).

All qualitative and quantitative urinary test results (dipsticks), including rechecked values, were listed.

3. Vital Signs

Heart rate, SBP and DBP, and body weight were analyzed as raw parameter values and change from baseline.

Oral body temperature was analyzed as raw data.

The values used for baselines were the Day 1 TOH (predose) value, except for the body weight where the baseline was the Day −1 value. If any of the scheduled baseline tests were repeated for any patient, the rechecked values were considered as baselines, provided they were performed before the IMP administration.

For all parameters, an on-treatment analysis was performed using all postbaseline assessments done during the on-treatment phase, including rechecked values. The number of patients with on-treatment abnormalities (PCSA) were provided regardless of the normal or abnormal status of the baseline, and presented by treatment.

For heart rate, SBP, and DBP, raw data and changes from baseline were summarized in descriptive statistics, for each type of measurement, parameter, and time point by treatment.

For body weight, raw data and percentage changes from baseline were provided by treatment and scheduled time.

For oral body temperature, summaries of raw data were provided by treatment and scheduled time.

All individual data, including rechecked values, were listed. In the listings, values were flagged when reaching the limits of the PCSA criteria, when defined.

A separate listing of individual data from patients with postbaseline PCSAs was provided.

4. Electrocardiograms

The following parameters were received from the ECG reading center: HR, PR, QRS, QT, QTcB and QTcF, and analyzed.

The values used for baselines were the Day 1 TOH (predose) assessment values. If any of the scheduled baseline tests were repeated for any patient, the last rechecked value was considered as baseline, provided it was done before IMP administration.

All parameters were analyzed as raw data and absolute change from baseline. In addition, for the PCSA analysis, PR and QRS were also analyzed as percentage change from baseline.

For all parameters, an "on-treatment" analysis was performed on the safety population, using all assessments during the on-treatment phase, including any unplanned/rechecked values. Counts of patients with PCSAs were provided in summary tables regardless of the normal or abnormal status of the baseline. This table was presented by treatment.

Descriptive statistics (raw data and absolute change from baseline) were provided by visit and treatment group.

Patients with morphological assessments were summarized with comments sorted by High Level type of comments and by comments (ECG core lab code list).

The following listings were produced:

Individual raw data and absolute change from baseline for HR, PR, QRS, QT, QTcB, QTcF, Individual data of patients with any postbaseline PCSAs, Patients with QTcB/QTcF >480 ms and/or change from baseline in QTcB/QTcF >60 ms, Patients with at least one abnormality in qualitative assessment (i.e., abnormal 12-lead ECG) after the first dosing, and, All morphological comments.

5. Other Related Safety Parameters a. Anti-SAR113244 Antibodies

The ADA analysis was based on all patients randomized and treated with at least 1 evaluable postbaseline ADA sample (positive, negative or inconclusive). The ADA analyses were based on the baseline (Day 1 predose) and on all postbaseline ADA assessments during the treatment phase and during the follow-up observation period.

The following descriptive statistics were provided by treatment group and overall patients:

ADA status at baseline:

Number and percentage of patients with positive, negative or inconclusive ADA samples at baseline.

For patients with pre-existing ADA, descriptive statistics of the baseline titer.

ADA status during postbaseline period:

Number and percentage of patients with evaluable, positive, negative or inconclusive ADA samples.

For patients with positive ADA:

Descriptive statistics for the peak titer of patients with positive ADA,

For patients with negative ADA at baseline:

n (%) of patients with treatment-induced ADA,

Descriptive statistics for the peak titer of patients with treatment-induced ADA.

For patients with pre-existing ADA:

Descriptive statistics for the peak titer, n (%) of patients with treatment-boosted ADA, Descriptive statistics for the peak titer of patients with treatment-boosted ADA, Ratio in titer from baseline to postbaseline, X-fold increase in titer calculated as ratio of follow-up titer to baseline titer for patients with treatment-boosted ADA.

ADA prevalence,

ADA incidence.

b. Local Tolerability at Injection Site

Descriptive statistics of peak grade over the entire study or presence of at least one reaction during the entire study were summarized by treatment group.

All data were listed.

c. Serum Immunoglobulins

Serum IgA, IgD, IgM, IgE, and IgG were assessed.

Raw data, absolute and percentage changes from baseline were summarized using descriptive statistics by treatment and scheduled time point. The value used as baseline was the Day 1 predose assessment.

All data were listed.

d. Total Peripheral Blood B and T Cells

Raw data, absolute and percentage changes from baseline were summarized using descriptive statistics, by treatment and scheduled time point. The value to be used as the baseline was the Day 1 predose assessment.

All data were listed.

Due to operational issues in Cohort 1, total peripheral blood B and T cells were not measured during the study. Only screening values were available for Cohort 1.

Analyses of Pharmacokinetic Data

Plasma PK parameters and concentrations of SAR113244 were summarized by descriptive statistics (such as mean, geometric mean, median, SD, SEM, coefficient of variance (CV), minimum, and maximum) for each treatment.

For $C_{max}$ and $AUC_{0-4w}$, accumulation was assessed with a linear fixed effect model, Log(Ratio of Day 29 versus Day 1)=Dose+Error with dose as the fixed effect using SAS PROC MIXED.

The accumulation ratio of Day 29 versus Day 1 was assessed for each dose level separately as well as pooled across dose levels within the fixed effect model framework. The accumulation ratio was assessed by estimating the ratio of Day 29 versus Day 1 on the log scale with corresponding 90% confidence intervals (CIs), further converted to Day 29/Day 1 accumulation ratios with their corresponding 90% CIs using the antilog transformation.

Listings of individual accumulation ratios were provided, along with their descriptive statistics.

For $t_{1/2z}$, dose effect was assessed at Day 29 with a linear fixed effect model, Log($t_{1/2z}$)=Dose+Error The point estimate and 90% CI for the geometric mean of $t_{1/2z}$ were provided pooled across dose levels and separately for each dose group.

The distribution of $t_{max}$ values was represented by histogram plots for each dose level and day.

Dose proportionality for $C_{max}$ and $AUC_{0-4w}$ was assessed using pairwise comparisons for each parameter that was log-transformed. Point estimates and 90% CIs were provided.

Within-patient and total SDs for log($C_{max}$) and log($AUC_{0-4w}$) were estimated by equating observed and expected mean squares within the following linear mixed effects model framework:

Log(parameter)=Dose+Patient(Dose)+Day+Day*Dose+Error with Dose, Day and Day*Dose interaction as the fixed effects and Patient (Dose) as the random effect.

Interim Analyses

No interim analysis was performed.

Changes in the Conduct of the Study or Planned Analyses

Changes in the Conduct of the Study

There were 4 amendments to the protocol. The changes have been accounted for in the description of the study conduct throughout this report A summary of the changes included in the amendments are provided in Table 5.

TABLE 5

Summary of protocol amendments

| No. | Date | Purpose of amendments |
|---|---|---|
| 1 | 09-Oct-2014 | To optimize the protocol by adjusting the PD assessments to a minimum required in order to decrease constraints for the patients to be enrolled. Clinical scales assessments were streamlined to allow for a relevant timeframe of clinical assessment. Some inclusion/exclusion criteria were clarified/completed, and in particular E 28 exclusion criterion was refined as per request from the Ethics Committee in Berlin, in order to make the exclusion from study participation to all employees of the Sponsor and Investigator's site more explicit. Administrative modifications, clarifications as well as other minor changes to the protocol were added. |
| 2 | 08-Dec-2014 (Local for UK) | This protocol amendment was applicable in the United Kingdom only. To comply with the MHRA guidance on adequate contraception for a clinical trial, the list of MHRA approved contraception methods was provided in a local amendment to the protocol. In addition, this local amendment clarified that a decision to administer the same or a higher intermediate dose was intended to allow limited escalation (lower than the pre-specified "next higher" dose) only in the specific circumstance that the stopping rules were not met. |
| 3 | 10-Apr-2015 | At this stage, the recruitment of patients in Group 1 had been completed. The number of patients in cohort 2 and 3 was modified from 8 patients in each cohort (6 active, 2 placebo) to 16 patients (12 active, 4 placebo). Randomization was stratified according to plasmablasts/plasma cells at screening (<5% and ≥5% of total B cells, 1:1 ratio). Additional time points for assessment of peripheral B and C cell subsets (3 more samples), anti-SAR113244 antibodies (2 more samples), RNA (1 more sample), and exploratory biomarker analysis samples (2 more samples) were planned. The criterion I 02 related to body weight (between 50.0 and 95.0 kg) was removed. The exclusion criterion E 01 related to the disease severity was modified. SELENA-SLEDAI score was to be in the range of 2 to 9 (inclusion criterion) at screening and no further score was needed for the period before screening or during screening. |

TABLE 5-continued

Summary of protocol amendments

| No. | Date | Purpose of amendments |
|---|---|---|
| 4 | 12-Aug-2015 | This amendment was issued to update the use of vaccines during the study (all vaccines were prohibited) and to increase the upper limit permitted for body mass index in the inclusion criteria.<br>Following the increase of number of patients (cohort 2 and 3) introduced by amendment 3, the number of patients to be reviewed by the Data Safety Monitoring Board was corrected from "6 of 8" to "12 of 16". |

Changes in the Planned Analyses
From the Protocol to the Statistical Analysis Plan
The following main modifications to the statistical section of the protocol were as follows:
  Detailed PD analysis was included.
  The analysis of ECG data was updated to take into account the central reading of the data.
  The analysis of the anti-SAR113244 antibodies was updated according to the latest Sanofi analysis guideline.
  Some individual data listings were to be produced on demand.
After Database Lock
  Maximal receptor binding (normalized and non-normalized maximum RO %) and first time that maximum was achieved (normalized and non-normalized tmax [RO %]) were not calculated, as they were considered to be not relevant.
  The PK parameter tlast was not calculated.

Example 2

Study Patients

Disposition of Patients

As planned, 8 patients were enrolled into Cohort 1. It was planned to enroll 16 patients into Cohort 2 but due to recruitment difficulties, Cohort 2 was terminated prematurely following enrollment of 13 patients. The optional Cohort 3 (to administer the 800 mg dose) was not implemented because of preliminary indications that 500 mg was an appropriate dose level for SAR113244 moving forward. These decisions were not related to any concerns regarding safety or tolerability of SAR113244.

Of the 21 lupus patients randomized and treated in the study, 19 completed the study treatment period. A total of 16 patients received SAR113244 and 5 patients received placebo (Table 6).

TABLE 6

Patient Disposition-randomized population

|  | Placebo (N = 5) | SAR113244 | |
|---|---|---|---|
|  |  | 250 mg Q4W (N = 6) | 500 mg Q4W (N = 10) |
| Randomized and not treated | 0 | 0 | 0 |
| Randomized and treated | 5 (100.0%) | 6 (100.0%) | 10 (100.0%) |
| Complete the study treatment period | 5 (100.0%) | 5 (83.3%) | 9 (90.0%) |
| Did not complete the study treatment period | 0 | 1 (16.7%) | 1 (10.0%) |
| Subject's decision for treatment period discontinuation | 0 | 1 (16.7%) | 1 (10.0%) |
| Reason for treatment period discontinuation Other Reason: Subject withdrew consent Status at last study contact | 0 | 1 (16.7%) | 1 (10.0%) |
| Alive | 5 (100.0%) | 6 (100.0%) | 10 (100.0%) |

Note:
Percentages are calculated using the number of patients randomized as denominator Subject's request for treatment discontinuation is a separate category and is not additive with the reasons for discontinuation One patient receiving 250 mg SAR113244 Q4W and 1 patient receiving 500 mg SAR113244 Q4W withdrew their consent and discontinued from the study early.

Randomization and Dosing Irregularities

A total of 2 patients had minor protocol deviations relating to dosing irregularities.

Patient No. 276001024 and Patient No. 276001041 were already dosed with 500 mg SAR113244 Q4W before the investigator contacted the IWRS. However, it was confirmed on site by the unblinded CRA that the correct treatment was given as it was allocated later by the IWRS (i.e., no randomization error occurred).

Data Sets Analyzed

All 21 patients were included in the safety and PD populations and all patients who received SAR113244 were included in the PK population (Table 7).

TABLE 7

Analysis Populations-randomized population

|  | Placebo (N = 5) | SAR113244 250 mg Q4W (N = 6) | SAR113244 500 mg Q4W (N = 10) | All (N = 21) |
|---|---|---|---|---|
| Randomized population | 5 | 6 | 10 | 21 |
| Safety population | 5 | 6 | 10 | 21 |
| Pharmacokinetic population | 0 | 6 | 9 | 15 |
| Pharmacodynamic population* | 5 | 6 | 10 | 21 |

*Patients treated by placebo are not included in the analyses of receptor occupancy data Note:
All populations are tabulated according to the treatment actually received (as treated).

Demographic and Other Baseline Characteristics

Demography

Demographic characteristics at baseline are presented in Table 8.

TABLE 8

Summary of demographic and baseline characteristics - safety population

|  | Placebo (N = 5) | SAR113244 250 mg Q4W (N = 6) | SAR113244 500 mg Q4W (N = 10) | All (N = 21) |
|---|---|---|---|---|
| Age (years) | | | | |
| Number | 5 | 6 | 10 | 21 |
| Mean (SD) | 47.4 (5.6) | 41.8 (11.0) | 37.0 (12.0) | 40.9 (10.9) |
| Median | 47.0 | 44.5 | 36.0 | 43.0 |
| Min:Max | 40:55 | 23:55 | 22:54 | 22:55 |
| Age Group (years) [n (%)] | | | | |
| Number | 5 | 6 | 10 | 21 |
| <45 | 1 (20.0%) | 3 (50.0%) | 7 (70.0%) | 11 (52.4%) |
| [45-65[ | 4 (80.0%) | 3 (50.0%) | 3 (30.0%) | 10 (47.6%) |
| Sex [n (%)] | | | | |
| Number | 5 | 6 | 10 | 21 |
| Male | 2 (40.0%) | 0 | 0 | 2 (9.5%) |
| Female | 3 (60.0%) | 6 (100%) | 10 (100%) | 19 (90.5%) |
| Race [n (%)] | | | | |
| Number | 5 | 6 | 10 | 21 |
| Caucasian/White | 5 (100%) | 6 (100%) | 9 (90.0%) | 20 (95.2%) |
| Asian/Oriental | 0 | 0 | 1 (10.0%) | 1 (4.8%) |
| Weight (kg) | | | | |
| Number | 5 | 6 | 10 | 21 |
| Mean (SD) | 78.80 (10.70) | 67.52 (9.46) | 61.30 (12.16) | 67.24 (12.76) |
| Median | 77.90 | 66.40 | 58.95 | 65.30 |
| Min:Max | 65.3:92.4 | 56.1:84.0 | 50.6:92.1 | 50.6:92.4 |
| BMI (kg/m$^2$) | | | | |
| Number | 5 | 6 | 10 | 21 |
| Mean (SD) | 26.77 (2.84) | 23.47 (2.18) | 21.96 (4.11) | 23.54 (3.78) |
| Median | 26.63 | 22.46 | 20.55 | 22.60 |
| Min:Max | 22.6:30.5 | 21.9:27.4 | 18.4:32.6 | 18.4:32.6 |

TABLE 8-continued

Summary of demographic and baseline characteristics - safety population

| | | SAR113244 | | |
|---|---|---|---|---|
| | Placebo (N = 5) | 250 mg Q4W (N = 6) | 500 mg Q4W (N = 10) | All (N = 21) |
| BMI (kg/m$^2$) [n (%)] | | | | |
| Number | 5 | 6 | 10 | 21 |
| <30 | 4 (80.0%) | 6 (100%) | 9 (90.0%) | 19 (90.5%) |
| ≥30 | 1 (20.0%) | 0 | 1 (10.0%) | 2 (9.5%) |

At baseline, 1/5 (20.0%) patients receiving placebo were <45 years of age compared to 7/10 (70.0%) patients receiving 500 mg Q4W SAR113244. Three of 6 patients (50.0%) receiving 250 mg Q4W SAR113244 were <45 years of age.

The majority of patients (19/21) were female. All patients receiving SAR113244 were female and 3/5 (60.0%) patients receiving placebo were female. The majority of patients (20/21) were Caucasian/White and 1/21 patient receiving 500 mg Q4W SAR113244 was Asian/Oriental.

Medical and Surgical History

The most frequently reported medical or surgical history, other than SLE, were vascular hypertensive disorders which were reported in 8 patients across treatment groups. Age-related issues were reported in 5 patients across treatment groups. Depressive disorders, joint therapeutic procedures, and thyroid hypofunction disorders were reported in 4 patients each across treatment groups, and fat-soluble vitamin deficiencies and disorders were reported in 3 patients across treatment groups. All other medical or surgical history, other than SLE, was reported in 1 or 2 patients across treatment groups.

Disease Characteristics at Baseline

A summary of disease characteristics is presented in Table 9. A summary of BILAG scores at baseline are presented in Table 10.

TABLE 9

Summary of disease characteristics and other relevant baseline data - safety population

| | | SAR113244 | | |
|---|---|---|---|---|
| | Placebo (N = 5) | 250 mg Q4W (N = 6) | 500 mg Q4W (N = 10) | All (N = 21) |
| Duration of disease (years) | | | | |
| Number | 5 | 6 | 10 | 21 |
| Mean (SD) | 8.87 (8.29) | 15.35 (10.36) | 7.69 (8.30) | 10.16 (9.12) |
| Median | 7.42 | 13.04 | 4.69 | 7.42 |
| Q1:Q3 | 5.92:7.98 | 10.06:15.89 | 0.80:14.41 | 3.65:15.06 |
| Min:Max | 0.3:22.7 | 5.1:35.0 | 0.4:21.8 | 0.3:35.0 |
| Age at onset of diagnosis (years) | | | | |
| Number | 5 | 6 | 10 | 21 |
| Mean (SD) | 39.34 (12.83) | 26.82 (13.56) | 30.08 (12.52) | 31.36 (13.13) |
| Median | 41.00 | 31.96 | 24.96 | 32.00 |
| Q1:Q3 | 39.16:48.00 | 13.00:32.00 | 22.00:36.00 | 22.00:41.00 |
| Min:Max | 18.0:50.5 | 8.0:44.0 | 16.0:54.0 | 8.0:54.0 |
| Antinuclear antibody (ANA) test at screening (Charité CRO)* | | | | |
| Number | 5 | 6 | 10 | 21 |
| Positive | 5 (100%) | 6 (100%) | 10 (100%) | 21 (100%) |
| 1:160 | 1 (20.0%) | 0 | 2 (20.0%) | 3 (14.3%) |
| 1:320 | 0 | 3 (50.0%) | 2 (20.0%) | 5 (23.8%) |
| 1:640 | 0 | 1 (16.7%) | 1 (10.0%) | 2 (9.5%) |
| 1:1280 | 1 (20.0%) | 1 (16.7%) | 1 (10.0%) | 3 (14.3%) |
| 1:2560 | 2 (40.0%) | 0 | 4 (40.0%) | 6 (28.6%) |
| 1:3200 | 0 | 1 (16.7%) | 0 | 1 (4.8%) |
| 1:5120 | 1 (20.0%) | 0 | 0 | 1 (4.8%) |
| Antinuclear antibody (ANA) test at Day 1 predose (Covance) | | | | |
| Number | 5 | 6 | 10 | 21 |
| Negative | 1 (20.0%) | 0 | 0 | 1 (4.8%) |
| Positive | 4 (80.0%) | 6 (100%) | 10 (100%) | 20 (95.2%) |
| 1:40 | 0 | 0 | 2 (20.0%) | 2 (9.5%) |
| 1:80 | 0 | 3 (50.0%) | 1 (10.0%) | 4 (19.0%) |
| 1:160 | 1 (20.0%) | 3 (50.0%) | 4 (40.0%) | 8 (38.1%) |
| 1:320 | 1 (20.0%) | 0 | 2 (20.0%) | 3 (14.3%) |
| 1:640 | 2 (40.0%) | 0 | 1 (10.0%) | 3 (14.3%) |
| Anti-dsDNA antibodies titer (IU/mL) at screening (Charite | | | | |

TABLE 9-continued

Summary of disease characteristics and other relevant baseline data - safety population

| | | SAR113244 | | |
|---|---|---|---|---|
| | Placebo (N = 5) | 250 mg Q4W (N = 6) | 500 mg Q4W (N = 10) | All (N = 21) |
| CRO)* | | | | |
| Number | 5 | 6 | 10 | 21 |
| Number of imputed values | 1 | 1 | 1 | 3 |
| Mean (SD) | 8.7 (7.4) | 53.7 (77.9) | 62.5 (73.1) | 47.2 (66.6) |
| Median | 11.0 | 14.0 | 28.5 | 13.0 |
| Q1:Q3 | 2.2:12.0 | 5.0:84.0 | 12.0:131.0 | 5.0:50.0 |
| Min:Max | 0:18 | 5:200 | 1:200 | 0:200 |
| Anti-dsDNA antibodies titer (IU/mL) at Day 1 predose (Covance) | | | | |
| Number | 5 | 5 | 8 | 18 |
| Number of imputed values | 4 | 3 | 5 | 12 |
| Mean (SD) | 22.6 (19.2) | 125.8 (211.6) | 45.4 (51.1) | 61.4 (116.1) |
| Median | 14.0 | 14.0 | 14.0 | 14.0 |
| Q1:Q3 | 14.0:14.0 | 14.0:87.0 | 14.0:78.5 | 14.0:57.0 |
| Min:Max | 14:57 | 14:500 | 14:136 | 14:500 |
| Chest X-ray performed within 3 months | | | | |
| Number | 5 | 6 | 10 | 21 |
| No | 5 (100%) | 6 (100%) | 10 (100%) | 21 (100%) |
| Quantiferon(R)-TB GOLD | | | | |
| Number | 5 | 6 | 10 | 21 |
| Negative | 5 (100%) | 6 (100%) | 10 (100%) | 21 (100%) |
| SLEDAI total score at screening (Charité CRO)* | | | | |
| Number | 5 | 6 | 10 | 21 |
| Mean (SD) | 4.8 (1.8) | 6.3 (2.0) | 4.8 (2.5) | 5.2 (2.2) |
| Median | 6.0 | 7.0 | 4.0 | 6.0 |
| Q1:Q3 | 4.0:6.0 | 4.0:8.0 | 2.0:8.0 | 4.0:8.0 |
| Min:Max | 2:6 | 4:8 | 2:8 | 2:8 |
| SLEDAI total score at Day 1 predose (Covance) | | | | |
| Number | 5 | 6 | 10 | 21 |
| Mean (SD) | 6.0 (1.4) | 6.0 (1.8) | 5.2 (2.1) | 5.6 (1.9) |
| Median | 6.0 | 6.0 | 4.0 | 6.0 |
| Q1:Q3 | 6.0:6.0 | 4.0:8.0 | 4.0:6.0 | 4.0:6.0 |
| Min:Max | 4:8 | 4:8 | 4:10 | 4:10 |
| Physician global VAS (0-100 mm) at Day 1 | | | | |
| Number | 5 | 6 | 10 | 21 |
| Mean (SD) | 30.8 (10.9) | 28.2 (12.5) | 26.9 (11.5) | 28.2 (11.2) |
| Median | 34.0 | 29.5 | 26.0 | 28.0 |
| Q1:Q3 | 24.0:36.0 | 22.0:32.0 | 19.0:33.0 | 22.0:34.0 |
| Min:Max | 16:44 | 9:47 | 9:52 | 9:52 |
| Prednisone intake at screening Prednisone ongoing at screening | | | | |
| Yes | 2 (40.0%) | 4 (66.7%) | 6 (60.0%) | 12 (57.1%) |
| No | 3 (60.0%) | 2 (33.3%) | 4 (40.0%) | 9 (42.9%) |
| Total dose (mg) at screening | | | | |
| Number | 2 | 4 | 6 | 12 |
| Mean (SD) | 3.75 (1.77) | 6.88 (5.54) | 4.58 (1.02) | 5.21 (3.28) |
| Median | 3.75 | 5.00 | 5.00 | 5.00 |
| Q1:Q3 | 2.50:5.00 | 3.75:10.00 | 5.00:5.00 | 3.75:5.00 |
| Min:Max | 2.5:5.0 | 2.5:15.0 | 2.5:5.0 | 2.5:15.0 |

*Used for inclusion criteria
Imputed values (<LOQ) are replaced by LOQ/2 in all calculations
SELENA-SLEDAI: Safety of Estrogens in Systemic National Assessment-Systemic Lupus Erythematosus Disease Activity Index
VAS: visual assessment scale

TABLE 10

Summary of BILAG scores by system - safety population

| BILAG scores by system [n(%)] | Placebo (N = 5) | SAR113244 250 mg Q4W (N = 6) | SAR113244 500 mg Q4W (N = 10) | All (N = 21) |
|---|---|---|---|---|
| CONSTITUTIONAL | | | | |
| C | 0 | 2 (33.3%) | 1 (10.0%) | 3 (14.3%) |
| E | 5 (100%) | 4 (66.7%) | 9 (90.0%) | 18 (85.7%) |
| MUCOCUTANEOUS | | | | |
| B | 5 (100%) | 3 (50.0%) | 6 (60.0%) | 14 (66.7%) |
| C | 0 | 0 | 3 (30.0%) | 3 (14.3%) |
| E | 0 | 3 (50.0%) | 1 (10.0%) | 4 (19.0%) |
| NEUROPSYCHIATRIC | | | | |
| A | 0 | 1 (16.7%) | 0 | 1 (4.8%) |
| E | 5 (100%) | 5 (83.3%) | 10 (100%) | 20 (95.2%) |
| MUSCULOSKELETAL | | | | |
| B | 1 (20.0%) | 1 (16.7%) | 1 (10.0%) | 3 (14.3%) |
| C | 4 (80.0%) | 4 (66.7%) | 7 (70.0%) | 15 (71.4%) |
| E | 0 | 1 (16.7%) | 2 (20.0%) | 3 (14.3%) |
| CARDIORESPIRATORY | | | | |
| E | 5 (100%) | 6 (100%) | 10 (100%) | 21 (100%) |
| GASTROINTESTINAL | | | | |
| E | 5 (100%) | 6 (100%) | 10 (100%) | 21 (100%) |
| OPHTHALMIC | | | | |
| E | 5 (100%) | 6 (100%) | 10 (100%) | 21 (100%) |
| RENAL | | | | |
| E | 5 (100%) | 6 (100%) | 10 (100%) | 21 (100%) |
| HAEMATOLOGICAL | | | | |
| E | 5 (100%) | 6 (100%) | 10 (100%) | 21 (100%) |

Overall, mean disease duration was approximately 10 years. Mean disease duration of patients receiving placebo and of patients receiving 500 mg SAR113244 was approximately 9 and 8 years, respectively, and mean disease duration of patients receiving 250 mg SAR113244 was approximately 15 years.

All patients tested positive for ANA with a titer ≥1:160 at screening (measured by a local laboratory [Synlab]; these values were used for inclusion). One patient (in the placebo treatment group) tested negative for ANA at baseline, 6/20 patients tested positive for ANA with a titer ≤1:80 and 14/20 patients tested positive for ANA with a titer ≥1:160 at baseline. Baseline values were measured by Covance.

A total of 18/21 patients had positive titers for anti-dsDNA antibodies at screening (measured by Charité CRO) and 6/21 patients had positive titers for anti-dsDNA antibodies at baseline (measured by Covance).

Overall total SELENA-SLEDAI scores ranged from 2 to 8 at screening and from 4 to 10 at baseline. Overall PGA of disease activity ranged from 9 to 52 mm (100 mm indicates severe disease activity) on Day 1. A total of 12/21 (57.1%) patients were receiving ongoing treatment with prednisolone (total dose ranging from 2.5 to 15 mg) at screening.

All patients had negative QuantiFERON TB Gold test results at screening.

Prior and/or Concomitant Medication Taken for Lupus

Two of 5 (40.0%) patients receiving placebo, 4/6 (66.7%) patients receiving 250 mg Q4W SAR113244, and 7/10 (70.0%) patients receiving 500 mg Q4W SAR113244 were treated with corticosteroids for lupus during the study.

Four of 5 (80.0%) patients receiving placebo, 4/6 (66.7%) patients receiving 250 mg Q4W SAR113244, and 9/10 (90.0%) patients receiving 500 mg Q4W SAR113244 were treated with concomitant medications other than corticosteroids for lupus during the study. The most frequent of these concomitant medications were antiprotozoals, anti-inflammatory and antirheumatic products, and immunosuppressants.

Prior and/or Concomitant Medication not Related to Lupus

No patients were taking medications not related to lupus prior to the first dose of IMP.

Five of 5 (100%) patients receiving placebo, 5/6 (83.3%) patients receiving 250 mg Q4W SAR113244, and 8/10 (80.0%) patients receiving 500 mg Q4W SAR113244 were treated with concomitant medications not related to lupus during the study. The most frequent of these concomitant medications were vitamins, drugs for acid-related disorders, analgesics, and agents acting on the renin-angiotensin system.

Measurement of Treatment Compliance

All except the 2 patients who withdrew from the study before Day 29 received 2 IMP injections as planned.

Example 3

Pharmacodynamics Evaluation

Pharmacodynamics Endpoints
CXCR5 Receptor Occupancy on B Cells

Figure 2:
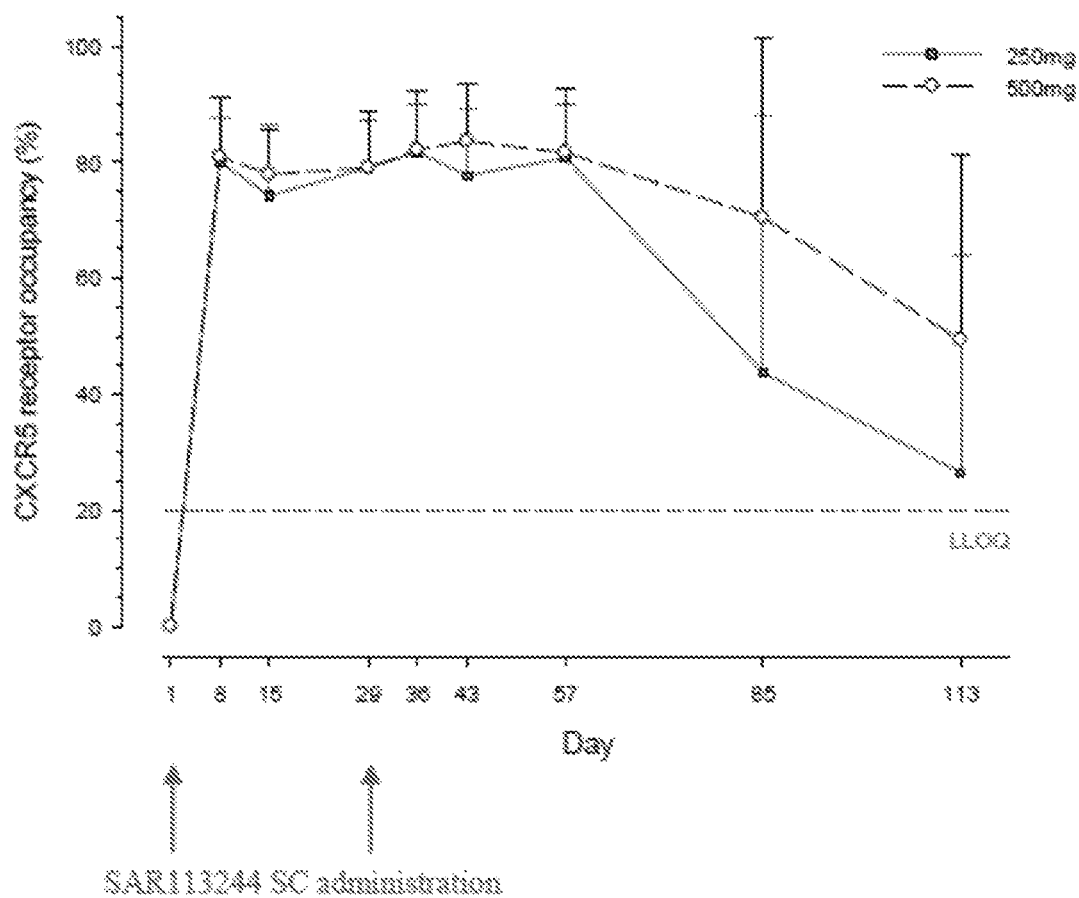
FIG. 2 is a graph showing the mean SAR113244 occupancy to CXCR5 on B lymphocytes cells in the peripheral blood versus time following a 1st dose and a 2nd dose of 250 mg and 500 mg of SAR113244.

Mean SAR113244 occupancy to CXCR5 on B cells in the peripheral blood versus time is presented in FIG. 2.

Individual RO values and their descriptive statistics are presented from Table 32 to Table 33. Patients treated with placebo were not included in the analyses of receptor occupancy data. The data from 6 patients for the 250 mg dose group and from 9 patients (Patient No. 276001019 was excluded) for the 500 mg dose group were included. A summary of these statistics are presented in Table 11.

CXCR5 occupancy was quantifiable after a single 250 mg and 500 mg SC administration of SAR113244 and plateaued from 7 days after the administration for all patients (Day 8 being the first sampling time point postdose), with comparable values. Eighty-four days after administration (i.e., 56 days after the second dose), a decrease of CXCR5 occupancy was observed for some patients in both groups going down to <LLOQ drug levels on CXCR5 (Patient Nos. 276001006, 276001014, and 276001024) whereas for most patients, CXCR5 were still occupied by the drug on Day 113 (EOS), as shown by the following:

RO % ranging between 53.7% and 78.9% for 2 out of 5 patients at 250 mg.
RO % ranging between 29.6% and 83.4% for 7 out of 9 patients at 500 mg.

Figure 3:
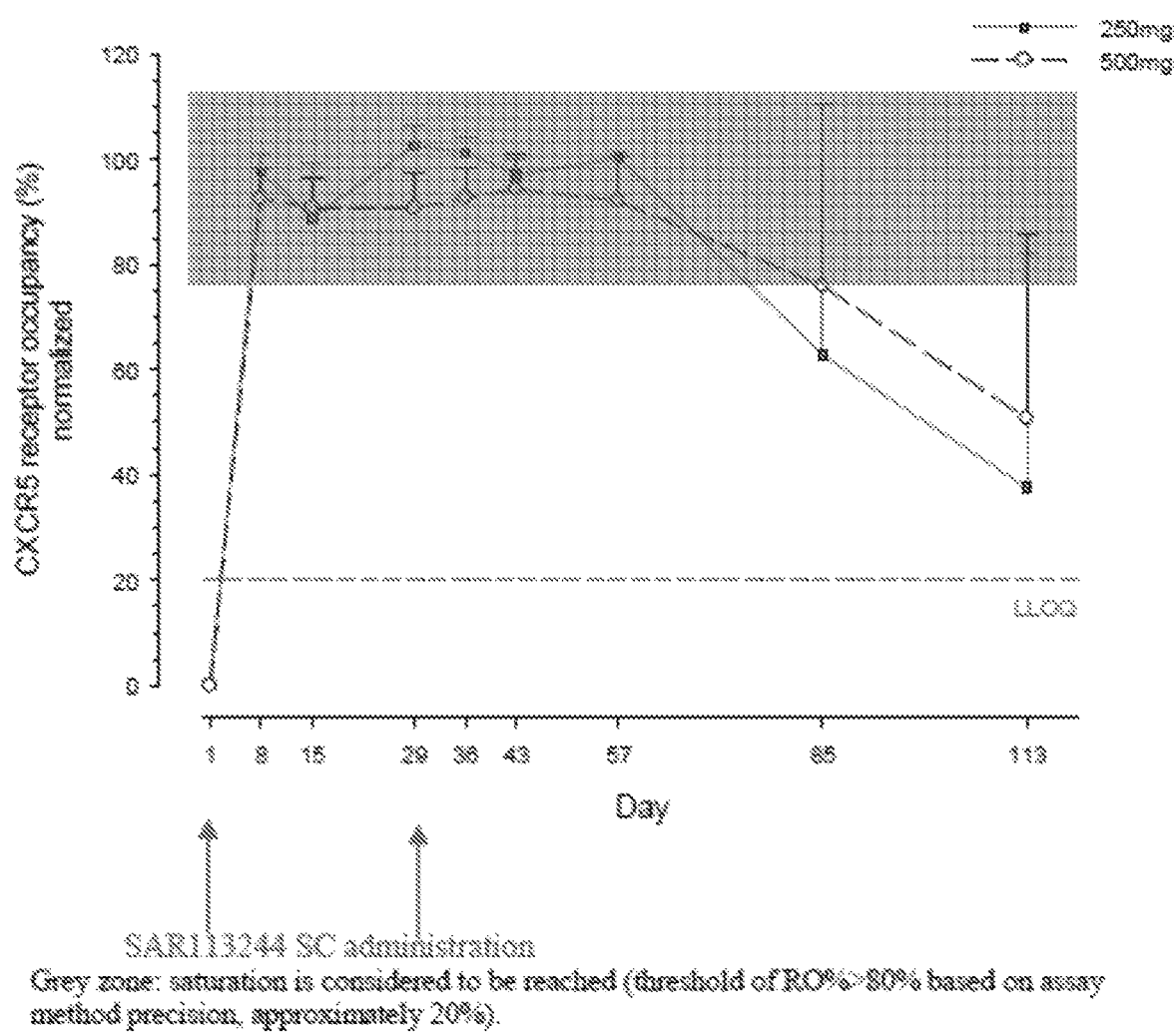
FIG. 3 is a graph showing the mean normalized SAR113244 occupancy to CXCR5 on peripheral blood B lymphocytes versus time following a 1st dose and a 2nd dose of 250 mg and 500 mg SAR113244.

In the RO assay, it was found that the maximal RO varied between patients. Thus, in order to standardize the maximal RO across the patients, individual RO results were normalized based on a normalization factor determined by spiking predose samples with saturating concentrations of SAR113244 for each patient (to determine the maximal RO achievable for each patient in the assay). Mean normalized SAR113244 binding to CXCR5 receptors on peripheral blood B cells versus time is presented in FIG. 3. The 'saturation duration' of normalized RO % was defined as the time interval during which the occupancy of CXCR5 by SAR113244 was maximal. Based on the precision of the assay method (i.e., +20%), maximal saturation of CXCR5 was reached when RO >80%.

Individual normalized RO values and their descriptive statistics are presented from Table 34 to Table 35. A summary of these statistics are presented in Table 12.

Individual values of duration of maximal occupancy and their descriptive statistics are presented in Table 36. A summary of these descriptive statistics are presented in Table 13.

TABLE 11

CXCR5 receptor occupancy in % (mean, median [min-max]) versus time following a 1st dose and a 2nd dose of 250 mg (n = 6) and 500 mg(n = 9) SAR113244

| Dose (mg) | RO % | | | | | | | | |
|---|---|---|---|---|---|---|---|---|---|
| | Day 1* | Day 8 | Day 15 | Day 29** | Day 36 | Day 43 | Day 57 | Day 85 | Day 113 |
| 250 | <LOQ, <LOQ | 79.9, 83.0 | 74.2, 80.0 | 79.0, 79.2 | 81.7, 83.8 | 77.7, 79.8 | 80.7, 82.4 | 43.7, 42.4 | 26.5, <LOQ |
| | [<LOQ-<LOQ]$^a$ | [66.0-83.9]$^a$ | [54.2-85.2] | [71.4-86.2]$^b$ | [71.0-88.1]$^b$ | [63.5-87.7]$^b$ | [67.8-90.2]$^b$ | [<LOQ-90.3]$^a$ | [<LOQ-78.9]$^a$ |
| 500 | <LOQ, <LOQ | 80.9, 82.5 | 77.9, 79.3 | 79.0, 75.8 | 82.1, 82.0 | 83.6, 81.2 | 81.6, 83.7 | 70.4, 77.6 | 49.3, 62.6 |
| | [<LOQ-<LOQ]$^c$ | [67.3-98.4]$^c$ | [66.2-86.4]$^d$ | [70.9-98.3]$^d$ | [66.3-97.8]$^c$ | [68.7-98.3]$^d$ | [65.8-98.4]$^c$ | [<LOQ-96.6]$^c$ | [<LOQ-83.4] |

$^a$n = 5;
$^b$n = 4;
$^c$n = 8;
$^d$n = 7
*sampling before the 1$^{st}$ dose,
**sampling before the 2$^{nd}$ dose

TABLE 12

Normalized CXCR5 receptor occupancy in % (mean, median [min-max]) versus time following a 1st dose and a 2nd dose of 250 mg (n = 6) and 500 mg (n = 9) SAR113244

| Dose (mg) | Normalized_RO % | | | | | | | | |
|---|---|---|---|---|---|---|---|---|---|
| | Day 1* | Day 8 | Day 15 | Day 29** | Day 36 | Day 43 | Day 57 | Day 85 | Day 113 |
| 250 | <LOQ, <LOQ | 97.7, 97.2 | 88.8, 89.7 | 103, 105 | 101, 100 | 97.0, 97.7 | 100, 99.9 | 62.7, 74.5 | 37.5, 30.6 |
| | [<LOQ-<LOQ]$^a$ | [94.5-101]$^a$ | [77.8-103]$^a$ | [98.1-105]$^b$ | [99.1-105]$^b$ | [93.6-99.8]$^b$ | [99.0-102]$^b$ | [<LOQ-102]$^c$ | [<LOQ-89.0]$^c$ |
| 500 | <LOQ, <LOQ | 92.5, 93.2 | 90.8, 91.9 | 90.7, 91.2 | 92.7, 94.4 | 94.3, 96.9 | 92.0, 96.6 | 75.9, 85.0 | 50.7, 66.6 |
| | [<LOQ-<LOQ]$^d$ | [82.4-99.3]$^e$ | [82.8-97.5]$^f$ | [79.4-99.2]$^e$ | [81.5-98.7]$^e$ | [81.8-99.3]$^f$ | [79.2-99.3]$^e$ | [<LOQ-99.1]$^e$ | [<LOQ-85.8]$^d$ |

$^a$n = 5;
$^b$n = 3;
$^c$n = 4;
$^d$n = 8;
$^e$n = 7;
$^f$n = 6
*sampling before the 1$^{st}$ dose
**sampling before the 2$^{nd}$ dose

TABLE 13

Descriptive statistics (median, [min-max]) on saturation duration relative to the 2nd dose following a SC administration of 250 mg (n = 4) and 500 mg (n = 6) SAR113244

| Dose (mg) | Saturation duration relative to the 2$^{nd}$ dose over the study (Day) |
|---|---|
| 250 | 42, [28-84] |
| 500 | 56, [28-84] |

Saturation of CXCR5 by SAR113244 occurred by 7 days (1st RO sampling time postdose) after the 1st dose for all patients at 250 mg and 500 mg. Over the study, the duration of saturation relative to the 2nd dose was 42 days as median value at 250 mg and appeared to increase to 56 days as median value at 500 mg.

CXCR5 occupancy started to decrease 84 days after the 1st dose for some patients with a normalized RO %<LLOQ in 2 patients (Patient Nos. 276001006 and 276001024). At 112 days after the 1st dose, normalized RO % decrease continued, although detectable CXCR5 RO by SAR113244 was observed for some patients: normalized RO % ranged between 34.1% and 75.5% for 6 patients mainly at the 500 mg dose level, and for Patient Nos. 276001011 and 276001041, saturation of CXCR5 occupancy was still observed with normalized RO % of 89.0% and 85.8%, respectively. Patient distribution according to different normalized RO % ranges is presented in Table 14.

TABLE 14

Patient distribution according to different normalized RO % ranges on Day 85 (ie Day 57 after the 2nd dose) and Day 113 (ie Day 85 after the 2nd dose), after two 250 mg (n = 4) and 500 mg (n = 8) SAR113244 doses

| Dose | | Number of patients | |
|---|---|---|---|
| (mg) | Norm RO % | Day 85 | Day 113 |
| 250 | <LLOQ | 1 | 2 |
|  | [20%-80%] | 1 | 1 |
|  | >80% ie, CXCR5 saturation | 2 | 1 |
| 500$^a$ | <LLOQ | 1 | 2 |
|  | [20%-80%] | 1 | 5 |
|  | >80% ie, CXCR5 saturation | 5 | 1 |

$^a$n = 7 on Day 85;
LLOQ = 20%

Disease-Related Markers
Anti-dsDNA Antibody

One patient in the 250 mg SAR113244 treatment group (Patient No. 276001003) and 1 patient in the 500 mg SAR113244 treatment group (Patient No. 276001024) had abnormally high values for anti-dsDNA antibodies at baseline. Values remained above the ULN throughout the study in both patients.

Almost no changes in terms of mean percentage change from baseline were observed across treatment groups in the anti-dsDNA antibody values at each of the scheduled visits.

ANA Levels

In the placebo treatment group, ⅘ (80%) patients tested positive for ANA on Day 1 (⅖ with a titer of 1:640, ⅕ with a titer of 1:160, and ⅕ with a titer of 1:320), and ⅘ (100%) patients tested positive for ANA on Day 113 (⅕ with a titer of 1:40, ⅕ with a titer of 1:160, ⅕ with a titer of 1:320, ⅕ with a titer of 1:640, and ⅕ with a titer of 1:2560).

All patients in the 250 mg and 500 mg SAR113244 treatment group with analyzable samples tested positive for ANA on both Day 1 and Day 113.

In the 250 mg SAR113244 treatment group, at Day 1, 3/6 patients had a titer of 1:80 and 3/6 patients had a titer of 1:160. At Day 113, 1 patient's sample was missing, ⅕ patients had a titer of 1:40, ⅕ patients had a titer of 1:80, ⅕ patients had a titer of 1:160, and ⅖ patients had a titer of 1:320.

In the 500 mg SAR113244 treatment group, at Day 1, 2/10 patients had a titer of 1:40, 1/10 patients had a titer of 1:80, 4/10 patients had a titer of 1:160, 2/10 patients had a titer of 1:320, and 1/10 patients had a titer of 1:640. At Day 113, 1/10 patients had a titer of 1:40, 5/10 patients had a titer of 1:160, 2/10 patients had a titer of 1:320, 1/10 patients had a titer of 1:640, and 1/10 patients had a titer of 1:2560.

Plasma Complement Levels C3 and C4

One of 5 patients in the placebo treatment group had abnormal baseline plasma complement levels C3. Four of 6 patients in the 250 mg SAR113244 treatment group had abnormal baseline plasma complement levels C3, and 3/6 patients had abnormal baseline plasma complement levels C4. Five of 9 patients in the 500 mg SAR113244 treatment group had abnormal baseline plasma complement levels C3, and 3/9 patients had abnormal baseline plasma complement levels C4.

There did not appear to be any treatment- or dose-related trends in mean percentage change from baseline in plasma complement levels C3 or C4 at each of the scheduled visits or in normalization of the C3 or C4 values.

Blood SED Rate and CRP

One of 5 patients in the placebo treatment group and 1/6 patients in the 250 mg SAR113244 had an abnormal blood SED rate at baseline. Two of 10 patients in the 500 mg SAR113244 treatment groups had abnormal blood SED rates at baseline and 1/10 patients had an abnormal CRP value at baseline.

There did not appear to be any treatment- or dose-related trends in mean percentage change from baseline in blood SED rate or CRP from baseline to each of the scheduled visits.

Anti-Smith, Anti-Ro/SS-A, Anti-La/SS-B, Anti-Cardiolipin Antibodies

Not every patient had an analyzable sample for the assessment of anti-Smith, anti-Ro, anti-La, and anti-cardiolipin antibodies.

All patients with analyzable samples in the placebo treatment group and the 500 mg SAR113244 treatment group tested negative for the anti-Smith antibody on Day 1 and Day 113. Four of 5 (80.0%) patients in the 250 mg SAR113244 treatment group tested negative for the anti-Smith antibody on Day 1 and all patients in the 250 mg SAR113244 treatment group with analyzable samples tested negative for the Smith antibody on Day 113. On Days 1 and 113, ⅗ (60.0%) patients and 2/4 (50.0%) patients, respectively, in the placebo treatment group tested negative for the anti-Ro/SS-A antibody. On Days 1 and 113, ⅘ (80.0%) patients in the 250 mg SAR113244 treatment group tested negative for the anti-Ro/SS-A antibody. On Days 1 and 113, ⅞ (87.5%) patients and 8/10 (80.0%) patients, respectively, in the 500 mg SAR113244 treatment group tested negative for the anti-Ro/SS-A antibody.

On Days 1 and 113, ⅘ (80.0%) patients and ¾ (75%) patients, respectively, in the placebo treatment group tested negative for the anti-La/SS-B antibody. All patients with analyzable samples in the 250 mg SAR113244 treatment group tested negative for the anti-La/SS-B antibody on both Day 1 and Day 113. On Days 1 and 113, 7/8 (87.5%) patients and 9/10 (90.0%) patients, respectively, in the 500 mg SAR113244 treatment group tested negative for the anti-La/SS-B antibody.

All patients with analyzable samples in the placebo and 250 mg SAR113244 treatment groups tested negative for anti-cardiolipin antibody (IgG) on Days 1 and 113. On Day 1, 8/9 (88.9%) patients in the 500 mg SAR113244 treatment group tested negative for the anti-cardiolipin antibody (IgG) and 1/9 (11.1%) patient tested positive. On Day 113, 9/10 (90.0%) patients in the 500 mg SAR113244 treatment group tested negative for the anti-cardiolipin antibody (IgG), and 1/10 (10.0%) patient tested positive.

All patients with analyzable samples across treatment groups tested negative for the anti-cardiolipin antibody (IgM) on Day 1 and Day 113.

Disease Activity and Quality of Life Scales

Mean total SELENA-SLEDAI scores were similar across treatment groups throughout the study, and ranged from 0 to 10. Mean changes from baseline in total score were all <1.3 throughout the study for all treatment groups.

BILAG Scores at baseline compared to Day 113 were similar. SAR113244 did not appear to have any effect on BILAG scores.

Mean PGA scores were similar across treatment groups from baseline to Day 113. In the 500 mg SAR113244 treatment group, mean change from baseline in PGA score at Day 113 was an increase of 8.8 in the 500 mg SAR113244 treatment group compared to a decrease of 5.6 and an increase of 0.5 in the placebo and 250 mg SARI 13244 treatment groups, respectively.

Lupus-QoL total scores at baseline compared to Day 113 were similar. SAR113244 did not appear to have any effect on Lupus-QoL scores.

FACIT-Fatigue total scores at baseline compared to Day 113 were similar. SAR113244 did not appear to have any effect on FACIT-Fatigue scores.

Serum CXCL13 Levels

No treatment- or dose-related trends were apparent in the CXCL13 data from the time of baseline to Day 113.

Peripheral Blood B and T Cell Subsets

B Cell Subsets

The frequencies of different B cell subsets were examined.

Following dosing with SAR113244 and placebo, several B cell subsets were examined by flow cytometry. Frequencies were determined out of the lymphocytes expressing CD20. For naïve B cells (CD19+CD27-IgD+), the mean percentage ranged from approximately 59.8% to 64.7% across all postbaseline time points (baseline ranged from 62.0% to 64.5%). For pre-switch memory B cells (CD19+CD27+IgD+), the mean percentage ranged from approximately 6.0% to 8.1% (baseline ranged from 6.5% to 7.9%). For post-switch memory B cells (CD19+CD27+IgD-), the mean percentage ranged from approximately 19.8% to 23.3% (baseline ranged from 19.8% to 21.5%). For double-negative memory B cells (CD19+CD27-IgD-), the mean percentage ranged from approximately 7.4% to 10.6% (baseline ranged from 8.7% to 9.2%).

The baseline percentage of cells expressing CXCR5 for each subset is as follows: naïve B cells 98.4% to 99.2%; pre-switch memory B cells 98.1% to 99.1%; post-switch memory B cells 94.1% to 94.2%; and double-negative memory B cells 63.5% to 79.2%.

Following dosing with SAR113244 on Day 1, a decrease in unoccupied CXCR5 by SAR113244 was observed at Day 8 (first visit postdose) in the 500 mg SAR113244 treatment group and at Day 15 (first visit postdose) in the 250 mg SAR113244 treatment group. Maximal occupancy appeared to continue to Day 85 (last available time point) in the 500 mg SAR113244 treatment group and Day 43 in the 250 mg SAR113244 treatment group; by Day 85, RO appeared to be returning to baseline levels.

Following dosing with 250 mg Q4W SAR113244 on Day 1, of the lymphocytes expressing CD19, the frequency of CD19+CD20+ cells appeared to decrease until Day 15 (baseline: 94.6%, Day 15: 81.0%) and then steadily increase from Day 15 to Day 85 (Day 29: 84.3%, Day 43: 86.7%) returning to levels similar to those observed at baseline (Day 85: 92.0%). The frequency of CD19+CD20-CD27++ cells (antibody-secreting cells), following dosing with 250 mg Q4W SAR113244 on Day 1, appeared to increase transiently in some patients, returning by Day 85 to levels similar to those observed at baseline. These B cell subsets did not appear to be consistently affected by SAR113244 in the 500 mg SAR113244 treatment group.

T Cell Subsets

The frequencies of total T cells and T cell subsets were determined.

Following dosing with SAR113244 and placebo, several T cell subsets were examined by flow cytometry. Frequencies were determined out of the lymphocytes expressing CD3. For helper T cells (CD4+), the mean percentage ranged from approximately 51.4% to 70.5% across all postbaseline time points (baseline ranged from 53.6% to 69.5%). For cytotoxic T cells (CD8+), the mean percentage ranged from approximately 21.0% to 38.8% across all postbaseline time points (baseline ranged from 22.1% to 38.9%).

For naïve T cells (CD45RA+CCR7+), of the CD4+ cells, the mean percentage ranged from approximately 41.9% to 50.5% across all postbaseline time points (baseline ranged from 44.8% to 49.0%); of the CD8+ cells, the mean percentage ranged from approximately 38.8% to 53.3% across all postbaseline time points (baseline ranged from 45.8% to 52.4%).

For central memory T cells (CD45RA-CCR7+), of the CD4+ cells, the mean percentage ranged from approximately 25.0% to 30.0% across all postbaseline time points (baseline ranged from 24.9% to 28.1%); of the CD8+ cells, the mean percentage ranged from approximately 3.3% to 8.5% across all postbaseline time points (baseline ranged from 3.6% to 9.0%).

For effector memory T cells (CD45RA-CCR7-), of the CD4+ cells, the mean percentage ranged from approximately 19.9% to 26.6% across all postbaseline time points (baseline ranged from 21.4% to 26.9%), of the CD8+ cells, the mean percentage ranged from approximately 18.2% to 35.2% across all postbaseline time points (baseline ranged from 16.1% to 28.7%).

The mean percentage of CD4+ cells that expressed CXCR5 at baseline ranged from approximately 8.7% to 17.2%.

Pharmacodynamics Conclusions

Saturation of CXCR5 by SAR113244 was observed 7 days after the first dose for all patients at 250 mg and 500 mg SAR113244. The duration of saturation relative to the second dose was of 42 days as median value at 250 mg, and appeared to increase to 56 days as median value at 500 mg. For both dose groups, normalized RO % had decreased out of the saturation zone by Day 113 in 10/12 patients (in some patients to <LLOQ), although normalized RO %>80% was still observed in 2 patients on Day 113.

SAR113244 had no consistent effect on disease activity and QoL scales, serum CXCL13, auto-antibody levels, complement levels, or on B cell or T cell subsets. A transient increase in antibody-secreting cells was noted in some patients following the 250 mg dose SAR113244, but a similar degree of increase was not observed after the 500 mg dose SAR113244.

Example 4

Safety Evaluation

Extent of Exposure

All patients apart from Patient No. 276001003 (receiving 250 mg SAR113244) and Patient No. 276001019 (receiving 500 mg SAR113244) received the intended doses of SAR113244 or placebo. Patient No. 276001003 withdrew consent following the first administration due to personal reasons and only received 1 dose of 250 mg SAR113244 on Day 1. Patient No. 276001019 also withdrew consent following the first administration and only received 1 dose of placebo on Day 1.

All other patients received 2 doses of SAR113244 or placebo on Days 1 and 29 as intended (Table 15).

TABLE 15

Summary of extent of exposure - safety population

| Number of IMP injections | Placebo (N = 5) | SAR113244 | |
|---|---|---|---|
| | | 250 mg Q4W (N = 6) | 500 mg Q4W (N = 10) |
| 1 | 0 | 1 (16.7%) | 1 (10.0%) |
| 2 | 5 (100%) | 5 (83.3%) | 9 (90.0%) |

Note:
Patients are considered in the treatment group they actually received (as treated)

Adverse Events
Brief Summary of Adverse Events

Overall, 16/21 patients (3/5 patients receiving placebo, 4/6 patients receiving 250 mg SAR113244 and 9/10 patients receiving 500 mg SAR113244) experienced at least 1 TEAE (Table 16). A total of 52 TEAEs were reported throughout the study.

There were no deaths or severe TEAEs, and no discontinuations of treatment due to TEAEs. One SAE occurred during the study in a patient receiving placebo.

Three patients in the SAR113244 treatment groups experienced AESIs of injection site erythema and 1 patient in the placebo treatment group experienced an AESI of increased ALT.

TABLE 16

Overview of treatment-emergent adverse events - safety population

| n (%) | Placebo (N = 5) | SAR113244 | |
|---|---|---|---|
| | | 250 mg Q4W (N = 6) | 500 mg Q4W (N = 10) |
| Patients with any TEAE | 3 (60.0%) | 4 (66.7%) | 9 (90.0%) |
| Patients with any severe TEAE | 0 | 0 | 0 |
| Patients with any treatment emergent SAE | 1 (20.0%) | 0 | 0 |
| Patients with any treatment emergent AE of special interest (AESI) | 1 (20.0%) | 2 (33.3%) | 1 (10.0%) |
| Patients with any TEAE leading to permanent treatment discontinuation | 0 | 0 | 0 |
| Patients with any TEAE leading to death | 0 | 0 | 0 |

TEAE: Treatment emergent adverse event,
SAE: Serious adverse event
N = Number of patients treated within each group,
n (%) = number and % of patients with at least one TEAE in each category
Note:
An adverse event is considered as treatment emergent if it occurred from the time of the first investigational medicinal product (IMP) administration up to the end of study visit (included)
PGM = PRODOPS/SAR113244/TDR11407/CSR/REPORT/PGM/ae_aeover_s_t.sas
OUT = REPORT/OUTPUT/ae_aeover_s_t_i.rtf (26AUG2016-13:27)

Display of Adverse Events

The number and percentage of patients with TEAEs by treatment, primary SOC, and PT are summarized in Table 17.

TABLE 17

Number (%) of patients with TEAE(s) by Primary SOC and PT - safety population

| Primary system organ class Preferred term [n (%)] | Placebo (N = 5) | SAR113244 | |
|---|---|---|---|
| | | 250 mg Q4W (N = 6) | 500 mg Q4W (N = 10) |
| Any class | 3 (60.0%) | 4 (66.7%) | 9 (90.0%) |
| Infections and infestations | 3 (60.0%) | 1 (16.7%) | 5 (50.0%) |
| Nasopharyngitis | 3 (60.0%) | 1 (16.7%) | 5 (50.0%) |
| Influenza | 1 (20.0%) | 0 | 0 |
| Nervous system disorders | 2 (40.0%) | 1 (16.7%) | 4 (40.0%) |
| Headache | 2 (40.0%) | 1 (16.7%) | 3 (30.0%) |
| Dizziness postural | 0 | 1 (16.7%) | 1 (10.0%) |
| Respiratory, thoracic and mediastinal disorders | 0 | 0 | 1 (10.0%) |
| Oropharyngeal pain | 0 | 0 | 1 (10.0%) |
| Gastrointestinal disorders | 1 (20.0%) | 0 | 2 (20.0%) |
| Abdominal pain | 0 | 0 | 1 (10.0%) |
| Dyspepsia | 0 | 0 | 1 (10.0%) |
| Nausea | 1 (20.0%) | 0 | 1 (10.0%) |
| Vomiting | 1 (20.0%) | 0 | 0 |
| Skin and subcutaneous tissue disorders | 0 | 1 (16.7%) | 0 |
| Erythema | 0 | 1 (16.7%) | 0 |
| Pruritus | 0 | 1 (16.7%) | 0 |
| Musculoskeletal and connective tissue disorders | 1 (20.0%) | 0 | 1 (10.0%) |
| Back pain | 0 | 0 | 1 (10.0%) |
| Pain in extremity | 1 (20.0%) | 0 | 0 |
| Reproductive system and breast disorders | 1 (20.0%) | 0 | 0 |
| Postmenopausal haemorrhage | 1 (20.0%) | 0 | 0 |
| General disorders and administration site conditions | 0 | 3 (50.0%) | 2 (20.0%) |
| Injection site erythema | 0 | 3 (50.0%) | 2 (20.0%) |
| Injection site oedema | 0 | 1 (16.7%) | 0 |

TABLE 17-continued

Number (%) of patients with TEAE(s) by Primary SOC and
PT - safety population

|  |  | SAR113244 | |
| --- | --- | --- | --- |
| Primary system organ class<br>Preferred term [n (%)] | Placebo<br>(N = 5) | 250 mg<br>Q4W<br>(N = 6) | 500 mg<br>Q4W<br>(N = 10) |
| Investigations | 1 (20.0%) | 0 | 0 |
| Alanine aminotransferase increased | 1 (20.0%) | 0 | 0 |
| Injury, poisoning and procedural complications | 0 | 1 (16.7%) | 1 (10.0%) |
| Procedural dizziness | 0 | 1 (16.7%) | 1 (10.0%) |

TEAE: Treatment emergent adverse event,
SOC: System organ class,
PT: Preferred term MedDRA 19.0
N = Number of patients treated within each group,
n (%) = number and % of patients with at least one TEAE in each category
Note:
Table sorted by SOC internationally agreed order and decreasing frequency of PT in SAR113244 500 mg Q4W group.
Note:
An adverse event is considered as treatment emergent if it occurred from the time of the first investigational medicinal product (IMP) administration up to the end of study visit (included)

Analysis of Adverse Events

The most frequently reported TEAEs (reported in >2 patients) were nasopharyngitis and headache, reported in all treatment groups, and injection site erythema, reported only in patients receiving SAR113244. Postural dizziness, procedural dizziness, and nausea were each reported in 2 patients, and all other TEAEs were single occurrences.

There did not appear to be any dose-related trends in the type or incidence of AEs reported. Other than injection site erythema, there were no treatment-related trends in the type or incidence of AEs reported.

Three of 6 (50%) patients in the 250 mg SAR113244 treatment group reported 7 AEs of injection site erythema, and 2/10 (20%) patients in the 500 mg SAR113244 treatment group reported 3 AEs of injection site erythema. No patients receiving placebo experienced injection site erythema or edema.

The TEAEs of injection site erythema in Patient Nos. 276001003 and 276001011 in the 250 mg SAR113244 treatment group, and Patient No. 276001041 in the 500 mg SAR113244 treatment group each lasted for over 24 hours and were, therefore, reported as AESIs.

Deaths and Serious Adverse Events and Other Significant Adverse Events

Deaths

There were no deaths reported during the study.

Serious Adverse Events

One SAE occurred during the study.

Patient No. 276001048 in the placebo treatment group experienced postmenopausal hemorrhage. Fractionated abrasion under hysteroscopy was performed to treat the SAE, without complications. This SAE was considered moderate in intensity and not related to the IMP. Study treatment was not changed as a result of this SAE.

Adverse Events Leading to Withdrawal and Other Significant Adverse Events

There were no TEAEs leading to withdrawal from the study.

Patient Nos. 276001003 and 276001011 in the 250 mg SAR113244 treatment group, and Patient No. 276001041 in the 500 mg SAR113244 treatment group experienced TEAEs of injection site erythema lasting >24 hours. All were considered mild in intensity and related to the IMP.

Patient No. 276001048 in the placebo treatment group experienced an AESI of increased ALT. The AE was considered mild in intensity and not related to the IMP.

Clinical Laboratory Evaluations

Red Blood Cells, Platelets, and Coagulation

Overall, 3 patients experienced PCSAs for hematocrit compared to normal baseline values (1 patient in the placebo treatment group and 2 patients in the 500 mg SAR113244 treatment group).

White Blood Cells

Overall, 1 patient reported postbaseline PCSAs for neutrophils compared to a normal baseline value in the 500 mg SAR113244 treatment group. Four patients reported postbaseline PCSAs for basophils compared to normal baseline values (2 patients in the 250 mg SAR113244 treatment group and 2 patients in the 500 mg SAR113244 treatment group). One PCSA for monocytes compared to a normal baseline value was reported in 1 patient in the 500 mg SAR113244 treatment group.

Metabolism

Overall, 1 PCSA for creatine phosphokinase compared to a normal baseline value was reported in 1 patient in the 500 mg SAR113244 treatment group. Two PCSAs for glucose were reported in 2 patients in the 500 mg SAR113244 treatment group; 1 patient had a normal baseline value and 1 patient's baseline value was missing.

Electrolytes

No PCSAs for electrolytes were reported in any treatment group (Table 37).

Renal Function

Overall, 3 patients reported PCSAs for creatinine (>30% increase from baseline) compared to normal baseline values (2 patients in the placebo treatment group and 1 patient in the 500 mg SAR113244 treatment group).

TABLE 18

Red blood cells, platelets and coagulation - Number of patients with abnormalities (PCSA) during the TEAE period according to baseline status - safety population

|  | Placebo<br>(N = 5) | | 250 mg<br>Q4W<br>(N = 6) | | SAR113244<br>500 mg Q4W<br>(N = 10) | |
| --- | --- | --- | --- | --- | --- | --- |
| Laboratory parameter<br>PCSA criteria n/N1 | Nor.<br>bas. | Abn.<br>bas. | Nor.<br>bas. | Abn.<br>bas. | Nor.<br>bas. | Abn.<br>bas. |
| Hemoglobin | | | | | | |
| Decr. from B ≥20 g/L | 0/5 | na | 0/6 | na | 0/10 | na |
| ≤115 g/L (Male); ≤95 g/L (Female) | 0/5 | na | 0/6 | na | 0/10 | na |
| ≥185 g/L (Male); ≥165 g/L (Female) | 0/5 | na | 0/6 | na | 0/10 | na |

TABLE 18-continued

Red blood cells, platelets and coagulation - Number of patients with abnormalities (PCSA) during the TEAE period according to baseline status - safety population

| | | | SAR113244 | | | |
|---|---|---|---|---|---|---|
| | Placebo (N = 5) | | 250 mg Q4W (N = 6) | | 500 mg Q4W (N = 10) | |
| Laboratory parameter PCSA criteria n/N1 | Nor. bas. | Abn. bas. | Nor. bas. | Abn. bas. | Nor. bas. | Abn. bas. |
| Red blood cells (erythrocytes) | | | | | | |
| ≥6 Tera/L | 0/2 | 0/3 | 0/3 | 0/3 | 0/7 | 0/3 |
| Platelet count (thrombocyte count) | | | | | | |
| <100 Giga/L | 0/5 | 0/0 | 0/6 | 0/0 | 0/10 | 0/0 |
| ≥700 Giga/L | 0/5 | 0/0 | 0/6 | 0/0 | 0/10 | 0/0 |
| Hematocrit | | | | | | |
| ≤0.37 v/v (Male); ≤0.32 v/v (Female) | 1/5 (20.0%) | 0/0 | 0/6 | 0/0 | 2/9 (22.2%) | 1/1 (100%) |
| ≥0.55 v/v (Male); ≥0.5 v/v (Female) | 0/5 | 0/0 | 0/6 | 0/0 | 0/9 | 0/1 |

PCSA: Potentially Clinically Significant Abnormalities (Version of 2014-05-24)

LLN/ULN: Lower/Upper Limit of Normal range,

B: Baseline,

Nor. bas.: Normal baseline,

Abn. bas.: Abnormal baseline (LLN/ULN or PCSA), na: not applicable n/N1 = Number of patients who met the criterion at least once/number of patients within each group who had that parameter assessed Note:

A PCSA is considered to be on-treatment if it occurred from the time of the first investigational medicinal product (IMP) administration up to the end of study visit (included).

For hemoglobin, baseline values < LLN or > ULN (or LLN/ULN missing) are counted in one unique group (ie as normal).

TABLE 19

White blood cells - Number of patients with abnormalities (PCSA) during the TEAE period according to baseline status - safety population

| | | | SAR113244 | | | |
|---|---|---|---|---|---|---|
| | Placebo (N = 5) | | 250 mg Q4W (N = 6) | | 500 mg Q4W (N = 10) | |
| Laboratory parameter PCSA criteria n/N1 | Nor. bas. | Abn. bas. | Nor. bas. | Abn. bas. | Nor. bas. | Abn. bas. |
| White blood cell count (leukocyte count) | | | | | | |
| <3.0 Giga/L (Non-Black); <2.0 Giga/L (Black) | 0/5 | 0/0 | 0/6 | 0/0 | 0/10 | 0/0 |
| ≥16.0 Giga/L | 0/5 | 0/0 | 0/6 | 0/0 | 0/10 | 0/0 |
| Neutrophils | | | | | | |
| <1.5 Giga/L (Non-Black); <1.0 Giga/L (Black) | 0/5 | 0/0 | 0/5 | 0/1 | 1/10 (10.0%) | 0/0 |
| Eosinophils | | | | | | |
| >0.5 Giga/L or > ULN (if ULN ≥0.5 Giga/L) | 0/5 | 0/0 | 0/6 | 0/0 | 0/10 | 0/0 |
| Basophils | | | | | | |
| >0.1 Giga/L | 0/5 | 0/0 | 2/6 (33.3%) | 0/0 | 2/10 (20.0%) | 0/0 |

TABLE 19-continued

White blood cells - Number of patients with abnormalities (PCSA) during the TEAE period according to baseline status - safety population

| Laboratory parameter PCSA criteria n/N1 | Placebo (N = 5) | | SAR113244 | | | |
|---|---|---|---|---|---|---|
| | | | 250 mg Q4W (N = 6) | | 500 mg Q4W (N = 10) | |
| | Nor. bas. | Abn. bas. | Nor. bas. | Abn. bas. | Nor. bas. | Abn. bas. |
| Lymphocytes | | | | | | |
| >4.0 Giga/L | 0/5 | 0/0 | 0/3 | 0/3 | 0/9 | 0/1 |
| Monocytes | | | | | | |
| >0.7 Giga/L | 0/5 | 0/0 | 0/6 | 0/0 | 1/10 (10.0%) | 0/0 |

PCSA: Potentially Clinically Significant Abnormalities (Version of 2014-05-24)
LLN/ULN: Lower/Upper Limit of Normal range,
B: Baseline,
Nor. bas.: Normal baseline,
Abn. bas.: Abnormal baseline (LLN/ULN or PCSA)
n/N1 = Number of patients who met the criterion at least once/number of patients within each group who had that parameter assessed
Note:
A PCSA is considered to be on-treatment if it occurred from the time of the first investigational medicinal product (IMP) administration up to the end of study visit (included).
For eosinophils, basophils and monocytes, values < LLN (or LLN missing) are counted as normal.

TABLE 20

Metabolism - Number of patients with abnormalities (PCSA) during the TEAE period according to baseline status - safety population

| Laboratory parameter PCSA criteria n/N1 | Placebo (N = 5) | | SAR113244 | | | |
|---|---|---|---|---|---|---|
| | | | 250 mg Q4W (N = 6) | | 500 mg Q4W (N = 10) | |
| | Nor. bas. | Abn. bas. | Nor. bas. | Abn. bas. | Nor. bas. | Abn. bas. | Mis. bas. |
| Glucose | | | | | | | |
| ≤3.9 mmol/L and < LLN | 0/5 | 0/0 | 0/6 | 0/0 | 1/9 (11.1%) | 0/0 | 1/1 (100%) |
| ≥11.1 mmol/L (unfasted); ≥7 mmol/L (fasted) | 0/5 | 0/0 | 0/6 | 0/0 | 0/9 | 0/0 | 0/1 |
| Total cholesterol | | | | | | | |
| ≥7.74 mmol/L | 0/5 | 0/0 | 0/6 | 0/0 | 0/10 | 0/0 | 0/0 |
| Triglycerides | | | | | | | |
| ≥4.6 mmol/L | 0/4 | 1/1 (100%) | 0/6 | 0/0 | 0/10 | 0/0 | 0/0 |
| Creatine phospho kinase | | | | | | | |
| >3 ULN | 0/5 | 0/0 | 0/6 | 0/0 | 1/10 (10.0%) | 0/0 | 0/0 |
| >10 ULN | 0/5 | 0/0 | 0/6 | 0/0 | 0/10 | 0/0 | 0/0 |
| Albumin | | | | | | | |
| ≤25 g/L | 0/5 | 0/0 | 0/6 | 0/0 | 0/10 | 0/0 | 0/0 |

PCSA: Potentially Clinically Significant Abnormalities (Version of 2014-05-24)
LLN/ULN: Lower/Upper Limit of Normal range,
Nor. bas.: Normal baseline,
Abn. bas.: Abnormal baseline (LLN/ULN or PCSA)
n/N1 = Number of patients who met the criterion at least once/number of patients within each group who had that parameter assessed
Note:
A PCSA is considered to be on-treatment if it occurred from the time of the first investigational medicinal product (IMP) administration up to the end of study visit (included).
For CPK, values < LLN (or LLN missing) are counted as normal.

TABLE 21

Renal function - Number of patients with abnormalities (PCSA) during the TEAE period according to baseline status - safety population

| Laboratory parameter | Placebo (N = 5) | | 250 mg Q4W (N = 6) | | 500 mg Q4W (N = 10) | |
|---|---|---|---|---|---|---|
| PCSA criteria n/N1 | Nor. bas. | Abn. bas. | Nor. bas. | Abn. bas. | Nor. bas. | Abn. bas. |
| Creatinine | | | | | | |
| ≥150 μmol/L (Adults) | 0/5 | 0/0 | 0/6 | 0/0 | 0/10 | 0/0 |
| ≥30% change from B | 2/5 (40.0%) | na | 0/6 | na | 1/10 (10.0%) | na |
| ≥100% change from B | 0/5 | na | 0/6 | na | 0/10 | na |
| Urea | | | | | | |
| ≥17 mmol/L | 0/5 | 0/0 | 0/6 | 0/0 | 0/10 | 0/0 |

PCSA: Potentially Clinically Significant Abnormalities (Version of 2014-05-24)
LLN/ULN: Lower/Upper Limit of Normal range,
B: Baseline,
Nor. bas.: Normal baseline,
Abn. bas.: Abnormal baseline (LLN/ULN or PCSA),
na: not applicable
n/N1 = Number of patients who met the criterion at least once/number of patients within each group who had that parameter assessed
Note:
A PCSA is considered to be on-treatment if it occurred from the time of the first investigational medicinal product (IMP) administration up to the end of study visit (included).
For percent change creatinine, baseline values < LLN or > ULN (or LLN/ULN missing) are counted in one unique group (ie as normal).

Liver Function

No PCSAs for liver function were reported in any treatment group

Vital Signs, Physical Findings and Other Safety Observations

Individual Clinically Relevant Abnormalities

Overall, several PCSAs for vital signs parameters occurred during the TEAE period (including patients dosed with placebo).

One patient in the 500 mg SAR113244 treatment group (Patient No. 276001036) had a PCSA of weight loss. On Day 29, the patient's weight was 11% lower than the baseline value. This was not associated with any TEAE and her body weight had increased by the next time point (change from baseline at Day 57 was −3.7%).

There were several PCSAs for blood pressure values. None were associated with TEAEs and the PCSAs occurred across treatment groups. No dose- or treatment-related trends were apparent in the vital signs data from the time of baseline to Day 113.

TABLE 22

Vital signs - Number of patients with abnormalities (PCSA) during the TEAE period -

| Vital signs parameter PCSA criteria n/N1 | Placebo (N = 5) | SAR113244 250 mg Q4W (N = 6) | 500 mg Q4W (N = 10) |
|---|---|---|---|
| Systolic blood pressure | | | |
| ≤95 mmHg and decr. from B ≥20 mmHg | 0/5 | 0/6 | 1/10 (10.0%) |
| ≥160 mmHg and incr. from B ≥20 mmHg | 0/5 | 0/6 | 0/10 |
| Diastolic blood pressure | | | |
| ≤45 mmHg and decr. from B ≥10 mmHg | 0/5 | 0/6 | 0/10 |
| ≥110 mmHg and incr. from B ≥10 mmHg | 0/5 | 0/6 | 0/10 |
| Orthostatic systolic blood pressure | | | |
| ≤−20 mmHg | 1/5 (20.0%) | 2/6 (33.3%) | 1/10 (10.0%) |
| Orthostatic diastolic blood pressure | | | |
| ≤−10 mmHg | 1/5 (20.0%) | 0/6 | 2/10 (20.0%) |
| Heart rate | | | |
| ≤50 bpm and decr. from B ≥20 bpm | 0/5 | 0/6 | 0/10 |
| ≥120 bpm and incr. from B ≥20 bpm | 0/5 | 0/6 | 0/10 |
| Weight | | | |
| ≥5% decr. from B | 0/5 | 0/6 | 1/10 (10.0%) |
| ≥5% incr. from B | 0/5 | 0/6 | 0/10 |

PCSA: Potentially Clinically Significant Abnormalities (Version of 2014 May 24)
decr./incr.: decrease/increase,
B: Baseline
n/N1 = Number of patients who met the criterion at least once/number of patients within each group who had that parameter assessed
Note:
A PCSA is considered to be on-treatment if it occurred from the time of the first investigational medicinal product (IMP) administration up to the end of study visit (included).
Orthostatic = standing after 3 minutes - supine after 10 minutes.

Electrocardiograms
Individual Clinically Relevant Abnormalities

A listing of data for patients with postbaseline PCSAs for ECG parameters is provided in Table.

Potentially clinically significant abnormalities in heart rate were only reported in the SAR113244 treatment groups. There appears to be a treatment- and dose-related trend in increased heart rate values as 3/10 (30%) patients receiving 500 mg Q4W SAR113244 had heart values >90 bpm compared to only 1/6 (16.7%) patients receiving 250 mg Q4W SAR113244, and no patients receiving placebo. However, only 1 patient receiving 500 mg Q4W SAR113244 had an increase from baseline ≥20 bpm.

A total of 5/6 (83.3%) patients receiving 250 mg Q4W SAR113244 and 5/10 (50%) patients receiving 500 mg Q4W SAR113244 had QTcB values >450 ms, compared to 1/5 (20%) patients receiving placebo. A total of 2/6 (33.3%) patients receiving 250 mg Q4W SAR113244 and 2/10 (20%) patients receiving 500 mg Q4W SAR113244 had QTcF values >450 ms. No patients receiving placebo had QTcF values >450 ms.

Only one patient experienced a change from baseline >30 ms in QTcB. Patient No. 276001006 in the 250 mg SAR113244 treatment group had QTcB and QTcF values of 491 ms and 460 ms, respectively, at T3H postbaseline on Day 1 (Table 39). The QTcB value had increased by 39 ms from baseline. This was not associated with any TEAE.

No QTcF >480 ms or increases from baseline in QTc interval >60 ms were observed.

TABLE 23

ECG - Number of patients with abnormalities (PCSA) during the TEAE period - safety population

| ECG parameter<br>PCSA criteria n/N1 | Placebo<br>(N = 5) | SAR113244 | |
|---|---|---|---|
| | | 250 mg Q4W<br>(N = 6) | 500 mg Q4W<br>(N = 10) |
| Heart rate | | | |
| <50 bpm | 0/5 | 1/6 (16.7%) | 0/10 |
| <50 bpm and decr. from B ≥20 bpm | 0/5 | 0/6 | 0/10 |
| <40 bpm | 0/5 | 0/6 | 0/10 |
| >90 bpm | 0/5 | 1/6 (16.7%) | 3/10 (30.0%) |
| >90 bpm and incr. from B ≥20 bpm | 0/5 | 0/6 | 1/10 (10.0%) |
| >100 bpm | 0/5 | 0/6 | 0/10 |
| PR interval | | | |
| >200 ms | 1/5 (20.0%) | 1/6 (16.7%) | 0/10 |
| >200 ms and incr. from B ≥25% | 0/5 | 0/6 | 0/10 |
| >220 ms | 0/5 | 0/6 | 0/10 |
| QRS interval | | | |
| >110 ms | 1/5 (20.0%) | 0/6 | 1/10 (10.0%) |
| >110 ms and incr. from B ≥25% | 0/5 | 0/6 | 0/10 |
| >120 ms | 0/5 | 0/6 | 0/10 |
| QT interval | | | |
| >500 ms | 0/5 | 0/6 | 0/10 |
| QTc Bazett | | | |
| >450 ms | 1/5 (20.0%) | 5/6 (83.3%) | 5/10 (50.0%) |
| >480 ms | 0/5 | 1/6 (16.7%) | 0/10 |
| >500 ms | 0/5 | 0/6 | 0/10 |
| QTc Bazett - change from baseline | | | |
| Incr. from B ]30-60] ms | 0/5 | 1/6 (16.7%) | 0/10 |
| Incr. from B >60 ms | 0/5 | 0/6 | 0/10 |
| QTc Fridericia | | | |
| >450 ms | 0/5 | 2/6 (33.3%) | 2/10 (20.0%) |
| >480 ms | 0/5 | 0/6 | 0/10 |
| QTc Fridericia - change from baseline | | | |
| Incr. from B ]30-60] ms | 0/5 | 0/6 | 0/10 |
| Incr. from B >60 ms | 0/5 | 0/6 | 0/10 |

Morphological Assessments

Electrocardiogram morphological assessments are summarized in Table 24.

All individual abnormalities reported were considered to be not clinically significant.

The change from baseline to Day 113 in B cell (CD19) and T cell (CD3) levels following dosing with placebo or treatment with 500 mg SAR113244 was comparable. No treatment-related trends were apparent in the frequency of total peripheral blood B and T cells.

TABLE 24

Summary of ECG morphological assessments - safety population

| High level type of comment Comment [n (%)] | Placebo Pre-dose[a] (N = 5) | Placebo Post-dose[b] (N = 5) | SAR 250 mg Pre-dose[a] (N = 6) | SAR 250 mg Post-dose[b] (N = 6) | SAR 500 mg Pre-dose[a] (N = 10) | SAR 500 mg Post-dose[b] (N = 10) |
|---|---|---|---|---|---|---|
| RHYTHM ANALYSIS | | | | | | |
| DOMINANT SINUS RHYTHM | 0 | 0 | 0 | 1 (16.7%) | 0 | 1 (10.0%) |
| NORMAL SINUS RHYTHM, RATE 50-100 BPM | 5 (100%) | 5 (100%) | 6 (100%) | 6 (100%) | 10 (100%) | 10 (100%) |
| PREMATURE ATRIAL COMPLEXES CONDUCTED OR NON CONDUCTED | 0 | 0 | 0 | 0 | 0 | 1 (10.0%) |
| PREMATURE VENTRICULAR COMPLEXES | 0 | 0 | 1 (16.7%) | 1 (16.7%) | 0 | 0 |
| SINUS BRADYCARDIA, RATE 40-49 BPM T/U WAVE | 0 | 0 | 0 | 1 (16.7%) | 0 | 0 |
| NORMAL REPOLARIZATION PATTERN | 5 (100%) | 5 (100%) | 6 (100%) | 6 (100%) | 10 (100%) | 10 (100%) |

[a]ECG performed up to Day 1 predose included
[b]ECG performed after Day 1 predose
n (%) = Number and % of patients with at least one event in each category Local Tolerability at Injection Site No injection site pain was reported during the study. One of 6 (16.7%) patients in the 250 mg SAR113244 treatment group experienced an injection site itch which was reported as "hardly perceptible".

One of 6 (16.7%) patients in the 250 mg SAR113244 treatment group experienced injection site edema which was considered mild in intensity. This event was reported as a TEAE.

Three of 6 (50%) patients in the 250 mg SAR113244 treatment group, and 2/10 (20%) patients in the 500 mg SAR113244 treatment group experienced TEAEs of injection site erythema. All were considered mild in intensity. The TEAEs of injection site erythema in Patient Nos. 276001003 and 276001011 (250 mg SAR113244), and Patient No. 276001041 (500 mg SAR113244) each lasted for over 24 hours and were, therefore, reported as AESIs.

Serum Immunoglobulins

Mean increase in IgA levels from baseline to Day 113 was 492.0 mg/L (SD 242.9) in the placebo treatment group; 370.0 mg/L (SD 351.2) in the 250 mg SAR113244 treatment group; and 83.0 mg/L (SD 395.4) in the 500 mg SAR113244 treatment group.

Mean decrease in IgE levels from baseline to Day 113 was −13.66 ku/L (SD 45.58) in the placebo treatment group; −63.87 ku/L (SD 169.93) in the 250 mg SAR113244 treatment group; and −41.81 ku/L (221.27) in the 500 mg SAR113244 treatment group.

Mean increase in IgM levels from baseline to Day 113 was 190.0 mg/L (SD 63.6) in the placebo treatment group; 128.3 mg/L (SD 147.2) in the 250 mg SAR113244 treatment group; and 45.0 mg/L (91.2) in the 500 mg SAR113244 treatment group.

SAR113244 did not appear to have an effect on IgD or IgG.

Total Peripheral Blood B and T Cells

No data are available for Cohort 1 (250 mg SAR113244) postbaseline as total peripheral blood B and T cells were not measured due to operational difficulties.

Safety Conclusions

SAR113244 was generally safe and well tolerated when administered to male and female lupus patients at doses of 250 g and 500 mg Q4W as 2 injections.

The most frequently reported TEAEs (reported in >2 patients) were nasopharyngitis and headache, reported in all treatment groups, and injection site erythema, reported only in patients receiving SAR113244. Postural dizziness, procedural dizziness, and nausea were each reported in 2 patients, and all other TEAEs were single occurrences. There did not appear to be any dose-related trends in the type or incidence of AEs reported.

There were a few PCSAs for laboratory assessments and vital signs both in patients treated with SAR113244 and the placebo group, with no dose- or treatment-related trends. Few PCSAs for heart rate and QTcF were reported only in patients receiving SAR113244. No QTcF values >480 ms or QTcF increase from baseline >30 ms were reported in any patient.

Injection site reactions such as erythema (in 5 patients) and itch (in 1 patient) were reported among the 16 patients receiving SAR113244, with no dose relationship. All events of injection site erythema were of mild intensity.

SAR113244 had no relevant effect on the level of peripheral blood total B and T cells, or immunoglobulins IgA, IgD, IgE, IgG, or IgM.

Example 5

Pharmacokinetic Evaluation

All blood samples were collected within ±15% of the sampling times scheduled in the protocol for SAR113244, which had no impact on the results as actual times were used for PK analysis.

SAR113244 plasma concentrations were below the LLOQ in all predose samples on Day 1, for each dose level.

Patient No. 276001019 (500 mg SAR113244 treatment group) was not included in the PK population as concentration data were considered insufficient to be interpretable; the patient did not attend the Day 15 visit because she withdrew her consent and permanently discontinued study treatment on Day 28.

Plasma Concentrations

Figure 4:
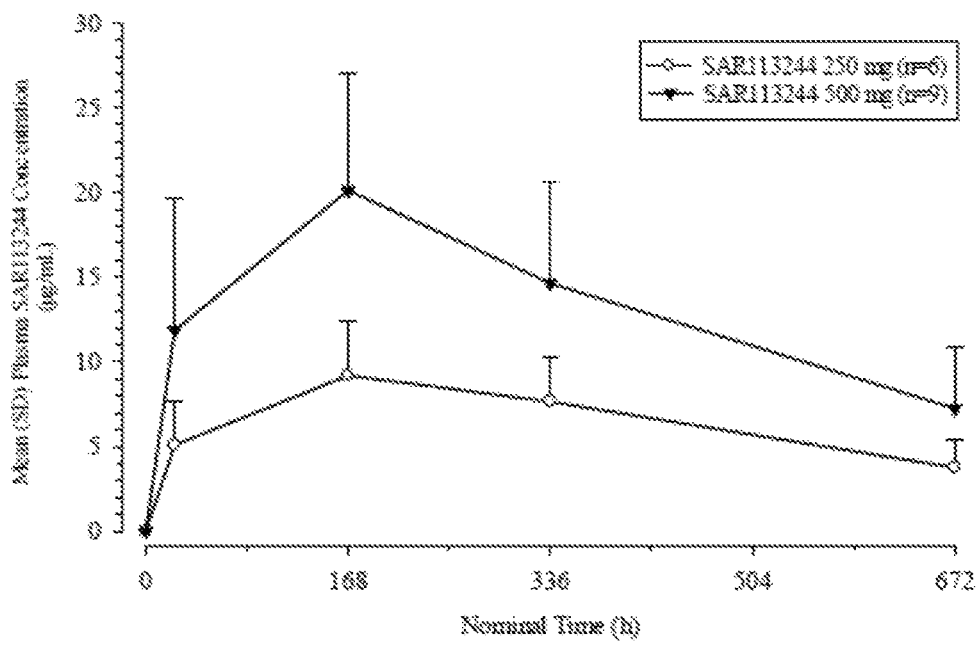
FIG. 4 is a graph showing the (SD) SAR113244 plasma concentration-time profiles after the 1st dose of SAR113244 in linear scale (top) and log-linear scale (bottom).
Figure 4:
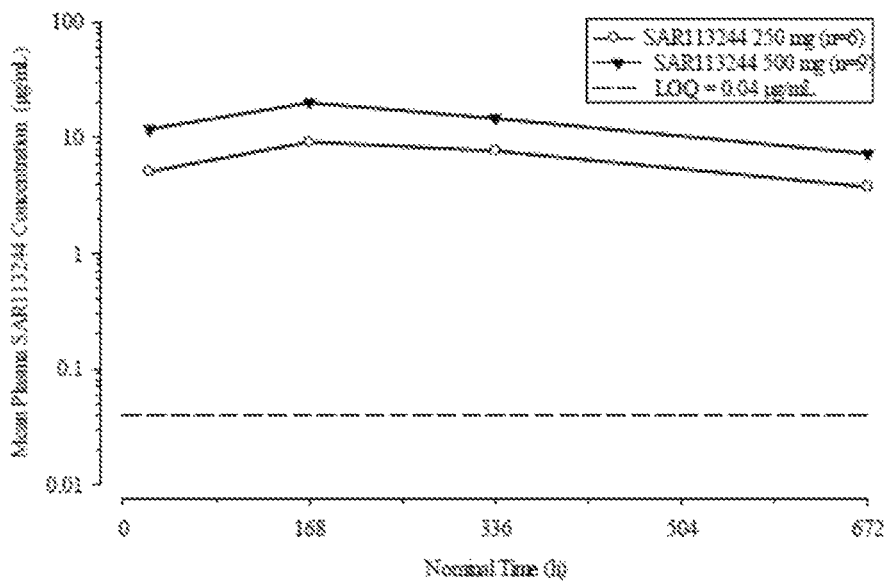
Figure 5:
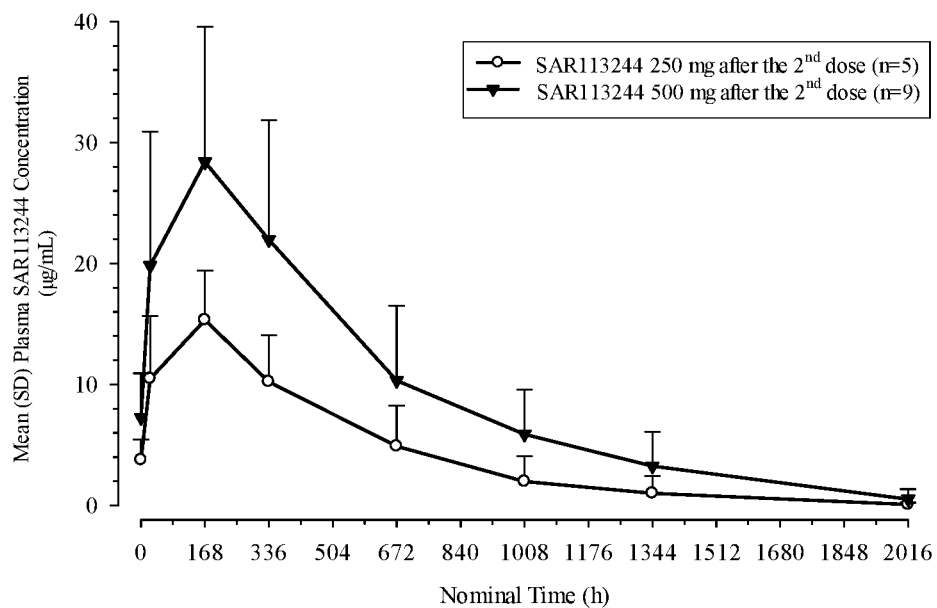
FIG. 5 is a graph showing mean (SD) SAR113244 plasma concentration-time profiles after the 2nd dose of SAR113244 in linear scale (top) and log-linear scale (bottom).
Figure 5:
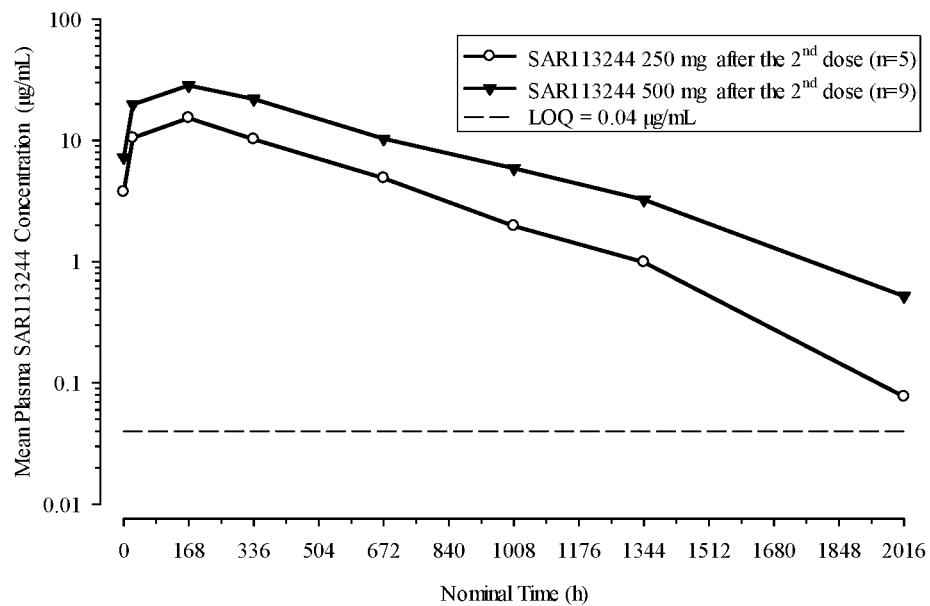

Mean (SD) SAR113244 plasma concentration-time profiles for each dose group after the first dose and the second dose are shown in FIG. 4 and FIG. 5, respectively.

Pharmacokinetic Parameters

Individual SAR113244 plasma PK parameters after the first and the second dose are summarized in Table 25 and Table 26, respectively.

TABLE 25

SAR113244 plasma pharmacokinetic parameters after the 1st dose of SAR113244

| Mean ± SD | Plasma SAR113244 | |
|---|---|---|
| (Geometric Mean) [CV %] | 250 mg | 500 mg |
| N | 6 | 9 |
| $C_{max}$ | 9.37 ± 3.06 | 21.3 ± 7.28 |
| (µg/mL) | (9.02) [32.7] | (20.1) [34.1] |
| $t_{max}{}^a$ | 168.90 | 167.95 |
| (h) | (167.85-337.53) | (24.00-168.95) |
| $AUC_{0-4W}$ | 4410 ± 1560 | 9040 ± 3300 |
| (µg · h/mL) | (4220) [35.3] | (8470) [36.5] |

$^a$Median (Min-Max)

Profile of Subject 276001019 was excluded

Source = PKS Study: TDR11407;

Scenario: P-X-A-EV-OD, Version 11

Date/Time = 9/13/2016 3:29:37 PM

TABLE 26

SAR113244 plasma pharmacokinetic parameters after the 2nd dose of SAR113244

| Mean ± SD | Plasma SAR113244 | |
|---|---|---|
| (Geometric Mean) [CV %] | 250 mg Q4W | 500 mg Q4W |
| N | 5 | 9 |
| $C_{max}$ | 15.3 ± 4.09 | 28.6 ± 11.5 |
| (µg/mL) | (14.9) [26.7] | (26.4) [40.2] |
| $t_{max}{}^a$ | 168.38 | 168.00 |
| (h) | (168.00-169.75) | (24.00-169.92) |
| $AUC_{0-4W}$ | 6800 ± 2480 | 13500 ± 5930 |
| (µg · h/mL) | (6520) [36.4] | (12300) [43.9] |
| $t_{1/2z}$ | 167 ± 62.2 | 286 ± 133 |
| (h) | (159) [37.2] | (256) [46.5] |
| $CL_{ss}/F$ | 0.0396 ± 0.00992 | 0.0450 ± 0.0219 |
| (L/h) | (0.0383) [25.0] | (0.0407) 48.7] |
| $V_{ss}/F$ | 17.9 ± 5.90 | 24.2 ± 12.2 |
| (L) | (17.3) [32.9] | (22.2) [50.3] |

$^a$Median (Min-Max)

Source = PKS Study: TDR11407; Scenario: P-X-B-EV-OD, Version 6

Date/Time = 9/13/2016 3:53:43 PM

Dose Proportionality Assessment

Figure 6:
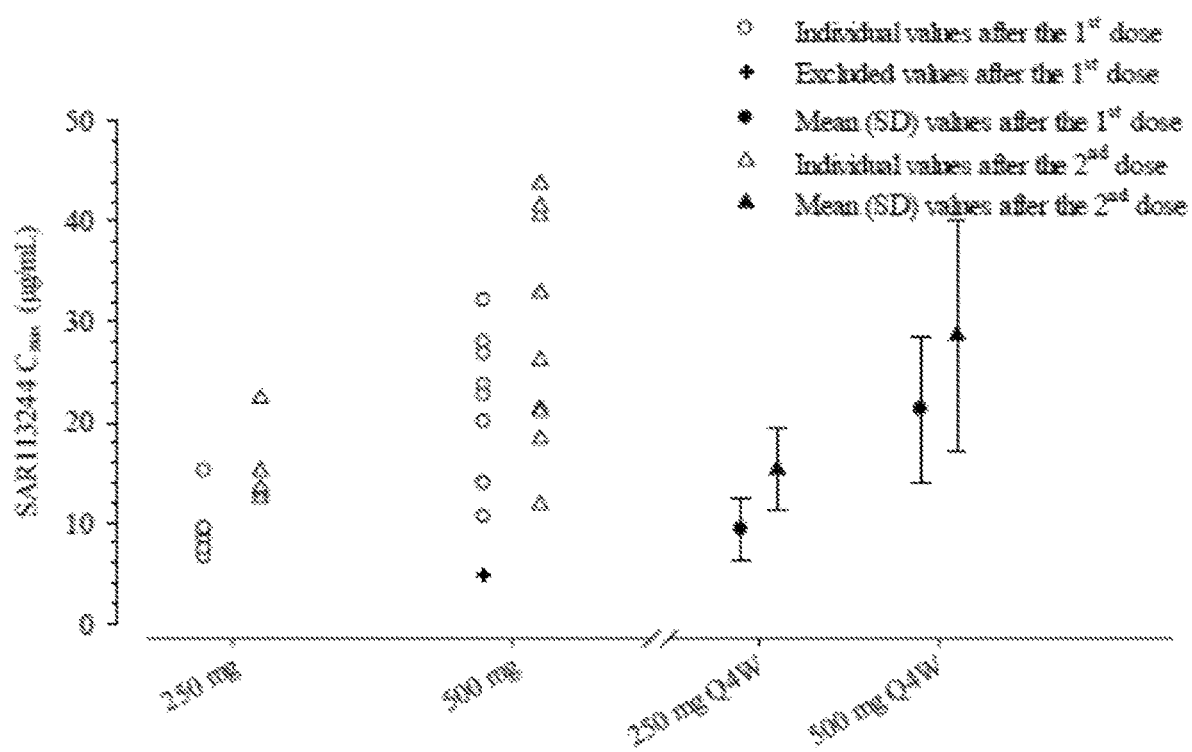
FIG. 6 is a graph showing individual and mean (SD) SAR113244 $C_{max}$ values after a 1st dose and a 2nd dose.
Figure 7:
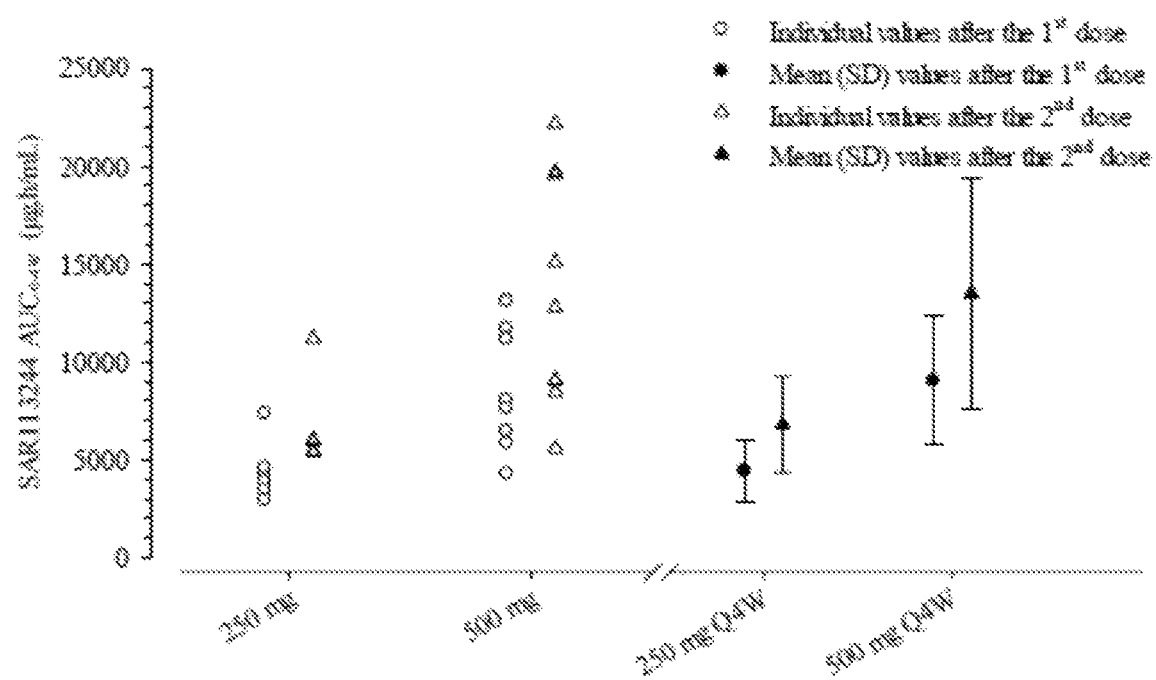
FIG. 7 is a graph showing individual and mean (SD) SAR113244 $AUC_{0-4w}$ after a 1st dose and a 2nd dose.

Individual and mean (SD) SAR113244 $C_{max}$ and $AUC_{0-4w}$ values are presented graphically for each dose group in FIG. 6 and FIG. 7. The results of the dose proportionality analysis are presented in Table 27.

TABLE 27

Estimate with 90% CI for SAR113244 exposure ratio of SAR113244, with increase in dose after the 1st dose (Day 1) and the 2nd dose (Day 29)

| Day | Parameter | Dose ratio | Estimate | 90% CI |
|---|---|---|---|---|
| Day 1 | $C_{max}$ (ug/mL) | (Ratio 500/250) = 2 | 2.23 | (1.61 to 3.08) |
|  | $AUC_{0-4w}$ (ug · h/mL) | (Ratio 500/250) = 2 | 2.01 | (1.42 to 2.82) |
| Day 29 | $C_{max}$ (ug/mL) | (Ratio 500/250) = 2 | 1.77 | (1.20 to 2.59) |
|  | $AUC_{0-4w}$ (ug · h/mL) | (Ratio 500/250) = 2 | 1.88 | (1.24 to 2.87) |

Over the 2.0-fold dose range of 250 mg to 500 mg, mean SARI 13244 $C_{max}$ and $AUC_{0-4w}$ increased by 2.23- and 2.01-fold respectively after a first dose, and by 1.77- and 1.88-fold respectively, after a second dose, indicating that exposure increased with no major deviation from dose proportionality over the range 250 mg to 500 mg.

Accumulation Ratio

Accumulation ratios for $C_{max}$ and $AUC_{0-4w}$ are presented in Table 28.

TABLE 28

Accumulation ratio (Day29/Day1) and 90% CI on SAR113244 $C_{max}$ and $AUC_{0-4w}$

| Parameter | Comparison | Estimate | 90% CI |
|---|---|---|---|
| Rac ($C_{max}$) | SAR113244 250 mg Q4W | 1.64 | (1.38 to 1.94) |
|  | SAR113244 500 mg Q4W | 1.31 | (1.16 to 1.49) |
|  | Pooled SAR113244 doses | 1.47 | (1.32 to 1.63) |
| Rac ($AUC_{0-4w}$) | SAR113244 250 mg Q4W | 1.55 | (1.34 to 1.78) |
|  | SAR113244 500 mg Q4W | 1.45 | (1.31 to 1.61) |
|  | Pooled SAR113244 doses | 1.50 | (1.37 to 1.64) |

After the administration of 2 doses of SAR113244, accumulation ratios pooled over 250 mg and 500 mg doses were of 1.47 for $C_{max}$ and of 1.50 for $AUC_{0-4w}$.

Dose Effect Assessment on $t_{1/2z}$

Figure 8:
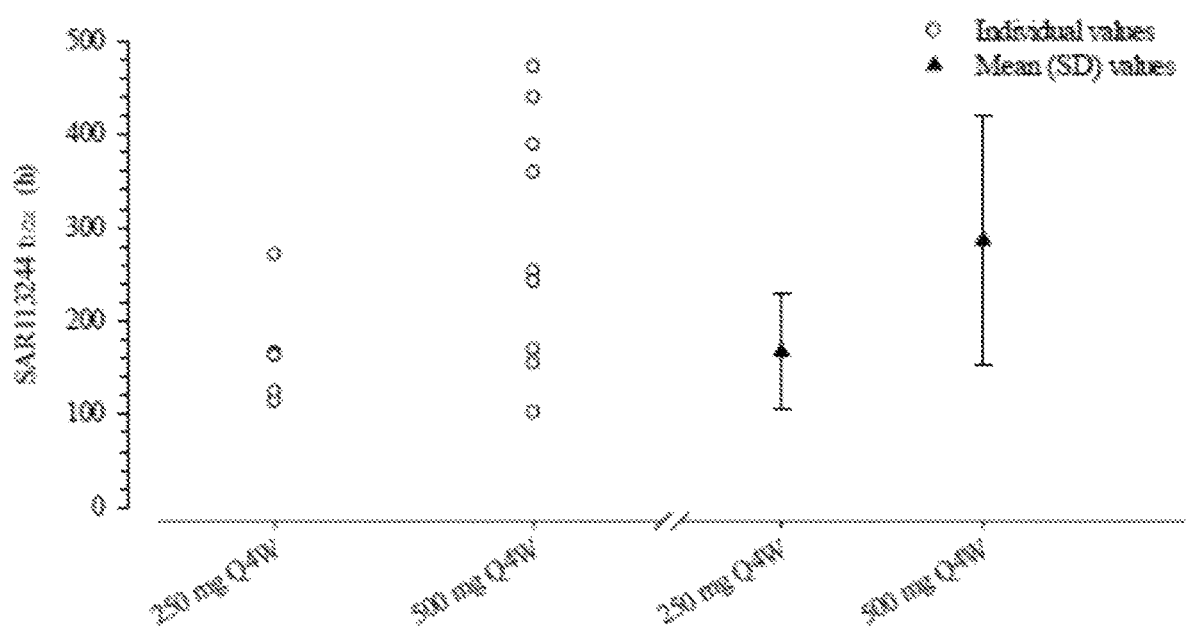
FIG. 8 is a graph showing individual and mean (SD) SAR113244 $t_{1/2z}$ values after the 2nd dose (n=5 at 250 mg; n=9 at 500 mg).

Individual and mean (SD) SARI 13244 $t_{1/2z}$ values after the second dose are presented graphically for each dose group in FIG. 8. The results of the dose effect statistical analysis are presented in Table 29 and Table 30.

TABLE 29

Dose effect on SAR113244 $t_{1/2z}$ values

| Parameter | Effect | Num DF | Den DF | F-statistic | p-value |
|---|---|---|---|---|---|
| Log ($t_{1/2z}$) | Dose | 1.0 | 12.0 | 3.22 | 0.098 |

TABLE 30

Estimates of $t_{1/2z}$ after the 2nd dose with associated 90% confidence intervals

| Parameter | Group | Estimate | 90% CI |
|---|---|---|---|
| $t_{1/2z}$ (h) | SAR113244 200 mg Q4W | 158.99 | (108.97 to 231.97) |
|  | SAR113244 500 mg Q4W | 255.57 | (192.85 to 338.68) |
|  | Pooled SAR113244 doses | 201.58 | (159.27 to 255.12) |

No significant increase in $t_{1/2z}$ with dose (p=0.098) was observed. When pooled over the 250 mg and 500 mg range, the estimate of $t_{1/2z}$ geometric mean was of 202 hours, i.e., 8.4 days.

Variance Component

Within-patient and total SDs for SAR113244 $C_{max}$ and $AUC_{0-4w}$ are presented in Table 31.

TABLE 31

Variance component for SAR113244 $C_{max}$ and $AUC_{0-4w}$

| Parameter | Within-subject SD | | Total SD | |
|---|---|---|---|---|
| | Estimate | 90% CI | Estimate | 90% CI |
| Log ($C_{max}$) | 0.150 | (0.113 to 0.227) | 0.366 | (0.287 to 0.532) |
| Log ($AUC_{0-4w}$) | 0.125 | (0.095 to 0.190) | 0.395 | (0.306 to 0.579) |

SDs estimated on the log scale, i.e. after log-transforming the parameters

The total variability expressed in CV (%) was moderate on SAR113244 $C_{max}$ and $AUC_{0-4w}$ with 36.6% and 39.5%, respectively. Within-patient variability expressed in CV (%) was low on $C_{max}$ and $AUC_{0-4w}$, with 15.0% and 12.5%, respectively.

Immunogenicity

Anti-drug antibodies were not detected in any patients receiving placebo or in any patients prior to the administration of SAR113244. The incidence of treatment-induced ADA in patients receiving 250 mg Q4W SAR113244 and patients receiving 500 mg Q4W SAR113244 was 66.7% (4/6) and 20.0% (2/10), respectively. Overall, treatment-induced ADA were detected in 37.5% of patients treated with SAR113244.

Of the 6 patients with detectable ADA, 4 patients (66.7%) had persistent treatment-induced antibodies and 2 patients (33.3%) had transient treatment-induced ADA.

There were approximately 24 weeks between the first and last positive samples and as such, the patients could not be classified as having transient or persistent treatment-induced antibodies. Overall, the median time of onset for ADA response was 73.5 days and the median ADA duration was 137.0 days (range: 23 to 170 days). The measured ADA peak titers were in the range of 60 to 600 IU/mL.

Pharmacokinetic Conclusions

After SC SAR113244 doses from 250 to 500 mg, all verum patients had quantifiable exposure to the drug, with peak concentrations of SAR113244 in plasma 7 days (median value) after the first dose and after the second dose.

SAR113244 exposure increased dose proportionally after 250 mg to 500 mg repeated doses. For a 2.0-fold increase in dose, mean $C_{max}$ and $AUC_{0-4w}$ increased by 2.23- and 2.01-fold, respectively after the first dose, and by 1.77- and 1.88-fold respectively, after the second dose. After the administration of 2 doses of SAR113244, accumulation ratios pooled over 250 mg and 500 mg doses were of 1.47 for $C_{max}$ and of 1.50 for $AUC_{0-4w}$.

Dose had no statistically significant effect on $t_{1/2z}$. The pooled geometric mean $t_{1/2z}$ estimate over the 250 mg to 500 mg range was of 202 hours, i.e., 8.4 days.

The total variability for SAR113244 $C_{max}$ and $AUC_{0-4w}$ was moderate with respectively 36.6% and 39.5%. Within-patient variability for $C_{max}$ and $AUC_{0-4w}$ was low with respectively 15.0% and 12.5%.

Overall, treatment-induced ADA were detected in 37.5% of patients treated with SAR113244. There was no dose effect on ADA. All patients (4/4) with treatment-induced ADA in the 250 mg SAR113244 treatment group had a persistent ADA response and all patients (2/2) with treatment induced ADA in the 500 mg SAR113244 treatment group had a transient ADA response.

DISCUSSION AND OVERALL CONCLUSIONS

SAR113244 was generally safe and well tolerated when administered to male and female lupus patients at doses of 250 g and 500 mg Q4W as 2 injections.

The most frequently reported TEAEs (reported in >2 patients) were nasopharyngitis and headache, reported in all treatment groups, and injection site erythema, reported only in patients receiving SAR113244. Postural dizziness, procedural dizziness, and nausea were each reported in 2 patients, and all other TEAEs were single occurrences. There did not appear to be any dose-related trends in the type or incidence of AEs reported.

There were a few PCSAs for laboratory assessments and vital signs both in patients treated with SAR113244 and the placebo group, with no dose- or treatment-related trends. Few PCSAs for heart rate and QTcF were reported only in patients receiving SAR113244.

Injection site reactions such as erythema (in 5 patients) and itch (in 1 patient) were reported in 16 patients receiving SARI 13244, with no dose relationship. All injection site erythema were of mild intensity.

SAR113244 had no relevant effect on the level of peripheral blood total B and T cells, or immunoglobulins IgA, IgD, IgE, IgG, or IgM.

Saturation of CXCR5 by SARI 13244 occurred 7 days after the first dose for all patients at 250 mg and 500 mg. The duration of saturation relative to the second dose was of 42 days as median value at 250 mg, and appeared to increase to 56 days as median value at 500 mg. For both dose groups, normalized RO % had decreased out of the saturation zone by Day 113 in 10/12 patients (in some patients to <LLOQ), although normalized RO %>80% was still observed in 2 patients on Day 113.

SAR113244 had no consistent effect on disease activity and QoL scales, serum CXCL13, auto-antibody levels, complement levels, or on B cell or T cell subsets. A transient increase in antibody-secreting cells was noted in some patients following the 250 mg dose, but a similar degree of increase was not observed after the 500 mg dose.

After SC SAR113244 doses from 250 to 500 mg, all verum patients had quantifiable exposure to the drug, with peak concentrations of SAR113244 in plasma 7 days (median value) after the first dose and after the second dose.

SAR113244 exposure increased dose proportionally after 250 mg to 500 mg repeated doses. After the administration of 2 doses of SAR113244, accumulation ratios pooled over 250 mg and 500 mg doses were of 1.47 for $C_{max}$ and of 1.50 for $AUC_{0-4w}$. Dose had no statistically significant effect on $t_{1/2z}$. The pooled geometric mean $t_{1/2z}$ estimate over the 250 mg to 500 mg range was of 202 hours, i.e., 8.4 days.

The total variability for SAR113244 $C_{max}$ and $AUC_{0-4w}$ was moderate with respectively 36.6% and 39.5%. Within-patient variability for $C_{max}$ and $AUC_{0-4w}$ was low with respectively 15.0% and 12.5%.

Anti-drug antibodies were not detected in any patients receiving placebo or in any patients prior to the administration of SAR113244. Overall, treatment-induced ADA were detected in 37.5% of patients treated with SAR113244.

TABLE 32

Individual and descriptive statistics on CXCR5 receptor occupancy versus time following a 1st and 2nd dose of 250 mg SAR113244

| Dose (mg) | Subject | RO % | | | | | | | | | | |
|---|---|---|---|---|---|---|---|---|---|---|---|---|
| | | Day 1* | Day 8 | Day 15 | Day 29** | Day 36 | Day 43 | Day 57 | Day 85 | Day 113 | Day 296 | Day 299 |
| 250 | 276001003 | <LOQ | 83.0 | 64.0 | NS | NS | NS | NS | NS | <LOQ*** | NS | NS |
| | 276001006 | <LOQ | 66.0 | 54.2 | 71.4 | 71.0 | 63.5 | 67.8 | <LOQ | <LOQ | NS | NS |
| | 276001011 | <LOQ | 83.9 | 79.6 | ND | 87.9 | 86.7 | 90.2 | 90.3 | 78.9 | NS | <LOQ |
| | 276001012 | <LOQ | 83.0 | 81.7 | 86.2 | 88.1 | 87.7 | ND | 85.9 | 53.7 | <LOQ | NS |
| | 276001013 | <LOQ | 83.5 | 85.2 | 86.2 | ND | ND | 81.6 | 42.4 | <LOQ | NS | NS |
| | 276001014 | ND | ND | 80.3 | 72.1 | 79.6 | 73.0 | 83.2 | <LOQ | <LOQ | NS | NS |
| | N | 5 | 5 | 6 | 4 | 4 | 4 | 4 | 5 | 5 | 1 | 1 |
| | Mean | <LOQ | 79.9 | 74.2 | 79.0 | 81.7 | 77.7 | 80.7 | 43.7 | 26.5 | <LOQ | <LOQ |
| | SD | NC | 7.78 | 12.2 | 8.35 | 8.14 | 11.6 | 9.36 | 44.1 | 37.4 | NC | NC |
| | Min | <LOQ | 66.0 | 54.2 | 71.4 | 71.0 | 63.5 | 67.8 | <LOQ | <LOQ | <LOQ | <LOQ |
| | Median | <LOQ | 83.0 | 80.0 | 79.2 | 83.8 | 79.8 | 82.4 | 42.4 | 0.00 | <LOQ | <LOQ |
| | Max | <LOQ | 83.9 | 85.2 | 86.2 | 87.9 | 87.7 | 90.2 | 90.3 | 78.9 | <LOQ | <LOQ |
| | CV % | NA | 10 | 16 | 11 | 10 | 15 | 12 | 101 | 141 | NA | NA |

LOQ = 20%
ND: not determined,
NS: no sample
NC: not calculated,
NA: not applicable
*sampling before the 1st dose
**sampling before the 2nd dose
***value excluded from Day113 descriptive statistics. Patient 276001003 withdrew the study, his last bood sample was collected at the End of Study Visit on Day39 instead of Day113

TABLE 33

Individual and descriptive statistics on CXCR5 receptor occupancy versus time following a 1st dose and a 2nd dose of 500 mg SAR113244

| Dose (mg) | Subject | RO % | | | | | | | | | |
|---|---|---|---|---|---|---|---|---|---|---|---|
| | | Day 1* | Day 8 | Day 15 | Day 29** | Day 36 | Day 43 | Day 57 | Day 85 | Day 113 | Day 226 |
| 500 | 276001019*** | <LOQ | 71.5 | NS | NS | NS | NS | NS | NS | 77.4 | NS |
| | 276001023 | <LOQ | 67.3 | 78.1 | 72.0 | ND | 81.2 | 79.0 | 62.7 | <LOQ | NS |
| | 276001024 | <LOQ | 69.2 | 66.2 | 73.1 | 70.7 | ND | ND | <LOQ | <LOQ | NS |
| | 276001031 | <LOQ | 75.8 | 79.3 | 77.6 | 66.3 | 77.1 | 65.8 | ND | 62.6 | <LOQ |
| | 276001036 | <LOQ | 80.8 | 69.5 | ND | 79.2 | 68.7 | 66.5 | 68.9 | 63.4 | NS |
| | 276001041 | <LOQ | 84.8 | 85.0 | 85.3 | 91.0 | 92.6 | 91.8 | 92.7 | 80.2 | NS |
| | 276001042 | <LOQ | 98.4 | ND | 98.3 | 97.8 | 98.3 | 98.4 | 96.6 | 58.6 | NS |
| | 276001043 | <LOQ | ND | ND | 70.9 | 84.4 | ND | 83.5 | 81.4 | 66.3 | NS |
| | 276001044 | <LOQ | 84.2 | 80.7 | 75.8 | 79.7 | 79.7 | 83.9 | 73.8 | 29.6 | NS |
| | 276001046 | ND | 86.6 | 86.4 | ND | 87.3 | 87.7 | 84.3 | 87.4 | 83.4 | NS |
| | N | 8 | 8 | 7 | 7 | 8 | 7 | 8 | 8 | 9 | 1 |
| | Mean | <LOQ | 80.9 | 77.9 | 79.0 | 82.1 | 83.6 | 81.6 | 70.4 | 49.3 | <LOQ |
| | SD | NC | 10.1 | 7.52 | 9.78 | 10.4 | 9.99 | 11.3 | 30.8 | 31.8 | NC |
| | Min | <LOQ | 67.3 | 66.2 | 70.9 | 66.3 | 68.7 | 65.8 | 0.00 | 0.00 | <LOQ |
| | Median | <LOQ | 82.5 | 79.3 | 75.8 | 82.0 | 81.2 | 83.7 | 77.6 | 62.6 | <LOQ |
| | Max | <LOQ | 98.4 | 86.4 | 98.3 | 97.8 | 98.3 | 98.4 | 96.6 | 83.4 | <LOQ |
| | CV % | NA | 12 | 10 | 12 | 13 | 12 | 14 | 44 | 65 | NA |

LOQ = 20%
ND: not determined,
NS: no sample
NC: not calculated,
NA: not applicable
*sampling before the 1st dose
**sampling before the 2nd dose
***Patient 276001019 withdrew the study, his whole data were excluded from RO descriptive statistics. His last blood sample was collected at the End of Study Visit on Day28 instead of Day113

TABLE 34

Individual and descriptive statistics on normalized CXCR5 receptor occupancy versus time following a 1st dose and a 2nd dose of 250 mg SAR113244

| Dose (mg) | Subject | Normalized_RO % | | | | | | | | | |
|---|---|---|---|---|---|---|---|---|---|---|---|
| | | Day 1* | Day 8 | Day 15 | Day 29** | Day 36 | Day 43 | Day 57 | Day 85 | Day 113 | Day 296 | Day 299 |
| 250 | 276001003 | <LOQ | 100.9 | 77.8 | NS | NS | NS | NS | NS | 23.1*** | NS | NS |
| | 276001006 | <LOQ | 97.2 | 79.9 | 105.2 | 104.6 | 93.6 | 99.9 | <LOQ | <LOQ | NS | NS |
| | 276001011 | <LOQ | 94.5 | 89.7 | ND | 99.1 | 97.7 | 101.6 | 101.7 | 89.0 | NS | <LOQ |
| | 276001012 | <LOQ | 94.5 | 92.9 | 98.1 | 100.2 | 99.8 | ND | 97.7 | 61.1 | <LOQ | NS |
| | 276001013 | <LOQ | 101.3 | 103.4 | 104.6 | ND | ND | 99.0 | 51.4 | <LOQ | NS | NS |
| | 276001014 | ND | ND | ND | ND | ND | ND | ND | ND | ND | NS | NS |
| | N | 5 | 5 | 5 | 3 | 3 | 3 | 3 | 4 | 4 | 1 | 1 |
| | Mean | <LOQ | 97.7 | 88.8 | 102.6 | 101.3 | 97.0 | 100.2 | 62.7 | 37.5 | <LOQ | <LOQ |
| | SD | NC | 3.3 | 10.4 | 3.9 | 2.9 | 3.1 | 1.3 | 47.6 | 44.8 | NC | NC |
| | Min | <LOQ | 94.5 | 77.8 | 98.1 | 99.1 | 93.6 | 99.0 | <LOQ | <LOQ | <LOQ | <LOQ |
| | Median | <LOQ | 97.2 | 89.7 | 104.6 | 100.2 | 97.7 | 99.9 | 74.5 | 30.6 | <LOQ | <LOQ |
| | Max | <LOQ | 101.3 | 103.4 | 105.2 | 104.6 | 99.8 | 101.6 | 101.7 | 89.0 | <LOQ | <LOQ |
| | CV % | NA | 3 | 12 | 4 | 3 | 3 | 1 | 76 | 119 | NA | NA |

LOQ = 20%

ND: not determined,

NS: no sample

NC: not calculated,

NA: not applicable

*sampling before the 1$^{st}$ dose

**sampling before the 2$^{nd}$ dose

***value excluded from Day113 descriptive statistics. Patient 276001003 withdrew the study, his last bood sample was collected at the End of Study Visit on Day39 instead of Day113

TABLE 35

Individual and descriptive statistics on normalized CXCR5 receptor occupancy versus time following a 1st dose and a 2nd dose of 500 mg SAR113244

| Dose (mg) | Subject | Normalized_RO % | | | | | | | | |
|---|---|---|---|---|---|---|---|---|---|---|
| | | Day 1* | Day 8 | Day 15 | Day 29** | Day 36 | Day 43 | Day 57 | Day 85 | Day 113 | Day 226 |
| 500 | 276001019*** | <LOQ | 97.0 | NS | NS | NS | NS | NS | NS | 105.0 | NS |
| | 276001023 | <LOQ | 82.4 | 95.6 | 88.0 | ND | 99.3 | 96.6 | 76.8 | <LOQ | NS |
| | 276001024 | <LOQ | 89.0 | 85.1 | 94.0 | 91.0 | ND | ND | <LOQ | <LOQ | NS |
| | 276001031 | <LOQ | 93.2 | 97.5 | 95.5 | 81.5 | 94.9 | 81.0 | ND | 77.1 | <LOQ |
| | 276001036 | <LOQ | 96.2 | 82.8 | ND | 94.4 | 81.8 | 79.2 | 82.0 | 75.5 | NS |
| | 276001041 | <LOQ | 90.7 | 90.9 | 91.2 | 97.3 | 99.0 | 98.1 | 99.1 | 85.8 | NS |
| | 276001042 | <LOQ | 99.3 | ND | 99.2 | 98.7 | 99.2 | 99.3 | 97.5 | 59.1 | NS |
| | 276001043 | <LOQ | ND | ND | 79.4 | 94.4 | ND | 93.4 | 91.1 | 74.1 | NS |
| | 276001044 | <LOQ | 97.0 | 92.9 | 87.3 | 91.8 | 91.8 | 96.7 | 85.0 | 34.1 | NS |
| | 276001046 | ND | ND | ND | ND | ND | ND | ND | ND | ND | NS |
| | N | 8 | 7 | 6 | 7 | 7 | 6 | 7 | 7 | 8 | 1 |
| | Mean | <LOQ | 92.5 | 90.8 | 90.7 | 92.7 | 94.3 | 92.0 | 75.9 | 50.7 | <LOQ |

TABLE 35-continued

Individual and descriptive statistics on normalized CXCR5 receptor occupancy versus time following a 1st dose and a 2nd dose of 500 mg SAR113244

| Dose (mg) | Subject | Normalized_RO % | | | | | | | | |
|---|---|---|---|---|---|---|---|---|---|---|
| | | Day 1* | Day 8 | Day 15 | Day 29** | Day 36 | Day 43 | Day 57 | Day 85 | Day 113 | Day 226 |
| | SD | NC | 5.8 | 5.8 | 6.5 | 5.7 | 6.8 | 8.4 | 34.4 | 35.0 | NC |
| | Min | <LOQ | 82.4 | 82.8 | 79.4 | 81.5 | 81.8 | 79.2 | <LOQ | <LOQ | <LOQ |
| | Median | <LOQ | 93.2 | 91.9 | 91.2 | 94.4 | 96.9 | 96.6 | 85.0 | 66.6 | <LOQ |
| | Max | <LOQ | 99.3 | 97.5 | 99.2 | 98.7 | 99.3 | 99.3 | 99.1 | 85.8 | <LOQ |
| | CV % | NA | 6 | 6 | 7 | 6 | 7 | 9 | 45 | 69 | NA |

LOQ = 20%
ND: not determined,
NS: no sample
NC: not calculated,
NA: not applicable
*sampling before the 1$^{st}$ dose
**sampling before the 2$^{nd}$ dose
***Patient 276001019 withdrew the study, his whole data were excluded from RO descriptive statistics. His last blood sample was collected at the End of Study Visit on Day28 instead of Day 113

TABLE 36

Individual values and descriptive statistics of maximal occupancy following a 1st dose and a 2nd dose of 250 mg and 500 mg SAR113244

| Dose (mg) | Subject | Saturation duration relative to the 1$^{st}$ dose (Day) | Saturation duration relative to the 2$^{nd}$ dose (Day) |
|---|---|---|---|
| 250 | 276001003 | NC | NC |
| | 276001006 | 56,00 | 28,00 |
| | 276001011 | 112,00 | 84,00 |
| | 276001012 | 84,00 | 56,00 |
| | 276001013 | 56,00 | 28,00 |
| | N | 4 | 4 |
| | Min | 56,00 | 28,00 |
| | Median | 70,00 | 42,00 |
| | Max | 112,00 | 84,00 |
| 500 | 276001019 | NC | NC |
| | 276001023 | 56,00 | 28,00 |
| | 276001024 | NC | NC |
| | 276001031 | NC | NC |
| | 276001036 | 84,00 | 56,00 |
| | 276001041 | 112,00 | 84,00 |
| | 276001042 | 84,00 | 56,00 |
| | 276001043 | 84,00 | 56,00 |
| | 276001044 | 84,00 | 56,00 |
| | N | 6 | 6 |
| | Min | 56,00 | 28,00 |
| | Median | 84,00 | 56,00 |
| | Max | 112,00 | 84,00 |

TABLE 37

Electrolytes - Number of patients with abnormalities (PCSA) during the TEAE period according to baseline status - safety population

| | Placebo (N = 5) | | 250 mg Q4W (N = 6) | | 500 mg Q4W (N = 10) | |
|---|---|---|---|---|---|---|
| Laboratory parameter PCSA criteria n/N1 | Nor. bas. | Abn. bas. | Nor. bas. | Abn. bas. | Nor. bas. | Abn. bas. |
| Sodium | | | | | | |
| ≤129 mmol/L | 0/5 | 0/0 | 0/6 | 0/0 | 0/10 | 0/0 |
| ≥160 mmol/L | 0/5 | 0/0 | 0/6 | 0/0 | 0/10 | 0/0 |
| Potassium | | | | | | |
| <3 mmol/L | 0/5 | 0/0 | 0/6 | 0/0 | 0/10 | 0/0 |
| ≥5.5 mmol/L | 0/5 | 0/0 | 0/6 | 0/0 | 0/10 | 0/0 |
| Chloride | | | | | | |
| <80 mmol/L | 0/5 | 0/0 | 0/6 | 0/0 | 0/10 | 0/0 |
| >115 mmol/L | 0/5 | 0/0 | 0/6 | 0/0 | 0/10 | 0/0 |

PCSA: Potentially Clinically Significant Abnormalities (Version of 2014 May 24)

LLN/ULN: Lower/Upper Limit of Normal range, B: Baseline, Nor. bas.: Normal baseline, Abn. bas.: Abnormal baseline (LLN/ULN or PCSA)

n/N1 = Number of patients who met the criterion at least once/number of patients within each group who had that parameter assessed Note:

A PCSA is considered to be on-treatment if it occurred from the time of the first investigational medicinal product (IMP) administration up to the end of study visit (included).

The numbers of patients with PCSAs for liver function during the TEAE period are presented in Table 38.

TABLE 38

Liver function - Number of patients with abnormalities (PCSA) during the TEAE period according to baselin status - safety population

| | | | SAR113244 | | | | |
|---|---|---|---|---|---|---|---|
| | Placebo (N = 5) | | 250 mg Q4W (N = 6) | | 500 mg Q4W (N = 10) | | |
| Laboratory parameter PCSA criteria n/N1 | Nor. bas. | Abn. bas. | Nor. bas. | Abn. bas. | Nor. bas. | Abn. bas. | Mis. bas. |
| ALT (SGPT-ALAT) | | | | | | | |
| >3 ULN | 0/5 | 0/0 | 0/6 | 0/0 | 0/10 | 0/0 | 0/0 |
| AST (SGOT-ASAT) | | | | | | | |
| >3 ULN | 0/5 | 0/0 | 0/6 | 0/0 | 0/9 | 0/0 | 0/1 |
| Alkaline phosphatase | | | | | | | |
| >1.5 ULN | 0/5 | 0/0 | 0/6 | 0/0 | 0/10 | 0/0 | 0/0 |

TABLE 38-continued

Liver function - Number of patients with abnormalities (PCSA) during the TEAE period according to baselin status - safety population

| | | | SAR113244 | | | | |
|---|---|---|---|---|---|---|---|
| | Placebo (N = 5) | | 250 mg Q4W (N = 6) | | 500 mg Q4W (N = 10) | | |
| Laboratory parameter PCSA criteria n/N1 | Nor. bas. | Abn. bas. | Nor. bas. | Abn. bas. | Nor. bas. | Abn. bas. | Mis. bas. |
| Total bilirubin | | | | | | | |
| >1.5 ULN | 0/5 | 0/0 | 0/6 | 0/0 | 0/10 | 0/0 | 0/0 |

PCSA: Potentially Clinically Significant Abnormalities (Version of 2014-05-24)
LLN/ULN: Lower/Upper Limit of Normal range,
B: Baseline,
Nor. bas.: Normal baseline,
Abn. bas.: Abnormal baseline (LLN/ULN or PCSA)
n/N1 = Number of patients who met the criterion at least once/number of patients within each group who had that parameter assessed
Note:
A PCSA is considered to be on-treatment if it occurred from the time of the first investigational medicinal product (IMP) administration up to the end of study visit (included).
For ALT, AST, ALP and Total Bilirubin, values < LLN (or LLN missing) are counted as normal.

Listing of Other Observations Related to Safety (Each Patient)

TABLE 39

Listing of patients with QTc/QTcB/QTcF >480 ms and/or delta QTc/QTcB/QTcF >60 ms - safety population

| Visit | Theor. time | | HR (bpm) | | PR (ms) | | QRS (ms) | | QT (ms) | | QTcB (ms) | | QTcF (ms) | |
|---|---|---|---|---|---|---|---|---|---|---|---|---|---|---|
| | | | Value | Delta | Value | % change | Value | % change | Value | Delta | Value | Delta | Value | Delta |
| Treatment group = SAR113244 250 mg Q4W-Subject = 276001006 (Female/42 years/177 cm/69.9 kg/22.3 kg/m2/Caucasian/White) | | | | | | | | | | | | | | |
| D1 | T0H | S | 68B | | 169B | | 93B | | 425B | | 452B+ | | 442B | |
| D1 | T3H | S | 89 | 21 | 163 | −3.6 | 96 | 3.2 | 403 | −22 | 491++ | 39+ | 460+ | 18 |

PCSA: Potentially Clinically Significant Abnormalities (Version of 2014-05-24)
B: Baseline,
Delta: Change from baseline (B),
% change: Percent change from baseline (B),
r: Rechecked value
S: Core lab semi-automatic reading of 12-lead ECG
−/−− or +/++: Abnormal value reaching the $1^{st}/2^{nd}$ or lower or the $1^{st}/2^{nd}$ or upper PCSA limit
Note:
Baseline is defined as the D1 predose assessment value.
Note:
A PCSA is considered to be on-treatment if it occurred from the time of the first investigational medicinal product (IMP) administration up to the end of study visit (included).

TABLE 40

Listing of sequences disclosed in specification

| SEQ ID NO: | SEQUENCE | Description |
|---|---|---|
| SEQ ID NO: 11 | DIVMTQAAPSVAVTPRESVSISCRSSKSLLHSSGKTYL YWFLQRPGQSPQLLIYRMSNLASGVPDRFSGSGSGTAF TLRISRVEAEDVGVYYCMQHLEYPYTFGGGTKLEIK | Light chain variable domain |
| SEQ ID NO: 12 | QVQLKESGPGLVAPSQSLSITCTVSGFSLIDYGVNWIR QPPGKGLEWLGVIWGDGTTYYNSALKSRLSIRKDNSQS QVFLKMNSLQTDDTAMYYCARIVYWGQGTLVTVSA | Heavy chain variable domain |
| SEQ ID NO: 13 | DIVMTQSALSVAVTPGESVSISCRSSKSLLHSSGKTYL YWFLQRPGQSPQLLIYRMSNLASGVPDRFSGSGSGTAF TLKISRVEAEDVGVYYCMQHLEYPYTFGGGTKLEIK | Light chain variable domain (LC4) |

TABLE 40-continued

Listing of sequences disclosed in specification

| SEQ ID NO: | SEQUENCE | Description |
|---|---|---|
| SEQ ID NO: 14 | DIVMTQSALSVAVTPGESVSISCRSSKSLLHSSGKTYL<br>YWFLQRPGQSPQLLIYRLSNLASGVPDRFSGSGSGTAF<br>TLKISRVEAEDVGVYYCMQHLEYPYTFGGGTKLEIK | Light chain<br>variable domain<br>(LC5) |
| SEQ ID NO: 15 | DIVMTQSALSVAVTPGESVSISCRSSKSLLHSSGKTYL<br>YWFLQRPGQSPQLLIYRLSSNLASGVPDRFSGSGSGTA<br>FTLKISRVEAEDVGVYYCMQHLEYPYTFGGGTKLEIK | Light chain<br>variable domain<br>(LC6) |
| SEQ ID NO: 16 | QVQLQESGPGLVAPSESLSITCTVSGFSLIDYGVNWIR<br>QPPGKGLEWLGVIWGDGTTYYNPSLKSRLSISKDNSKS<br>QVFLKMNSLTAADTAMYYCARIVYWGQGTLVTVSS | Heavy chain<br>variable domain<br>(HC3) |
| SEQ ID NO: 17 | MGWSCIILFLVATATGVHSDIVMTQSALSVAVTPGESV<br>SISCRSSKSLLHSSGKTYLYWFLQRPGQSPQLLIYRMS<br>NLASGVPDRFSGSGSGTAFTLKISRVEAEDVGVYYCMQ<br>HLEYPYTFGGGTKLEIKRTVAAPSVFIFPPSDEQLKSG<br>TASVVCLLNNFYPREAKVQWKVDNALQSGNSQESVTEQ<br>DSKDSTYSLSSTLTLSKADYEKHKVYACEVTHQGLSSP<br>VTKSFNRGEC | Light chain<br>variable domain<br>fused to IGKC<br>(LC4) |
| SEQ ID NO: 19 | MGWSCIILFLVATATGVHSDIVMTQSALSVAVTPGESV<br>SISCRSSKSLLHSSGKTYLYWFLQRPGQSPQLLIYRLS<br>NLASGVPDRFSGSGSGTAFTLKISRVEAEDVGVYYCMQ<br>HLEYPYTFGGGTKLEIKRTVAAPSVFIFPPSDEQLKSG<br>TASVVCLLNNFYPREAKVQWKVDNALQSGNSQESVTEQ<br>DSKDSTYSLSSTLTLSKADYEKHKVYACEVTHQGLSSP<br>VTKSFNRGEC | Light chain<br>variable domain<br>fused to IGKC<br>(LC5) |
| SEQ ID NO: 21 | MGWSCIILFLVATATGVHSDIVMTQSALSVAVTPGESV<br>SISCRSSKSLLHSSGKTYLYWFLQRPGQSPQLLIYRLS<br>SLASGVPDRFSGSGSGTAFTLKISRVEAEDVGVYYCM4<br>HLEYPYTFGGGTKLEIKRTVAAPSVFIFPPSDEQLKSG<br>TASVVCLLNNFYPREAKVQWKVDNALQSGNSQESVTEQ<br>DSKDSTYSLSSTLTLSKADYEKHKVYACEVTHQGLSSP<br>VTKSFNRGEC | Light chain<br>variable domain<br>fused to IGKC<br>(LC6) |
| SEQ ID NO: 23 | MGWSCIILFLVATATGVHSQVQLQESGPGLVAPSESLS<br>ITCTVSGFSLIDYGVNWIRQPPGKGLEWLGVIWGDGTT<br>YYNPSLKSRLSISKDNSKSQVFLKMNSLTAADTAMYYC<br>ARIVYWGQGTLVTVSSASTKGPSVFPLAPCSRSTSEST<br>AALGCLVKDYFPEPVTVSWNSGALTSGVHTFPAVLQSS<br>GLYSLSSVVTVPSSSLGTKTYTCNVDHKPSNTKVDKRV<br>ESKYGPPCPSCPAPEFLGGPSVFLFPPKPKDTLMISRT<br>PEVTCVVVDVSQEDPEVQFNWYVDGVEVHNAKTKPREE<br>QFNSTYRVVSVLTVLHQDWLNGKEYKCKVSNKGLPSSI<br>EKTISKAKGQPREPQVYTLPPSQEEMTKNQVSLTCLVK<br>GFYPSDIAVEWESNGQPENNYKTTPPVLDSDGSFFLYS<br>RLTVDKSRWQEGNVFSCSVMHEALHNHYTQKSLSLSLG | Heavy chain<br>variable domain<br>fused to IGHG4<br>(HC3) |
| SEQ ID NO: 30 | DIVMTQAAPSVAVTPGASVSISCRSSKSLLHSSGKTYL<br>YWFLQRPGQSPQLLIYRMSNLASGVPDRFSGSGSGTAF<br>TLRISRVEAEDVGVYYCMQHLEYPYTFGGGTKLEIK | Light chain<br>variable domain<br>(LC1) |
| SEQ ID NO: 31 | DIVMTQAAPSVAVTPGASVSISCRSSKSLLHSSGKTYL<br>YWFLQRPGQSPQLLIYRLSNLASGVPDRFSGSGSGTAF<br>TLRISRVEAEDVGVYYCMQHLEYPYTFGGGTKLEIK | Light chain<br>variable domain<br>(LC2) |
| SEQ ID NO: 32 | DIVMTQAAPSVAVTPGASVSISCRSSKSLLHSSGKTYL<br>YWFLQRPGQSPQLLIYRLSSLASGVPDRFSGSGSGTAF<br>TLRISRVEAEDVGVYYCMQHLEYPYTFGGGTKLEIK | Light chain<br>variable domain<br>(LC3) |
| SEQ ID NO: 33 | QVQLKESGPGLVAPSESLSITCTVSGFSLIDYGVNWIR<br>QPPGKGLEWLGVIWGDGTTYYNPSLKSRLSISKDNSKS<br>QVFLKVTSLTTDDTAMYYCARIVYWGQGTLVTVSA | Heavy chain<br>variable domain<br>(HC1) |
| SEQ ID NO: 34 | EVQLKESGPGLVAPGGSLSITCTVSGFSLIDYGVNWIR<br>QPPGKGLEWLGVIWGDGTTYYNAPLKGRLSISKDNSKS<br>QVFLQMNSLKTDDTAMYYCARIVYWGQGTLVTVSS | Heavy chain<br>variable domain<br>(HC2) |

TABLE 40-continued

Listing of sequences disclosed in specification

| SEQ ID NO: | SEQUENCE | Description |
| --- | --- | --- |
| SEQ ID NO: 35 | MGWSCIILFLVATATGVHSDIVMTQAAPSVAVTPRESV SISCRSSKSLLHSSGKTYLYWFLQRPGQSPQLLIYRMS NLASGVPDRFSGSGSGTAFTLRISRVEAEDVGVYYCMQ HLEYPYTFGGGTKLEIKRTVAAPSVFIFPPSDEQLKSG TASVVCLLNNFYPREAKVQWKVDNALQSGNSQESVTEQ DSKDSTYSLSSTLTLSKADYEKHKVYACEVTHQGLSSP VTKSFNRGEC | Chimeric light chain sequence |
| SEQ ID NO: 37 | MGWSCIILFLVATATGVHSQVQLKESGPGLVAPSQSLS ITCTVSGFSLIDYGVNWIRQPPGKGLEWLGVIWGDGTT YYNSALKSRLSIRKDNSQSVFLKMNSLQTDDTAMYYC ARIVYWGQGTLVTVSAASTKGPSVFPLAPCSRSTSEST AALGCLVKDYFPEPVTVSWNSGALTSGVHTFPAVLQSS GLYSLSSVVTVPSSSLGTKTYTCNVDHKPSNTKVDKRV ESKYGPPCPSCPAPEFLGGPSVFLFPPKPKDTLMISRT PEVTCVVVDVSQEDPEVQFNWYVDGVEVHNAKTKPREE QFNSTYRVVSVLTVLHQDWLNGKEYKCKVSNKGLPSSI EKTISKAKGQPREPQVYTLPPSQEEMTKNQVSLTCLVK GFYPSDIAVEWESNGQPENNYKTTPPVLDSDGSFFLYS RLTVDKSRWQEGNVFSCSVMHEALHNHYTQKSLSLSLG | Chimeric heavy chain sequence |
| SEQ ID NO: 39 | MGWSCIILFLVATATGVHSDIVMTQAAPSVAVTPGASV SISCRSSKSLLHSSGKTYLYWFLQRPGQSPQLLIYRMS NLASGVPDRFSGSGSGTAFTLRISRVEAEDVGVYYCMQ HLEYPYTFGGGTKLEIKRTVAAPSVFIFPPSDEQLKSG TASVVCLLNNFYPREAKVQWKVDNALQSGNSQESVTEQ DSKDSTYSLSSTLTLSKADYEKHKVYACEVTHQGLSSP VTKSFNRGEC | Humanized VL Sequence (LC1) |
| SEQ ID NO: 41 | MGWSCIILFLVATATGVHSDIVMTQAAPSVAVTPGASV SISCRSSKSLLHSSGKTYLYWFLQRPGQSPQLLIYRLS NLASGVPDRFSGSGSGTAFTLRISRVEAEDVGVYYCMQ HLEYPYTFGGGTKLEIKRTVAAPSVFIFPPSDEQLKSG TASVVCLLNNFYPREAKVQWKVDNALQSGNSQESVTEQ DSKDSTYSLSSTLTLSKADYEKHKVYACEVTHQGLSSP VTKSFNRGEC | Humanized VL Sequence (LC2) |
| SEQ ID NO: 43 | MGWSCIILFLVATATGVHSDIVMTQAAPSVAVTPGASV SISCRSSKSLLHSSGKTYLYWFLQRPGQSPQLLIYRLS SLASGVPDRFSGSGSGTAFTLRISRVEAEDVGVYYCMQ HLEYPYTFGGGTKLEIKRTVAAPSVFIFPPSDEQLKSG TASVVCLLNNFYPREAKVQWKVDNALQSGNSQESVTEQ DSKDSTYSLSSTLTLSKADYEKHKVYACEVTHQGLSSP VTKSFNRGEC | Humanized VL Sequence (LC3) |
| SEQ ID NO: 45 | MGWSCIILFLVATATGVHSQVQLKESGPGLVAPSESLS ITCTVSGFSLIDYGVNWIRQPPGKGLEWLGVIWGDGTT YYNPSLKSRLSISKDNSKSQVFLKVTSLTTDDTAMYYC ARIVYWGQGTLVTVSAASTKGPSVFPLAPCSRSTSEST AALGCLVKDYFPEPVTVSWNSGALTSGVHTFPAVLQSS GLYSLSSVVTVPSSSLGTKTYTCNVDHKPSNTKVDKRV ESKYGPPCPSCPAPEFLGGPSVFLFPPKPKDTLMISRT PEVTCVVVDVSQEDPEVQFNWYVDGVEVHNAKTKPREE QFNSTYRVVSVLTVLHQDWLNGKEYKCKVSNKGLPSSI EKTISKAKGQPREPQVYTLPPSQEEMTKNQVSLTCLVK GFYPSDIAVEWESNGQPENNYKTTPPVLDSDGSFFLYS RLTVDKSRWQEGNVFSCSVMHEALHNHYTQKSLSLSLG | Humanized VH Sequence (HC1) |
| SEQ ID NO: 47 | MGWSCIILFLVATATGVHSEVQLKESGPGLVAPGGSLS ITCTVSGFSLIDYGVNWIRQPPGKGLEWLGVIWGDGTT YYNAPLKGRLSISKDNSKSQVFLQMNSLKTDDTAMYYC ARIVYWGQGTLVTVSSASTKGPSVFPLAPCSRSTSEST AALGCLVKDYFPEPVTVSWNSGALTSGVHTFPAVLQSS GLYSLSSVVTVPSSSLGTKTYTCNVDHKPSNTKVDKRV ESKYGPPCPSCPAPEFLGGPSVFLFPPKPKDTLMISRT PEVTCVVVDVSQEDPEVQFNWYVDGVEVHNAKTKPREE QFNSTYRVVSVLTVLHQDWLNGKEYKCKVSNKGLPSSI EKTISKAKGQPREPQVYTLPPSQEEMTKNQVSLTCLVK GFYPSDIAVEWESNGQPENNYKTTPPVLDSDGSFFLYS RLTVDKSRWQEGNVFSCSVMHEALHNHYTQKSLSLSLG | Humanized VH Sequence (HC2) |
| SEQ ID NO: 55 | DIVMTQAAPSVAVTPGQSVSICRSSKSLLHSSGKTYL YWFLQHPGKAPQLLIYRMSNLASGVPDRFSGSGSGTAF TLTISGVQAEDVGVYYCMQHLEYPYTFGGGTKLEIK | Light chain variable domain (LC7) |

TABLE 40-continued

Listing of sequences disclosed in specification

| SEQ ID NO: | SEQUENCE | Description |
|---|---|---|
| SEQ ID NO: 56 | QVQLQESGPGLVAPSQSLSITCTVSGFSLIDYGVNWIR QPPGKGLEWLGVIWGDGTTYYNSALKSRLSISKDTSKS QVFLKMNSLITDDTAMYYCARIVYWGQGTLVTVSAAK | Heavy chain variable domain (HC4) |
| SEQ ID NO: 57 | QVQLQESGPGLVAPSQSLSITCTVSGFSLIDYGVNWIR QPPGKGLEWLGVIWGDGTTYYPSALKSRLSISKDTSKS QVFLKMNSLITDDTAMYYCARIVYWGQGTLVTVSAAK | Heavy chain variable domain (HC5) |
| SEQ ID NO: 70 | DIVMTQAAPSVAVTPGASVSISCRSSKSLLHSSGKTYL YWFLQRPGQSPQLLIYRLSSLASGVPDRFSGSGSGTAF TLRISRVEAEDVGVYYCMQHLEYPYTFGGGTKLEIKR | Light chain variable domain |
| SEQ ID NO: 71 | DIVMTQAAPSVAVTPGASVSISCRSSKSLLHSSGKTYL YWFLQRPGQSPQLLIYRLSSLASGVPDRFSGSGSGTAF TLRISRVEAEDVGVYYCMQHLEYPYTFGGGTKLEIKRT VAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | Light Chain of SAR113244 |
| SEQ ID NO: 72 | QVQLKESGPGLVAPSESLSITCTVSGFSLIDYGVNWIR QPPGKGLEWLGVIWGDGTTYYNPSLKSRLSISKDNSKS QVFLKVTSLTTDDTAMYYCARIVYWGQGTLVTVSAAST KGPSVFPLAPCSRSTSESTAALGCLVKDYFPEPVTVSW NSGALTSGVHTFPAVLQSSGLYSLSSVVTVPSSSLGTK TYTCNVDHKPSNTKVDKRVESKYGPPCPPCPAPEFEGG PSVFLFPPKPKDTLMISRTPEVTCVVVDVSQEDPEVQF NWYVDGVEVHNAKTKPREEQFNSTYRVVSVLTVLHQDW LNGKEYKCKVSNKGLPSSIEKTISKAKGQPREPQVYTL PPSQEEMTKNQVSLTCLVKGFYPSDIAVEWESNGQPEN NYKTTPPVLDSDGSFFLYSRLTVDKSRWQEGNVFSCSV MHEALHNHYTQKSLSLSLG | Heavy Chain of SAR113244 |

The CDR sequences are bolded in the sequences of Table 40. The sequences and descriptions shown in the table 40 correspond to those disclosed in U.S. Pat. No. 8,647,622 B1, which is incorporated by reference in its entirety.

The invention claimed is:

1. A method of treating lupus in a patient, comprising administering to the patient a therapeutically effective amount of an antibody or fragment thereof that specifically binds to the extracellular domain of human C—X—C Motif Chemokine Receptor 5 (CXCR5), wherein the antibody or fragment thereof comprises:
   (a) a light chain variable domain comprising the amino acid sequence of SEQ ID NO: 11, and a heavy chain variable domain comprising the amino acid sequence of SEQ ID NO: 12;
   (b) the amino acid sequences of RSSKSLLHSSGKTYLY (SEQ ID NO: 58), RMSNLAS (SEQ ID NO: 59), MQHLEYPYT (SEQ ID NO: 60), GFSLIDYGVN (SEQ ID NO: 61), VIWGDGTTY (SEQ ID NO: 62), and IVY (SEQ ID NO: 63);
   (c) a light chain variable domain comprising the amino acid sequence of SEQ ID NO: 13, SEQ ID NO: 14, or SEQ ID NO: 15, and a heavy chain variable domain comprising the amino acid sequence of SEQ ID NO: 16;
   (d) the amino acid sequences of RSSKSLLHSSGKTYLY (SEQ ID NO: 58), RLSNLAS (SEQ ID NO: 64), MQHLEYPYT (SEQ ID NO: 60), GFSLIDYGVN (SEQ ID NO: 61), VIWGDGTTY (SEQ ID NO: 62), and IVY (SEQ ID NO: 63);
   (e) the amino acid sequences of RSSKSLLHSSGKTYLY (SEQ ID NO: 58), RLSSNLAS (SEQ ID NO: 65), MQHLEYPYT (SEQ ID NO: 60), GFSLIDYGVN (SEQ ID NO: 61), VIWGDGTTY (SEQ ID NO: 62), and IVY (SEQ ID NO: 63);

(f) a variable light chain ($V_L$) comprising the amino acid sequence of SEQ ID NO: 17, SEQ ID NO: 19, or SEQ ID NO: 21, and a variable heavy chain ($V_H$) comprising the amino acid sequence of SEQ ID NO: 23;

(g) a variable light chain comprising the amino acid sequence of SEQ ID NO: 30, SEQ ID NO: 31, or SEQ ID NO: 32, and a variable heavy chain comprising the amino acid sequence of SEQ ID NO: 33 or SEQ ID NO: 34;

(h) the amino acid sequences of RSSKSLLHSSGKTYLY (SEQ ID NO: 58), RMSNLA (SEQ ID NO: 66), MQHLEYPYT (SEQ ID NO: 60), GFSLIDYGVN (SEQ ID NO: 61), VIWGDGTTY (SEQ ID N: 62), and IVY (SEQ ID NO: 63);

(i) the amino acid sequences of RSSKSLLHSSGKTYLY (SEQ ID NO: 58), RLSNLA (SEQ ID NO: 67), MQHLEYPYT (SEQ ID NO: 60), GFSLIDYGVN (SEQ ID NO: 61), VIWGDGTTY (SEQ ID NO: 62), and IVY (SEQ ID NO: 63);

(j) the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63);

(k) a variable light chain comprising the amino acid sequence of SEQ ID NO: 35, and a variable heavy chain comprising the amino acid sequence of SEQ ID NO: 37;

(l) a variable light chain comprising the amino acid sequence of SEQ ID NO: 39, SEQ ID NO: 41, or SEQ ID NO: 43, and a variable heavy chain comprising the amino acid sequence of SEQ ID NO: 45 or SEQ ID NO: 47;

(m) a variable light chain comprising the amino acid sequence of SEQ ID NO: 55, and a variable heavy chain comprising the amino acid sequence of SEQ ID NO: 56 or SEQ ID NO: 57; or (n) the amino acid sequences of RSSKSLLHSSGKTYLYW (SEQ ID NO; 69), RMSNLA (SEQ ID NO: 66), MQHLEYPYT (SEQ ID NO: 60), GFSLIDYGVN (SEQ ID NO: 61), VIWGDGTTY (SEQ ID NO: 62), and IVY (SEQ ID NO: 63); and wherein the patient has tested positive for antinuclear antibody with a titer of >1:160, wherein the antibody or fragment thereof is administered at a dose of between 200 mg to 500 mg every four weeks.

2. The method of claim 1, wherein the antibody or fragment thereof further comprises one or more constant region domains.

3. The method of claim 1, wherein the antibody or fragment thereof further comprises a $C_{H1}$, $C_{H2}$, $C_{H3}$, or combinations thereof.

4. The method of claim 2, wherein the one or more constant region domains are from an IgG antibody.

5. The method of claim 4, wherein the IgG antibody is an IgG4 antibody.

6. The method of claim 1, wherein the antibody or fragment thereof is a single chain Fv antibody.

7. The method of claim 1, wherein the antibody or fragment thereof is administered to the patient subcutaneously.

8. The method of claim 1, wherein the patient has an anti-dsDNA antibody titer of at least 11 IU/mL.

9. The method of claim 1, wherein the patient has a systematic lupus erythematosus disease activity index of at least 4.

10. A method of treating lupus in a patient, comprising administering to the patient a therapeutically effective amount of an antibody or fragment thereof that specifically binds to the extracellular domain of human CXCR5, wherein the antibody or fragment thereof comprises a variable light chain comprising the amino acid sequence of SEQ ID NO: 32, and a variable heavy chain comprising the amino acid sequence of SEQ ID NO: 33; and wherein the patient has tested positive for antinuclear antibody with a titer of ≥1:160, wherein the antibody or fragment thereof is administered at a dose of 200 mg to 500 mg every four weeks.

11. The method of claim 10, wherein the antibody or fragment thereof is administered to the patient subcutaneously.

12. The method of claim 10, wherein the patient has an anti-dsDNA antibody titer of at least 11 IU/mL.

13. The method of claim 10, wherein the patient has a systematic lupus erythematosus disease activity index of at least 4.

14. A method of treating lupus in a patient, comprising administering to the patient a therapeutically effective amount of an antibody or fragment thereof that specifically binds to the extracellular domain of human CXCR5, wherein the antibody or fragment thereof comprises the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63); and wherein the patient has tested positive for antinuclear antibody with a titer of ≥1:160, wherein the antibody or fragment thereof is administered at a dose of 200 mg to 500 mg every four weeks.

15. The method of claim 14, wherein the antibody or fragment thereof is administered to the patient subcutaneously.

16. The method of claim 14, wherein the patient has an anti-dsDNA antibody titer of at least 11 IU/mL.

17. The method of claim 14, wherein the patient has a systematic lupus erythematosus disease activity index of at least 4.

* * * * *

```
                        SEQUENCE LISTING

<160> NUMBER OF SEQ ID NOS: 72

<210> SEQ ID NO 1
<211> LENGTH: 36
<212> TYPE: PRT
<213> ORGANISM: Homo sapiens

<400> SEQUENCE: 1

Met Asn Tyr Pro Thr Leu Glu Met Asp Leu Glu Asn Leu Glu Asp Leu
1               5                   10                  15

Phe Trp Glu Leu Asp Arg Leu Asp Asn Tyr Asn Thr Ser Leu Val Glu
            20                  25                  30

Asn His Leu Cys
        35

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: a, c, g or t
<220> FEATURE:
<221> NAME/KEY: misc_feature
<222> LOCATION: (18)..(18)
<223> OTHER INFORMATION: n is a, c, g, or t
```

<400> SEQUENCE: 2
cttccggaat tcsargtnma gctgsagsag tc                                    32

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: a, c, g or t
<220> FEATURE:
<221> NAME/KEY: misc_feature
<222> LOCATION: (18)..(18)
<223> OTHER INFORMATION: n is a, c, g, or t

<400> SEQUENCE: 3
cttccggaat tcsargtnma gctgsagsag tcwgg                                 35

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggaggatcca tagacagatg ggggtgtcgt tttggc                                36

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggagctcgay attgtgmtsa cmcarwctmc a                                     31

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tatagagctc aagcttggat ggtgggaaga tggatacagt tggtgc                     46

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccaagctgtg tcctrtcc                                                    18

```
<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgacaagtcg actagcccrr gaccaggcat cc                                      32

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
wtctctrgag tcagtggg                                                      18

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgactagtcg actggtggga agatggatac ag                                      32

<210> SEQ ID NO 11
<211> LENGTH: 112
<212> TYPE: PRT
<213> ORGANISM: Mus sp.

<400> SEQUENCE: 11

Asp Ile Val Met Thr Gln Ala Ala Pro Ser Val Ala Val Thr Pro Arg
1               5                   10                  15

Glu Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 12
<211> LENGTH: 111
<212> TYPE: PRT
<213> ORGANISM: Mus sp.

<400> SEQUENCE: 12

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
```

```
                20                  25                  30

Gly Val Asn Trp Ile Arg Gln Pro Pro Gly Lys Gly Leu Glu Trp Leu
                35                  40                  45

Gly Val Ile Trp Gly Asp Gly Thr Thr Tyr Tyr Asn Ser Ala Leu Lys
            50                  55                  60

Ser Arg Leu Ser Ile Arg Lys Asp Asn Ser Gln Ser Gln Val Phe Leu
 65                  70                  75                  80

Lys Met Asn Ser Leu Gln Thr Asp Asp Thr Ala Met Tyr Tyr Cys Ala
                85                  90                  95

Arg Ile Val Tyr Trp Gly Gln Gly Thr Leu Val Thr Val Ser Ala
                100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Met Thr Gln Ser Ala Leu Ser Val Ala Val Thr Pro Gly
1               5                   10                  15

Glu Ser Val Ser Ile Ser Cys Arg Ser Ser Lys Ser Leu Leu His Ser
                20                  25                  30

Ser Gly Lys Thr Tyr Leu Tyr Trp Phe Leu Gln Arg Pro Gly Gln Ser
                35                  40                  45

Pro Gln Leu Leu Ile Tyr Arg Met Ser Asn Leu Ala Ser Gly Val Pro
            50                  55                  60

Asp Arg Phe Ser Gly Ser Gly Ser Gly Thr Ala Phe Thr Leu Lys Ile
 65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
                100                 105                 110

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Ser Ala Leu Ser Val Ala Val Thr Pro Gly
1               5                   10                  15

Glu Ser Val Ser Ile Ser Cys Arg Ser Ser Lys Ser Leu Leu His Ser
                20                  25                  30

Ser Gly Lys Thr Tyr Leu Tyr Trp Phe Leu Gln Arg Pro Gly Gln Ser
                35                  40                  45

Pro Gln Leu Leu Ile Tyr Arg Leu Ser Asn Leu Ala Ser Gly Val Pro
            50                  55                  60

Asp Arg Phe Ser Gly Ser Gly Ser Gly Thr Ala Phe Thr Leu Lys Ile
 65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
```

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Ala Leu Ser Val Ala Val Thr Pro Gly
1               5                   10                  15

Glu Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Ser Asn Leu Ala Ser Gly Val
    50                  55                  60

Pro Asp Arg Phe Ser Gly Ser Gly Ser Gly Thr Ala Phe Thr Leu Lys
65                  70                  75                  80

Ile Ser Arg Val Glu Ala Glu Asp Val Gly Val Tyr Tyr Cys Met Gln
                85                  90                  95

His Leu Glu Tyr Pro Tyr Thr Phe Gly Gly Gly Thr Lys Leu Glu Ile
            100                 105                 110

Lys

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Pro Ser Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Thr Ala Ala Asp Thr Ala Met Tyr Tyr Cys Ala
                85                  90                  95

Arg Ile Val Tyr Trp Gly Gln Gly Thr Leu Val Thr Val Ser Ser
            100                 105                 110

<210> SEQ ID NO 17
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Gly Trp Ser Cys Ile Ile Leu Phe Leu Val Ala Thr Ala Thr Gly
1               5                   10                  15

Val His Ser Asp Ile Val Met Thr Gln Ser Ala Leu Ser Val Ala Val
                20                  25                  30

Thr Pro Gly Glu Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
50                      55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Lys Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 18
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gctagcacca tgggctggag ctgcatcatc ctgttcctgg tggccaccgc caccggcgtg     60
cacagcgaca tcgtgatgac ccagagcgcc ctcagcgtgg ccgtgacccc cggcgagagc    120
gtgagcatca gctgccgcag cagcaagagc ctgctgcaca gcagcggcaa gacctacctg    180
tactggttcc tgcagcgccc cggccagagc ccccagctgc tgatctaccg catgagcaac    240
ctggccagcg gcgtgcccga ccgcttcagc ggcagcggca gcggcaccgc cttcaccctg    300
aagatcagcc gcgtggaggc cgaggacgtg ggcgtgtact actgcatgca gcacctggag    360
taccccctaca ccttcggcgg cggcaccaag ctggagatca gcgtacggt ggccgctcct    420
tccgtgttca tcttccctcc ctccgacgag cagctgaagt ccggcaccgc ctccgtggtg    480
tgtctgctga caacttcta ccctcgggag gccaaggtgc agtggaaggt ggacaacgcc    540
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca agtccttcaa ccggggcgag    720
```
tgctgaagct t                                                            731

```
<210> SEQ ID NO 19
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19
```

Met Gly Trp Ser Cys Ile Ile Leu Phe Leu Val Ala Thr Ala Thr Gly
1               5                   10                  15

Val His Ser Asp Ile Val Met Thr Gln Ser Ala Leu Ser Val Ala Val
                20                  25                  30

Thr Pro Gly Glu Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
        50                  55                  60

Gly Gln Ser Pro Gln Leu Leu Ile Tyr Arg Leu Ser Asn Leu Ala Ser
65                  70                  75                  80

Gly Val Pro Asp Arg Phe Ser Gly Ser Gly Ser Gly Thr Ala Phe Thr
                85                  90                  95

Leu Lys Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

```
<210> SEQ ID NO 20
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
```
gctagcacca tgggctggag ctgcatcatc ctgttcctgg tggccaccgc caccggcgtg      60
cacagcgaca tcgtgatgac ccagagcgcc ctcagcgtgg ccgtgacccc cggcgagagc     120
gtgagcatca gctgccgcag cagcaagagc ctgctgcaca gcagcggcaa gacctacctg     180
tactggttcc tgcagcgccc cggccagagc ccccagctgc tgatctaccg cctgagcaac     240
ctggccagcg gcgtgcccga ccgcttcagc ggcagcggca gcggcaccgc cttcaccctg     300

-continued

```
aagatcagcc gcgtggaggc cgaggacgtg ggcgtgtact actgcatgca gcacctggag    360 taccccctaca ccttcggcgg cggcaccaag ctggagatca gcgtacggt ggccgctcct    420 tccgtgttca tcttccctcc ctccgacgag cagctgaagt ccggcaccgc ctccgtggtg    480
tgtctgctga caacttcta ccctcgggag gccaaggtgc agtggaaggt ggacaacgcc    540
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca agtccttcaa ccggggcgag    720
tgctgaagct t                                                         731
```

<210> SEQ ID NO 21
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Trp Ser Cys Ile Ile Leu Phe Leu Val Ala Thr Ala Thr Gly
1               5                   10                  15

Val His Ser Asp Ile Val Met Thr Gln Ser Ala Leu Ser Val Ala Val
                20                  25                  30

Thr Pro Gly Glu Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
        50                  55                  60

Gly Gln Ser Pro Gln Leu Leu Ile Tyr Arg Leu Ser Ser Leu Ala Ser
65                  70                  75                  80

Gly Val Pro Asp Arg Phe Ser Gly Ser Gly Ser Gly Thr Ala Phe Thr
                85                  90                  95

Leu Lys Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 22
<211> LENGTH: 731
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 22

```
gctagcacca tgggctggag ctgcatcatc ctgttcctgg tggccaccgc caccggcgtg    60
cacagcgaca tcgtgatgac ccagagcgcc ctcagcgtgg ccgtgacccc cggcgagagc   120
gtgagcatca gctgccgcag cagcaagagc ctgctgcaca gcagcggcaa gacctacctg   180
tactggttcc tgcagcgccc cggccagagc ccccagctgc tgatctaccg cctgagcagc   240
ctggccagcg gcgtgcccga ccgcttcagc ggcagcggca gcggcaccgc cttcaccctg   300
aagatcagcc gcgtggaggc cgaggacgtg ggcgtgtact actgcatgca gcacctggag   360
taccccctaca ccttcggcgg cggcaccaag ctggagatca gcgtacggt ggccgctcct   420
tccgtgttca tcttccctcc ctccgacgag cagctgaagt ccggcaccgc ctccgtggtg   480
tgtctgctga acaacttcta ccctcgggag gccaaggtgc agtggaaggt ggacaacgcc   540
ctgcagtccg gcaactccca ggagtccgtc accgagcagg actccaagga cagcacctac   600
tccctgtcct ccaccctgac cctgtccaag gccgactacg agaagcacaa ggtgtacgcc   660
tgtgaggtga cccaccaggg cctgtccagc cctgtgacca gtccttcaa ccggggcgag   720
tgctgaagct t                                                        731
```

<210> SEQ ID NO 23
<211> LENGTH: 456
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 23

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Ala
            20                  25                  30

Pro Ser Glu Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Pro
65                  70                  75                  80

Ser Leu Lys Ser Arg Leu Ser Ile Ser Lys Asp Asn Ser Lys Ser Gln
                85                  90                  95

Val Phe Leu Lys Met Asn Ser Leu Thr Ala Ala Asp Thr Ala Met Tyr
            100                 105                 110

Tyr Cys Ala Arg Ile Val Tyr Trp Gly Gln Gly Thr Leu Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr

```
                195              200              205
Lys Thr Tyr Thr Cys Asn Val Asp His Lys Pro Ser Asn Thr Lys Val
    210              215              220

Asp Lys Arg Val Glu Ser Lys Tyr Gly Pro Cys Pro Ser Cys Pro
225             230              235              240

Ala Pro Glu Phe Leu Gly Gly Pro Ser Val Phe Leu Phe Pro Pro Lys
                245              250              255

Pro Lys Asp Thr Leu Met Ile Ser Arg Thr Pro Glu Val Thr Cys Val
            260              265              270

Val Val Asp Val Ser Gln Glu Asp Pro Glu Val Gln Phe Asn Trp Tyr
        275              280              285

Val Asp Gly Val Glu Val His Asn Ala Lys Thr Lys Pro Arg Glu Glu
    290              295              300

Gln Phe Asn Ser Thr Tyr Arg Val Val Ser Val Leu Thr Val Leu His
305             310              315              320

Gln Asp Trp Leu Asn Gly Lys Glu Tyr Lys Cys Lys Val Ser Asn Lys
                325              330              335

Gly Leu Pro Ser Ser Ile Glu Lys Thr Ile Ser Lys Ala Lys Gly Gln
            340              345              350

Pro Arg Glu Pro Gln Val Tyr Thr Leu Pro Pro Ser Gln Glu Glu Met
        355              360              365

Thr Lys Asn Gln Val Ser Leu Thr Cys Leu Val Lys Gly Phe Tyr Pro
    370              375              380

Ser Asp Ile Ala Val Glu Trp Glu Ser Asn Gly Gln Pro Glu Asn Asn
385             390              395              400

Tyr Lys Thr Thr Pro Pro Val Leu Asp Ser Asp Gly Ser Phe Phe Leu
                405              410              415

Tyr Ser Arg Leu Thr Val Asp Lys Ser Arg Trp Gln Glu Gly Asn Val
            420              425              430

Phe Ser Cys Ser Val Met His Glu Ala Leu His Asn His Tyr Thr Gln
        435              440              445

Lys Ser Leu Ser Leu Ser Leu Gly
    450              455

<210> SEQ ID NO 24
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gctagcacca tgggctggag ctgcatcatc ctgttcctgg tggccaccgc caccggcgtg      60
cacagccagg tgcagctgca ggagagcggc cccggcctgg tggcccccag cgagagcctg     120
agcatcacct gcaccgtgag cggcttcagc ctgatcgact acggcgtgaa ctggatccgc     180 cagcccccg gcaagggcct ggagtggctg ggcgtgatct ggggcgacgg caccacctac     240
tacaacccca gcctgaagag ccgcctgagc atctccaagg acaacagcaa gagccaggtg     300
ttcctgaaga tgaacagcct gaccgccgcc gacaccgcca tgtactactg cgcccgcatc     360
gtgtactggg gccagggcac cctggtgacc gtgagcagcg ccagcaccaa gggcccttcc     420
gtgttccctc tggccccttg ctcccggtcc acctccgagt ccaccgccgc tctgggctgc     480
ctggtgaagg actacttccc tgagcctgtg accgtgtcct ggaactctgg cgccctgacc     540
```

```
tccggcgtgc acaccttccc tgccgtgctg cagtcctccg gcctgtactc cctgtcctcc    600
gtggtgaccg tgccttcctc ctccctgggc accaagacct acacctgtaa cgtggaccac    660
aagccttcca acaccaaggt ggacaagcgg gtggagtcca agtacggccc tccttgccct    720
tcctgccctg cccctgagtt cctgggcgga cctagcgtgt tcctgttccc tcctaagcct    780
aaggacaccc tgatgatctc ccggacccct gaggtgacct gtgtggtggt ggacgtgtcc    840
caggaggacc ctgaggtcca gttcaactgg tacgtggacg gcgtggaggt gcacaacgcc    900
aagaccaagc ctcgggagga gcagttcaat tccacctacc gggtggtgtc tgtgctgacc    960
gtgctgcacc aggactggct gaacggcaaa gaatacaagt gtaaggtctc caacaagggc   1020 ctgcccctcct ccatcgagaa aaccatctcc aaggccaagg ccagcctag ggagcctcag   1080 gtgtacaccc tgcctcctag ccaggaagag atgaccaaga accaggtgtc cctgacctgt   1140
ctggtgaagg gcttctaccc ttccgacatc gccgtggagt gggagtccaa cggccagcct   1200
gagaacaact acaagaccac ccctcctgtg ctggactccg acggctcctt cttcctgtac   1260
tccaggctga ccgtggacaa gtcccggtgg caggagggca acgtcttttc ctgctccgtg   1320
atgcacgagg ccctgcacaa ccactacacc cagaagtccc tgtccctgtc tctgggctga   1380
agctt                                                               1385
```

<210> SEQ ID NO 25
<211> LENGTH: 22
<212> TYPE: PRT
<213> ORGANISM: Homo sapiens

<400> SEQUENCE: 25

Lys Pro Gly Gln Pro Pro Arg Leu Leu Ile Tyr Asp Ala Ser Asn Arg
1               5                   10                  15

Ala Thr Gly Ile Pro Ala
            20

<210> SEQ ID NO 26
<211> LENGTH: 12
<212> TYPE: PRT
<213> ORGANISM: Mus musculus

<400> SEQUENCE: 26

Thr Asp Asp Thr Ala Met Tyr Tyr Cys Ala Arg Ile
1               5                   10

<210> SEQ ID NO 27
<211> LENGTH: 12
<212> TYPE: PRT
<213> ORGANISM: Homo sapiens

<400> SEQUENCE: 27

Ser Glu Asp Ser Ala Leu Tyr Tyr Cys Ala Arg Asp
1               5                   10

<210> SEQ ID NO 28
<211> LENGTH: 112
<212> TYPE: PRT
<213> ORGANISM: Mus musculus

<400> SEQUENCE: 28

Asp Ile Val Met Thr Gln Ala Ala Pro Ser Val Ala Val Thr Pro Arg
1               5                   10                  15

Glu Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 29
<211> LENGTH: 111
<212> TYPE: PRT
<213> ORGANISM: Mus musculus

<400> SEQUENCE: 29

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Ser Ala Leu Lys
    50                  55                  60

Ser Arg Leu Ser Ile Arg Lys Asp Asn Ser Gln Ser Gln Val Phe Leu
65                  70                  75                  80

Lys Met Asn Ser Leu Gln Thr Asp Asp Thr Ala Met Tyr Tyr Cys Ala
                85                  90                  95

Arg Ile Val Tyr Trp Gly Gln Gly Thr Leu Val Thr Val Ser Ala
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 31

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Ser Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Lys Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
            20                  25                  30
```

```
Gly Val Asn Trp Ile Arg Gln Pro Pro Gly Lys Gly Leu Glu Trp Leu
            35                  40                  45

Gly Val Ile Trp Gly Asp Gly Thr Thr Tyr Tyr Asn Pro Ser Leu Lys
50                  55                  60

Ser Arg Leu Ser Ile Ser Lys Asp Asn Ser Lys Ser Gln Val Phe Leu
65                  70                  75                  80

Lys Val Thr Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala
            100                 105                 110
```

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Ile Asp Tyr
                20                  25                  30

Gly Val Asn Trp Ile Arg Gln Pro Pro Gly Lys Gly Leu Glu Trp Leu
            35                  40                  45

Gly Val Ile Trp Gly Asp Gly Thr Thr Tyr Tyr Asn Ala Pro Leu Lys
50                  55                  60

Gly Arg Leu Ser Ile Ser Lys Asp Asn Ser Lys Ser Gln Val Phe Leu
65                  70                  75                  80

Gln Met Asn Ser Leu Lys Thr Asp Asp Thr Ala Met Tyr Tyr Cys Ala
                85                  90                  95

Arg Ile Val Tyr Trp Gly Gln Gly Thr Leu Val Thr Val Ser Ser
            100                 105                 110
```

<210> SEQ ID NO 35
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
                20                  25                  30

Thr Pro Arg Glu Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110
```

```
Met Gln His Leu Glu Tyr Pro Tyr Thr Phe Gly Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235
```

<210> SEQ ID NO 36
<211> LENGTH: 731
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gctagcacca tgggctggag ctgcatcatc ctgttcctgg tggccaccgc caccggcgtg    60
cacagcgaca tcgtgatgac ccaggccgcc cccagcgtgg ccgtgacccc ccgcgagagc   120
gtgagcatca gctgccgcag cagcaagagc ctgctgcaca gcagcggcaa gacctacctg   180
tactggttcc tgcagcgccc cggccagagc ccccagctgc tgatctaccg catgagcaac   240
ctggccagcg gcgtgcccga ccgcttcagc ggcagcggca gcggcaccgc cttcaccctg   300
cgcatcagcc gcgtggaggc cgaggacgtg ggcgtgtact actgcatgca gcacctggag   360
taccccctaca ccttcggcgg cggcaccaag ctggagatca gcgtacggt ggccgctcct   420
tccgtgttca tcttccctcc ctccgacgag cagctgaagt ccggcaccgc ctccgtggtg   480
tgtctgctga caacttcta ccctcgggag gccaaggtgc agtggaaggt ggacaacgcc   540
ctgcagtccg gcaactccca ggagtccgtc accgagcagg actccaagga cagcacctac   600
tccctgtcct ccaccctgac cctgtccaag gccgactacg agaagcacaa ggtgtacgcc   660
tgtgaggtga cccaccaggg cctgtccagc cctgtgacca gtccttcaa ccggggcgag   720
tgctgaagct t                                                        731
```

<210> SEQ ID NO 37
<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Met Gly Trp Ser Cys Ile Ile Leu Phe Leu Val Ala Thr Ala Thr Gly
1               5                   10                  15

Val His Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
```

```
            35                  40                  45
Ile Asp Tyr Gly Val Asn Trp Ile Arg Gln Pro Pro Gly Lys Gly Leu
 50                  55                  60
Glu Trp Leu Gly Val Ile Trp Gly Asp Gly Thr Thr Tyr Tyr Asn Ser
 65                  70                  75                  80
Ala Leu Lys Ser Arg Leu Ser Ile Arg Lys Asp Asn Ser Gln Ser Gln
                 85                  90                  95
Val Phe Leu Lys Met Asn Ser Leu Gln Thr Asp Asp Thr Ala Met Tyr
            100                 105                 110
Tyr Cys Ala Arg Ile Val Tyr Trp Gly Gln Gly Thr Leu Val Thr Val
            115                 120                 125
Ser Ala Ala Ser Thr Lys Gly Pro Ser Val Phe Pro Leu Ala Pro Cys
            130                 135                 140
Ser Arg Ser Thr Ser Glu Ser Thr Ala Ala Leu Gly Cys Leu Val Lys
145                 150                 155                 160
Asp Tyr Phe Pro Glu Pro Val Thr Val Ser Trp Asn Ser Gly Ala Leu
                165                 170                 175
Thr Ser Gly Val His Thr Phe Pro Ala Val Leu Gln Ser Ser Gly Leu
            180                 185                 190
Tyr Ser Leu Ser Ser Val Val Thr Val Pro Ser Ser Ser Leu Gly Thr
            195                 200                 205
Lys Thr Tyr Thr Cys Asn Val Asp His Lys Pro Ser Asn Thr Lys Val
            210                 215                 220
Asp Lys Arg Val Glu Ser Lys Tyr Gly Pro Pro Cys Pro Ser Cys Pro
225                 230                 235                 240
Ala Pro Glu Phe Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
            260                 265                 270
Val Val Asp Val Ser Gln Glu Asp Pro Glu Val Gln Phe Asn Trp Tyr
            275                 280                 285
Val Asp Gly Val Glu Val His Asn Ala Lys Thr Lys Pro Arg Glu Glu
            290                 295                 300
Gln Phe Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Gly Leu Pro Ser Ser Ile Glu Lys Thr Ile Ser Lys Ala Lys Gly Gln
            340                 345                 350
Pro Arg Glu Pro Gln Val Tyr Thr Leu Pro Pro Ser Gln Glu Glu Met
            355                 360                 365
Thr Lys Asn Gln Val Ser Leu Thr Cys Leu Val Lys Gly Phe Tyr Pro
            370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Arg Leu Thr Val Asp Lys Ser Arg Trp Gln Glu Gly Asn Val
            420                 425                 430
Phe Ser Cys Ser Val Met His Glu Ala Leu His Asn His Tyr Thr Gln
            435                 440                 445
Lys Ser Leu Ser Leu Ser Leu Gly
            450                 455
```

<210> SEQ ID NO 38
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
gctagcacca tgggctggag ctgcatcatc ctgttcctgg tggccaccgc caccggcgtg      60
cacagccagg tgcagctgaa ggagagcggc cccggcctgg tggcccccag ccagagcctg     120
agcatcacct gcaccgtgag cggcttcagc ctgatcgact acgcgtgaa ctggatccgc      180
cagcccccg gcaagggcct ggagtggctg gcgtgatct ggggcgacgg caccacctac      240
tacaacagcg ccctgaagag ccgcctgagc atccgcaagg acaacagcca gagccaggtg      300
ttcctgaaga tgaacagcct gcagaccgac gacaccgcca tgtactactg cgcccgcatc      360
gtgtactggg gccagggcac cctggtgacc gtgagcgccg ccagcaccaa gggcccttcc      420
gtgttccctc tggcccccttg ctcccggtcc acctccgagt ccaccgccgc tctgggctgc      480
ctggtgaagg actacttccc tgagcctgtg accgtgtcct ggaactctgg cgccctgacc      540
tccggcgtgc acaccttccc tgccgtgctg cagtcctccg gcctgtactc cctgtcctcc      600
gtggtgaccg tgccttcctc ctccctgggc accaagacct acacctgtaa cgtggaccac      660
aagccttcca acaccaaggt ggacaagcgg gtggagtcca agtacggccc tccttgccct      720
tcctgccctg cccctgagtt cctgggcgga cctagcgtgt tcctgttccc tcctaagcct      780
aaggacaccc tgatgatctc ccggaccct gaggtgacct gtgtggtggt ggacgtgtcc      840
caggaggacc ctgaggtcca gttcaactgg tacgtgacg gcgtggaggt gcacaacgcc      900
aagaccaagc ctcgggagga gcagttcaat tccacctacc gggtggtgtc tgtgctgacc      960
gtgctgcacc aggactggct gaacggcaaa gaatacaagt gtaaggtctc caacaagggc     1020
ctgccctcct ccatcgagaa aaccatctcc aaggccaagg ccagcctag ggagcctcag     1080
gtgtacaccc tgcctcctag ccaggaagag atgaccaaga accaggtgtc cctgacctgt     1140
ctggtgaagg gcttctaccc ttccgacatc gccgtggagt gggagtccaa cggccagcct     1200
gagaacaact acaagaccac ccctcctgtg ctggactccg acggctcctt cttcctgtac     1260
tccaggctga ccgtggacaa gtcccggtgg caggagggca acgtcttttc ctgctccgtg     1320
atgcacgagg ccctgcacaa ccactacacc cagaagtccc tgtccctgtc tctgggctga     1380
agctt                                                                 1385
```

<210> SEQ ID NO 39
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
            20                  25                  30

Thr Pro Gly Ala Ser Val Ser Ile Ser Cys Arg Ser Ser Lys Ser Leu
        35                  40                  45
```

Leu His Ser Ser Gly Lys Thr Tyr Leu Tyr Trp Phe Leu Gln Arg Pro
50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

```
<210> SEQ ID NO 40
<211> LENGTH: 731
<212> TYPE: DNA
<213> ORGANISM: Artificial Sequence
<220> FEATURE:
<223> OTHER INFORMATION: Description of Artificial Sequence: Synthetic
      polypeptide

<400> SEQUENCE: 40
gctagcacca tgggctggag ctgcatcatc ctgttcctgg tggccaccgc caccggcgtg     60
cacagcgaca tcgtgatgac ccaggccgcc cccagcgtgg ccgtgacccc cggcgccagc    120
gtgagcatca gctgccgcag cagcaagagc ctgctgcaca gcagcggcaa gacctacctg    180
tactggttcc tgcagcgccc cggccagagc ccccagctgc tgatctaccg catgagcaac    240
ctggccagcg gcgtgcccga ccgcttcagc ggcagcggca gcggcaccgc cttcaccctg    300
cgcatcagcc gcgtggaggc cgaggacgtg ggcgtgtact actgcatgca gcacctggag    360 taccccltaca ccttcggcgg cggcaccaag ctggagatca gcgtacggt ggccgctcct    420 tccgtgttca tcttccctcc ctccgacgag cagctgaagt ccggcaccgc ctccgtggtg    480
tgtctgctga caacttctA ccctcgggag gccaaggtgc agtggaaggt ggacaacgcc    540
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca gtccttcaa ccggggcgag    720 tgctgaagct t                                                         731

<210> SEQ ID NO 41
<211> LENGTH: 238
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 41

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
                20                  25                  30

Thr Pro Gly Ala Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
50                  55                  60

Gly Gln Ser Pro Gln Leu Leu Ile Tyr Arg Leu Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 42
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gctagcacca tgggctggag ctgcatcatc ctgttcctgg tggccaccgc caccggcgtg     60
cacagcgaca tcgtgatgac ccaggccgcc cccagcgtgg ccgtgacccc cggcgccagc    120
gtgagcatca gctgccgcag cagcaagagc ctgctgcaca gcagcggcaa gacctacctg    180
tactggttcc tgcagcgccc cggccagagc ccccagctgc tgatctaccg cctgagcaac    240
ctggccagcg gcgtgcccga ccgcttcagc ggcagcggca gcggcaccgc cttcaccctg    300
cgcatcagcc gcgtggaggc cgaggacgtg ggcgtgtact actgcatgca gcacctggag    360
tacccctaca ccttcggcgg cggcaccaag ctggagatca agcgtacggt ggccgctcct    420
tccgtgttca tcttccctcc ctccgacgag cagctgaagt ccggcaccgc ctccgtggtg    480
tgtctgctga acaacttcta ccctcgggag gccaaggtgc agtggaaggt ggacaacgcc    540
```

```
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca agtccttcaa ccggggcgag    720
tgctgaagct t                                                         731
```

<210> SEQ ID NO 43
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
            20                  25                  30

Thr Pro Gly Ala Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Leu Ser Ser Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 44
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
gctagcacca tgggctggag ctgcatcatc ctgttcctgg tggccaccgc caccggcgtg    60
cacagcgaca tcgtgatgac ccaggccgcc cccagcgtgg ccgtgacccc cggcgccagc   120
```

```
gtgagcatca gctgccgcag cagcaagagc ctgctgcaca gcagcggcaa gacctacctg    180
tactggttcc tgcagcgccc cggccagagc ccccagctgc tgatctaccg cctgagcagc    240
ctggccagcg gcgtgcccga ccgcttcagc ggcagcggca gcggcaccgc cttcaccctg    300
cgcatcagcc gcgtggaggc cgaggacgtg ggcgtgtact actgcatgca gcacctggag    360 taccccctaca ccttcggcgg cggcaccaag ctggagatca gcgtacggt ggccgctcct    420 tccgtgttca tcttccctcc ctccgacgag cagctgaagt ccggcaccgc ctccgtggtg    480
tgtctgctga acaacttcta ccctcgggag gccaaggtgc agtggaaggt ggacaacgcc    540
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca gtccttcaa ccggggcgag    720 tgctgaagct t                                                         731
```

<210> SEQ ID NO 45
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Met Gly Trp Ser Cys Ile Ile Leu Phe Leu Val Ala Thr Ala Thr Gly
1               5                   10                  15

Val His Ser Gln Val Gln Leu Lys Glu Ser Gly Pro Gly Leu Val Ala
            20                  25                  30

Pro Ser Glu Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Pro
65                  70                  75                  80

Ser Leu Lys Ser Arg Leu Ser Ile Ser Lys Asp Asn Ser Lys Ser Gln
                85                  90                  95

Val Phe Leu Lys Val Thr Ser Leu Thr Thr Asp Asp Thr Ala Met Tyr
            100                 105                 110

Tyr Cys Ala Arg Ile Val Tyr Trp Gly Gln Gly Thr Leu Val Thr Val
        115                 120                 125

Ser Ala Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Ser Cys Pro
225                 230                 235                 240
```

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
        260                 265                 270

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Leu Gly
450                 455

<210> SEQ ID NO 46
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gctagcacca tgggctggag ctgcatcatc ctgttcctgg tggccaccgc caccggcgtg      60
cacagccagg tgcagctgaa ggagagcggc cccggcctgg tggcccccag cgagagcctg     120
agcatcacct gcaccgtgag cggcttcagc ctgatcgact acggcgtgaa ctggatccgc     180
cagccccccg gcaagggcct ggagtggctg ggcgtgatct ggggcgacgg caccacctac     240
tacaaccccg cctgaagag ccgcctgagc atcagcaagg acaacagcaa gagccaggtg     300
ttcctgaagg tgaccagcct gaccaccgac gacaccgcca tgtactactg cgcccgcatc     360
gtgtactggg gccagggcac cctggtgacc gtgagcgccg ccagcaccaa gggcccttcc     420
gtgttccctc tggccccttg ctcccggtcc acctccgagt ccaccgccgc tctgggctgc     480
ctggtgaagg actacttccc tgagcctgtg accgtgtcct ggaactctgg cgccctgacc     540
tccggcgtgc acaccttccc tgccgtgctg cagtcctccg gcctgtactc cctgtcctcc     600
gtggtgaccg tgccttcctc ctccctgggc accaagacct acacctgtaa cgtggaccac     660
aagccttcca acaccaaggt ggacaagcgg gtggagtcca agtacggccc ctccttgccct     720 tcctgccctg cccctgagtt cctgggcgga cctagcgtgt cctgttccc tcctaagcct     780

```
aaggacaccc tgatgatctc ccggacccct gaggtgacct gtgtggtggt ggacgtgtcc    840
caggaggacc ctgaggtcca gttcaactgg tacgtggacg gcgtggaggt gcacaacgcc    900
aagaccaagc ctcgggagga gcagttcaat tccacctacc gggtggtgtc tgtgctgacc    960
gtgctgcacc aggactggct gaacggcaaa gaatacaagt gtaaggtctc caacaagggc   1020 ctgcctcct ccatcgagaa aaccatctcc aaggccaagg gcagcctag ggagcctcag    1080 gtgtacaccc tgcctcctag ccaggaagag atgaccaaga accaggtgtc cctgacctgt   1140
ctggtgaagg gcttctaccc ttccgacatc gccgtggagt gggagtccaa cggccagcct   1200
gagaacaact acaagaccac ccctcctgtg ctggactccg acggctcctt cttcctgtac   1260
tccaggctga ccgtggacaa gtcccggtgg caggagggca cgtctttttc ctgctccgtg   1320
atgcacgagg ccctgcacaa ccactacacc cagaagtccc tgtccctgtc tctgggctga   1380
agctt                                                               1385
```

<210> SEQ ID NO 47
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Met Gly Trp Ser Cys Ile Ile Leu Phe Leu Val Ala Thr Ala Thr Gly
1               5                   10                  15

Val His Ser Glu Val Gln Leu Lys Glu Ser Gly Pro Gly Leu Val Ala
            20                  25                  30

Pro Gly Gly Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Ala
65                  70                  75                  80

Pro Leu Lys Gly Arg Leu Ser Ile Ser Lys Asp Asn Ser Lys Ser Gln
                85                  90                  95

Val Phe Leu Gln Met Asn Ser Leu Lys Thr Asp Asp Thr Ala Met Tyr
            100                 105                 110

Tyr Cys Ala Arg Ile Val Tyr Trp Gly Gln Gly Thr Leu Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Ser Cys Pro
225                 230                 235                 240

Ala Pro Glu Phe Leu Gly Gly Pro Ser Val Phe Leu Phe Pro Pro Lys
```

```
                    245                 250                 255
Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Gly Leu Pro Ser Ser Ile Glu Lys Thr Ile Ser Lys Ala Lys Gly Gln
        340                 345                 350

Pro Arg Glu Pro Gln Val Tyr Thr Leu Pro Pro Ser Gln Glu Glu Met
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Arg Leu Thr Val Asp Lys Ser Arg Trp Gln Glu Gly Asn Val
        420                 425                 430

Phe Ser Cys Ser Val Met His Glu Ala Leu His Asn His Tyr Thr Gln
    435                 440                 445

Lys Ser Leu Ser Leu Ser Leu Gly
450                 455
```

<210> SEQ ID NO 48
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
gctagcacca tgggctggag ctgcatcatc ctgttcctgg tggccaccgc caccggcgtg      60
cacagcgagg tgcagctgaa ggagagcggc cccggcctgg tgcccccgg cggcagcctg      120 agcatcacct gcaccgtgag cggcttcagc ctgatcgact acggcgtgaa ctggatccgc     180
cagccccccg gcaagggcct ggagtggctg ggcgtgatct ggggcgacgg caccacctac     240
tacaacgccc ccctgaaggg ccgcctgagc atcagcaagg acaacagcaa gagccaggtg     300
ttcctgcaga tgaacagcct gaagaccgac gacaccgcca tgtactactg cgcccgcatc     360
gtgtactggg gccagggcac cctggtgacc gtgagcagcg ccagcaccaa gggcccttcc     420
gtgttccctc tggccccttg ctccggtcc acctccgagt ccaccgccgc tctgggctgc     480
ctggtgaagg actacttccc tgagcctgtg accgtgtcct ggaactctgg cgccctgacc     540
tccggcgtgc acaccttccc tgccgtgctg cagtcctccg gcctgtactc cctgtcctcc     600
gtggtgaccg tgccttcctc ctcccctggc accaagacct acacctgtaa cgtggaccac     660
aagccttcca acaccaaggt ggacaagcgg gtggagtcca gtacggccc tccttgccct     720 tcctgccctg cccctgagtt cctgggcgga cctagcgtgt tcctgttccc tcctaagcct     780
aaggacaccc tgatgatctc ccggacccct gaggtgacct gtgtggtggt ggacgtgtcc     840
```

-continued

```
caggaggacc ctgaggtcca gttcaactgg tacgtggacg gcgtggaggt gcacaacgcc    900
aagaccaagc ctcgggagga gcagttcaat tccacctacc gggtggtgtc tgtgctgacc    960
gtgctgcacc aggactggct gaacggcaaa gaatacaagt gtaaggtctc caacaagggc   1020 ctgcccctcct ccatcgagaa aaccatctcc aaggccaagg gccagcctag ggagcctcag   1080
gtgtacaccc tgcctcctag ccaggaagag atgaccaaga accaggtgtc cctgacctgt   1140
ctggtgaagg gcttctaccc ttccgacatc gccgtggagt gggagtccaa cggccagcct   1200
gagaacaact acaagaccac ccctcctgtg ctggactccg acggctcctt cttcctgtac   1260
tccaggctga ccgtggacaa gtcccggtgg caggagggca acgtcttttc ctgctccgtg   1320
atgcacgagg ccctgcacaa ccactacacc cagaagtccc tgtccctgtc tctgggctga   1380
agctt                                                                1385
```

<210> SEQ ID NO 49
<211> LENGTH: 5
<212> TYPE: PRT
<213> ORGANISM: Homo sapiens

<400> SEQUENCE: 49

Glu Leu Leu Gly Gly
1               5

<210> SEQ ID NO 50
<211> LENGTH: 5
<212> TYPE: PRT
<213> ORGANISM: Homo sapiens

<400> SEQUENCE: 50

Met Ile Ser Arg Thr
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 51

His His His His His His
1               5

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Gly Lys Ala Pro Gln Leu Leu Ile Tyr Arg Met Ser Asn Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Gly Lys Ala Pro Lys Leu Leu Ile Tyr Ala Ala Ser Ser Leu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Leu Ile Asp Tyr Gly Val Asn Trp Ile Arg Gln Pro Pro Gly
1               5                   10                  15

<210> SEQ ID NO 55
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Met Thr Gln Ala Ala Pro Ser Val Ala Val Thr Pro Gly
1               5                   10                  15

Gln Ser Val Ser Ile Ser Cys Arg Ser Ser Lys Ser Leu Leu His Ser
                20                  25                  30

Ser Gly Lys Thr Tyr Leu Tyr Trp Phe Leu Gln His Pro Gly Lys Ala
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Thr Ile
65                  70                  75                  80

Ser Gly Val Gln Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 56
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
                20                  25                  30

Gly Val Asn Trp Ile Arg Gln Pro Pro Gly Lys Gly Leu Glu Trp Leu
            35                  40                  45

Gly Val Ile Trp Gly Asp Gly Thr Thr Tyr Tyr Asn Ser Ala Leu Lys
    50                  55                  60

Ser Arg Leu Ser Ile Ser Lys Asp Thr Ser Lys Ser Gln Val Phe Leu
65                  70                  75                  80

Lys Met Asn Ser Leu Thr Thr Asp Asp Thr Ala Met Tyr Tyr Cys Ala

```
                    85                  90                  95

Arg Ile Val Tyr Trp Gly Gln Gly Thr Leu Val Thr Val Ser Ala Ala
            100                 105                 110

Lys

<210> SEQ ID NO 57
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Pro Ser Ala Leu Lys
    50                  55                  60

Ser Arg Leu Ser Ile Ser Lys Asp Thr Ser Lys Ser Gln Val Phe Leu
65                  70                  75                  80

Lys Met Asn Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala Ala
            100                 105                 110

Lys

<210> SEQ ID NO 58
<211> LENGTH: 16
<212> TYPE: PRT
<213> ORGANISM: Artificial Sequence
<220> FEATURE:
<223> OTHER INFORMATION: Synthetic peptide

<400> SEQUENCE: 58

Arg Ser Ser Lys Ser Leu Leu His Ser Gly Lys Thr Tyr Leu Tyr
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Arg Met Ser Asn Leu Ala Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Met Gln His Leu Glu Tyr Pro Tyr Thr
1               5
```

<210> SEQ ID NO 61
<211> LENGTH: 10
<212> TYPE: PRT
<213> ORGANISM: Artificial Sequence
<220> FEATURE:
<223> OTHER INFORMATION: Synthetic peptide

<400> SEQUENCE: 61

Gly Phe Ser Leu Ile Asp Tyr Gly Val Asn
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Val Ile Trp Gly Asp Gly Thr Thr Tyr
1               5

<210> SEQ ID NO 63
<211> LENGTH: 3
<212> TYPE: PRT
<213> ORGANISM: Artificial Sequence
<220> FEATURE:
<223> OTHER INFORMATION: Synthetic peptide

<400> SEQUENCE: 63

Ile Val Tyr
1

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Arg Leu Ser Asn Leu Ala Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic peptide

<400> SEQUENCE: 65

Arg Leu Ser Ser Asn Leu Ala Ser
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide

<400> SEQUENCE: 66

Arg Met Ser Asn Leu Ala
1               5

-continued

```
<210> SEQ ID NO 67
<211> LENGTH: 6
<212> TYPE: PRT
<213> ORGANISM: Artificial Sequence
<220> FEATURE:
<223> OTHER INFORMATION: Synthetic peptide

<400> SEQUENCE: 67

Arg Leu Ser Asn Leu Ala
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide

<400> SEQUENCE: 68

Arg Leu Ser Ser Leu Ala
1               5

<210> SEQ ID NO 69
<211> LENGTH: 17
<212> TYPE: PRT
<213> ORGANISM: Artificial Sequence
<220> FEATURE:
<223> OTHER INFORMATION: Synthetic peptide

<400> SEQUENCE: 69

Arg Ser Ser Lys Ser Leu Leu His Ser Ser Gly Lys Thr Tyr Leu Tyr
1               5                   10                  15

Trp

<210> SEQ ID NO 70
<211> LENGTH: 113
<212> TYPE: PRT
<213> ORGANISM: Artificial Sequence
<220> FEATURE:
<223> OTHER INFORMATION: Light Chain

<400> SEQUENCE: 70

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
                20                  25                  30

Ser Gly Lys Thr Tyr Leu Tyr Trp Phe Leu Gln Arg Pro Gly Gln Ser
            35                  40                  45

Pro Gln Leu Leu Ile Tyr Arg Leu Ser Ser Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

Arg

<210> SEQ ID NO 71
<211> LENGTH: 219
<212> TYPE: PRT
<213> ORGANISM: Artificial Sequence
```

<220> FEATURE:
<223> OTHER INFORMATION: Light chain with constant region

<400> SEQUENCE: 71

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Leu Ala Ser Gly Val Pro
    50                  55                  60

Asp Arg Phe Ser Gly Ser Gly Ser Gly Thr Ala Phe Thr Leu Arg Ile
65              70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 72
<211> LENGTH: 437
<212> TYPE: PRT
<213> ORGANISM: Artificial Sequence
<220> FEATURE:
<223> OTHER INFORMATION: Heavy chain with constant region

<400> SEQUENCE: 72

Gln Val Gln Leu Lys Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Pro Ser Leu Lys
    50                  55                  60

Ser Arg Leu Ser Ile Ser Lys Asp Asn Ser Lys Ser Gln Val Phe Leu
65              70                  75                  80

Lys Val Thr Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala Ala
            100                 105                 110

Ser Thr Lys Gly Pro Ser Val Phe Pro Leu Ala Pro Cys Ser Arg Ser

```
            115                 120                 125
Thr Ser Glu Ser Thr Ala Ala Leu Gly Cys Leu Val Lys Asp Tyr Phe
        130                 135                 140
Pro Glu Pro Val Thr Val Ser Trp Asn Ser Gly Ala Leu Thr Ser Gly
145                 150                 155                 160
Val His Thr Phe Pro Ala Val Leu Gln Ser Ser Gly Leu Tyr Ser Leu
                165                 170                 175
Ser Ser Val Val Thr Val Pro Ser Ser Ser Leu Gly Thr Lys Thr Tyr
                180                 185                 190
Thr Cys Asn Val Asp His Lys Pro Ser Asn Thr Lys Val Asp Lys Arg
            195                 200                 205
Val Glu Ser Lys Tyr Gly Pro Pro Cys Pro Pro Cys Pro Ala Pro Glu
        210                 215                 220
Phe Glu Gly Gly Pro Ser Val Phe Leu Phe Pro Pro Lys Pro Lys Asp
225                 230                 235                 240
Thr Leu Met Ile Ser Arg Thr Pro Glu Val Thr Cys Val Val Val Asp
                245                 250                 255
Val Ser Gln Glu Asp Pro Glu Val Gln Phe Asn Trp Tyr Val Asp Gly
                260                 265                 270
Val Glu Val His Asn Ala Lys Thr Lys Pro Arg Glu Glu Gln Phe Asn
            275                 280                 285
Ser Thr Tyr Arg Val Val Ser Val Leu Thr Val Leu His Gln Asp Trp
        290                 295                 300
Leu Asn Gly Lys Glu Tyr Lys Cys Lys Val Ser Asn Lys Gly Leu Pro
305                 310                 315                 320
Ser Ser Ile Glu Lys Thr Ile Ser Lys Ala Lys Gly Gln Pro Arg Glu
                325                 330                 335
Pro Gln Val Tyr Thr Leu Pro Pro Ser Gln Glu Glu Met Thr Lys Asn
                340                 345                 350
Gln Val Ser Leu Thr Cys Leu Val Lys Gly Phe Tyr Pro Ser Asp Ile
            355                 360                 365
Ala Val Glu Trp Glu Ser Asn Gly Gln Pro Glu Asn Asn Tyr Lys Thr
        370                 375                 380
Thr Pro Pro Val Leu Asp Ser Asp Gly Ser Phe Phe Leu Tyr Ser Arg
385                 390                 395                 400
Leu Thr Val Asp Lys Ser Arg Trp Gln Glu Gly Asn Val Phe Ser Cys
                405                 410                 415
Ser Val Met His Glu Ala Leu His Asn His Tyr Thr Gln Lys Ser Leu
                420                 425                 430
Ser Leu Ser Leu Gly
            435
```